United States Patent
Kielczewska et al.

(10) Patent No.: US 11,505,614 B2
(45) Date of Patent: Nov. 22, 2022

(54) ANTIBODIES BINDING TO SOLUBLE BCMA

(71) Applicant: AMGEN INC., Thousand Oaks, CA (US)

(72) Inventors: Agnieszka Kielczewska, Thousand Oaks, CA (US); Brian Chan, Thousand Oaks, CA (US)

(73) Assignee: AMGEN INC., Thousand Oaks, CA (US)

(*) Notice: Subject to any disclaimer, the term of this patent is extended or adjusted under 35 U.S.C. 154(b) by 203 days.

(21) Appl. No.: 16/585,318

(22) Filed: Sep. 27, 2019

(65) Prior Publication Data

US 2020/0102398 A1 Apr. 2, 2020

Related U.S. Application Data

(60) Provisional application No. 62/738,997, filed on Sep. 28, 2018.

(51) Int. Cl.
| | |
|---|---|
| *C07K 16/28* | (2006.01) |
| *A61P 35/02* | (2006.01) |
| *G01N 33/574* | (2006.01) |
| *G01N 33/82* | (2006.01) |

(52) U.S. Cl.
CPC .......... *C07K 16/2878* (2013.01); *A61P 35/02* (2018.01); *G01N 33/57426* (2013.01); *G01N 33/82* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 4,751,180 A | 6/1988 | Cousens et al. | |
| 4,816,397 A | 3/1989 | Boss et al. | |
| 4,816,567 A | 3/1989 | Cabilly et al. | |
| 4,935,233 A | 6/1990 | Bell et al. | |
| 5,223,409 A | 6/1993 | Ladner et al. | |
| 5,225,539 A | 7/1993 | Winter | |
| 5,292,658 A | 3/1994 | Cormier et al. | |
| 5,418,155 A | 5/1995 | Cormier et al. | |
| 5,565,332 A | 10/1996 | Hoogenboom et al. | |
| 5,585,089 A | 12/1996 | Queen et al. | |
| 5,648,260 A | 7/1997 | Winter et al. | |
| 5,683,888 A | 11/1997 | Campbell | |
| 5,693,761 A | 12/1997 | Queen et al. | |
| 5,693,762 A | 12/1997 | Queen et al. | |
| 5,741,668 A | 4/1998 | Ward et al. | |
| 5,777,079 A | 7/1998 | Tsien et al. | |
| 5,804,387 A | 9/1998 | Cormack et al. | |
| 5,859,205 A | 1/1999 | Adair et al. | |
| 5,874,304 A | 2/1999 | Zolotukhin et al. | |
| 5,876,995 A | 3/1999 | Bryan | |
| 5,925,558 A | 7/1999 | Tsien et al. | |
| 6,407,213 B1 | 6/2002 | Carter et al. | |
| 6,706,265 B1 | 3/2004 | Bolt et al. | |
| 7,381,803 B1 | 6/2008 | Weiner et al. | |
| 7,728,114 B2 | 6/2010 | Mach et al. | |
| 7,994,289 B2 | 8/2011 | Waldmann et al. | |
| 9,150,664 B2 * | 10/2015 | Kufer | C07K 14/70578 |
| 9,340,621 B2 * | 5/2016 | Kufer | A61K 39/0005 |
| 9,598,500 B2 * | 3/2017 | Kufer | C07K 14/70578 |
| 10,752,694 B2 * | 8/2020 | Kufer | A61P 7/00 |
| 10,766,969 B2 * | 9/2020 | Kufer | A61P 17/00 |
| 2003/0070185 A1 | 4/2003 | Jakobovits et al. | |
| 2014/0302037 A1 | 10/2014 | Borges et al. | |
| 2014/0308285 A1 | 10/2014 | Yan et al. | |

FOREIGN PATENT DOCUMENTS

| | | |
|---|---|---|
| EP | 0171496 A2 | 2/1986 |
| EP | 0173494 A2 | 3/1986 |
| EP | 0239400 B1 | 8/1994 |
| EP | 3029068 A1 | 6/2016 |
| GB | 2177096 A | 1/1987 |
| WO | 1988/09344 A1 | 12/1988 |
| WO | 1992/15673 A1 | 9/1992 |
| WO | 1995/07463 A1 | 3/1995 |
| WO | 1996/33735 A1 | 10/1996 |
| WO | 1996/34096 A1 | 10/1996 |
| WO | 1998/14605 A1 | 4/1998 |
| WO | 1998/26277 A2 | 6/1998 |
| WO | 1999/49019 A2 | 9/1999 |
| WO | 1999/54440 A1 | 10/1999 |
| WO | 2000/06605 A2 | 2/2000 |
| WO | 2005/040220 A1 | 5/2005 |
| WO | 2008/119567 A2 | 10/2008 |
| WO | 2010/037838 A2 | 4/2010 |

(Continued)

OTHER PUBLICATIONS

Almagro & Fransson, Frontiers in Bioscience 2008; 13:1619-33 (Year: 2008).*

WH0000608M1 (Sigma-Aldrich downloaded Oct. 20, 2021, https://www.sigmaaldrich.com/US/en/product/sigma/wh0000608m1?context=product) (Year: 2021).*

Hornbeck et al. (Enzyme-Linked Immunosorbent Assays (ELISA) Current Protocols in Molecular Biology 1991, 11.2.1-11.2.22) (Year: 1991).*

Ghermezi et al., Serum B-Cell Maturation Antigen: A Novel Biomarker to Predict Outcomes for Multiple Myeloma Patients, Haematologica, 102:785-795 (2017).

(Continued)

*Primary Examiner* — Peter J Reddig

(74) *Attorney, Agent, or Firm* — Marshall, Gerstein & Borun LLP

(57) ABSTRACT

The present invention relates to antibodies that bind to soluble BCMA (sBCMA). Moreover, the invention relates to a detection system comprising such antibodies. The antibodies or the detection system may be used for detecting or quantifying sBCMA, for diagnosing a disease associated with sBCMA, for patient stratification, monitoring disease progression, and evaluating the therapeutic response.

28 Claims, 5 Drawing Sheets

Specification includes a Sequence Listing.

(56) References Cited

FOREIGN PATENT DOCUMENTS

| WO | 2013/026833 | A1 | | 2/2013 | |
|---|---|---|---|---|---|
| WO | 2013/026837 | A1 | | 2/2013 | |
| WO | 2013/072406 | A1 | | 5/2013 | |
| WO | 2014/089335 | A2 | | 6/2014 | |
| WO | 2014/144722 | A2 | | 9/2014 | |
| WO | 2014/151910 | A1 | | 9/2014 | |
| WO | 2015/048272 | A1 | | 4/2015 | |
| WO | 2017/083511 | A1 | | 5/2017 | |
| WO | WO-2017123741 | A1 | * | 7/2017 | ......... G01N 33/6893 |
| WO | 2017/134134 | A1 | | 8/2017 | |

OTHER PUBLICATIONS

International Search Report and Written Opinion for Corresponding International Application No. PCT/US2019/053433, dated Jan. 14, 2020, 15 pages.
Pérez De La Lastra et al., Epitope mapping of 10 monoclonal antibodies against the pig analogue of human membrane cofactor protein (MCP), Immunology, 96:663-670 (1999).
Sanchez et al., Serum B-cell maturation antigen is elevated in multiple myeloma and correlates with disease status and survival, British Journal of Haematology, 158:727-738 (2012).
Altschul et al., Basic local alignment search tool, J. Mol. Biol., 215(3):1403-10 (1990).
Altschul et al., Gapped BLAST and PSI-BLAST: a new generation of protein database search programs, Nucleic Acids Res., 25(17):3389-402 (1997).
Altschul et al., Local alignment statistics, Methods Enzymol., 266:460-80 (1996).
Artsaenko et al., Expression of a single-chain Fv antibody against abscisic acid creates a wilty phenotype in transgenic tobacco. The Plant J., 8:745-750 (1995).
Carter et al., High level *Escherichia coli* expression and production of a bivalent humanized antibody fragment, Biotechnology (NY), 10(2):163-7 (1992).
Chalfie et al., Green fluorescent protein as a marker for gene expression, Science, 263:802-805 (1994).
Cheadle et al., Cloning and expression of the variable regions of mouse myeloma protein MOPC315 in *E. coli*: recovery of active FV fragments, Mol Immunol., 29:21-30 (1992).
Chothia et al., Canonical structures for the hypervariable regions of immunoglobulins, J. Mol. Biol., 196:901-917 (1987).
Chothia et al., Conformations of immunoglobulin hypervariable regions, Nature, 342:877-83 (1989).
Clackson et al., Making antibody fragments using phage display libraries, Nature, 352:624-628 (1991).
Cole et al., The EBV-hybridoma technique and its application to human lung cancer, Monoclonal Antibodies and Cancer Therapy, Alan R. Liss, Inc., 77-96 (1985).
Creighton, Proteins: Structure and Molecular Properties, W. H. Freeman & Co., San Francisco, 79-86 (1983).
Cunningham et al., High-resolution epitope mapping of hGH-receptor interactions by alanine-scanning mutagenesis, Science, 244(4908):1081-5 (1989).
Dall'Acqua et al., Contribution of domain interface residues to the stability of antibody CH3 domain homodimers, Biochem., 37:9266-9273 (1998).
Devereux et al., A comprehensive set of sequence analysis programs for the VAX, Nucleic Acids Res., 12(1 Pt 1):387-95(1984).
Fecker et al., Expression of single-chain antibody fragments (scFv) specific for beet necrotic yellow vein virus coat protein or 25 kDa protein in *Escherichia coli* and Nicotiana benthamiana. Plant. Mol. Biol., 32:979-986 (1996).
Feng et al., Progressive sequence alignment as a prerequisite to correct phylogenetic trees, J. Mol. Evol., 25(4):351-60(1987).
GenBank Accession No. U55762, Version U55762.1, Cloning vector pEGFP-N1, complete sequence, enhanced green fluorescent protein (egfp) and neomycin phosphotransferase genes, complete cds, last updated Aug. 22, 2003, located at < https://www.ncbi.nlm.nih.gov/nuccore/U55762 >.
George et al., Macromolecular sequencing and synthesis, Selected methods and applications, 127-149, Alan R. Liss, Inc. (1988).
Graham et al., Characteristics of a human cell line transformed by DNA from human adenovirus type 5, J. Gen. Virol., 36:59-74 (1977).
Green et al., Antigen-specific human monoclonal antibodies from mice engineered with human Ig heavy and light chain YACs, Nat. Genet, 7:13-21 (1994).
Harlow et al., Antibodies: A Laboratory Manual, Cold Spring Harbor Laboratory, Eds., 1988.
Hawkins et al., Selection of phage antibodies by binding affinity mimicking affinity maturation, J. Mol. Biol., 254889-896 (1992).
Heim et al., Engineering green fluorescent protein for improved brightness, longer wavelengths and fluorescence resonance energy transfer, Curr Biol., 6:178-182 (1996).
Hiatt et al., Production of antibodies in transgenic plants, Nature, 342:76-78 (1989).
Higgins et al., Fast and sensitive multiple sequence alignments on a microcomputer, Comput. Appl. Biosci., 5(2):151-3(1989).
Honjo et al., Immunoglobulin genes, 2nd ed., eds. Academic Press, San Diego, CA (1995).
Huston et al., Protein engineering of antibody binding sites: recovery of specific activity in an anti-digoxin single-chain Fv analogue produced in *Escherichia coli*, Proc. Natl. Acad Sci. USA., 85:5879-5883(1988).
Ichiki et al., Regulation of the expression of human C epsilon germline transcript. Identification of a novel IL-4 responsive element, J. Immunol., 150:5408-5417 (1993).
Jones et al., Replacing the complementarity-determining regions in a human antibody with those from a mouse, Nature, 321:522-525 (1986).
Kabat et al., Sequences of Proteins of Immunological Interest, Bethesda, National Institute of Health (1991).
Karlin et al., Applications and statistics for multiple high-scoring segments in molecular sequences, Proc. Natl. Acad. Sci. USA., 90(12):5873-7 (1993).
Kohler et al., Continuous cultures of fused cells secreting antibody of predefined specificity, Nature, 256:495-7 (1975).
Kontermann et al., Antibody engineering, springer, 2nd ed., (2010).
Kozbor et al., The production of monoclonal antibodies from human lymphocytes, Immunol. Today, 4:72-79 (1983).
Little, Recombinant antibodies for immunotherapy, Cambridge University Press (2009).
Lowman et al., Selecting high-affinity binding proteins by monovalent phage display, Biochemistry, 30:10832-10837 (1991).
MacCallum et al., Antibody-antigen interactions: contact analysis and binding site topography, J. Mol. Biol., 262:732-45 (1996).
Malmborg et al., BIAcore as a tool in antibody engineering, J. Immunol. Methods, 183:7-13 (1995).
Marks et al., By-passing immunization. Human antibodies from V-gene libraries displayed on phage, J. Mol. Biol., 222:581-597 (1991).
Martin et al., Structural families in loops of homologous proteins: automatic classification, modelling and application to antibodies, J. Mol. Biol., 263:800-15 (1996).
Mather et al., Culture of testicular cells in hormone-supplemented serum-free medium, Ann. N.Y. Acad. Sci., 383:44-68 (1982).
Mather, Establishment and characterization of two distinct mouse testicular epithelial cell lines, Biol. Reprod., 23:243-251 (1980).
Morrison et al., Chimeric human antibody molecules: mouse antigen-binding domains with human constant region domains, Proc. Natl. Acad. Sci. USA, 81:6851-6855 (1984).
Morrison et al., Combinatorial alanine-scanning, Curr. Opin. Chem. Biol., 5(3):302-7 (2001).
Morrison, Transfectomas provide novel chimeric antibodies, Science, 229:1202-1207 (1985).
Needleman et al., A general method applicable to the search for similarities in the amino acid sequence of two proteins, J. Mol. Biol., 48(3):443-53 (1970).

(56) References Cited

OTHER PUBLICATIONS

Nolan et al., Fluorescence-activated cell analysis and sorting of viable mammalian cells based on beta-D-galactosidase activity after transduction of *Escherichia coli* lacZ, Proc. Natl. Acad. Sci. U.S.A., 85:2603-2607 (1988).
Ol et al., Chimeric antibodies, BioTechnique, 4:214-21 (1986).
Olsson et al., Human-human monoclonal antibody-producing hybridomas: technical aspects, Meth. Enzymol., 92:3-16(1982).
Owen et al.. Synthesis of a functional anti-phytochrome single-chain Fv protein in transgenic tobacco, Biotechnology, 10:790-794(1992).
Pearson et al., Improved tools for biological sequence comparison, Proc. Natl. Acad. Sci. USA., 85(8):2444-8 (1988).
Presta, Antibody engineering, Curr. Opin. Struct. Biol., 2:593-596 (1992).
Raag et al., Single-chain Fvs, FASEB., 9(1)73-80 (1995).
Reichmann et al., Reshaping human antibodies for therapy, Nature, 332:323-329 (1988).
Sambrook et al., Molecular cloning: A laboratory manual, Cold spring harbor laboratory press, Cold spring harbor, New York, (2001).
Schier et al., Efficient in vitro affinity maturation of phage antibodies using BIAcore guided selections, Human Antibodies Hybridomas, 7:97-105 (1996).
Smith et al., Comparison of biosequences, Adv. Appl. Math., 2:482-489 (1981).
Smith, Filamentous fusion phage: novel expression vectors that display cloned antigens on the virion surface, Science, 228:1315-1317 (1985).
Stauber et al., Development and applications of enhanced green fluorescent protein mutants, Biotechniques, 24:462-471 (1998).
Takeda et al., Construction of chimaeric processed immunoglobulin genes containing mouse variable and human constant region sequences, Nature, 314:452-4 (1985).
Teng et al., Construction and testing of mouse-human heteromyelomas for human monoclonal antibody production, Proc. Natl. Acad. Sci U.S.A., 80:7308-7312 (1983).
Urlaub et al., Isolation of Chinese hamster cell mutants deficient in dihydrofolate reductase activity, Proc. Natl. Acad. Sci. USA., 77:4216-20 (1980).
Ward et al., Binding activities of a repertoire of single immunoglobulin variable domains secreted from *Escherichia coli*, Nature, 341:544-546 (1989).

\* cited by examiner

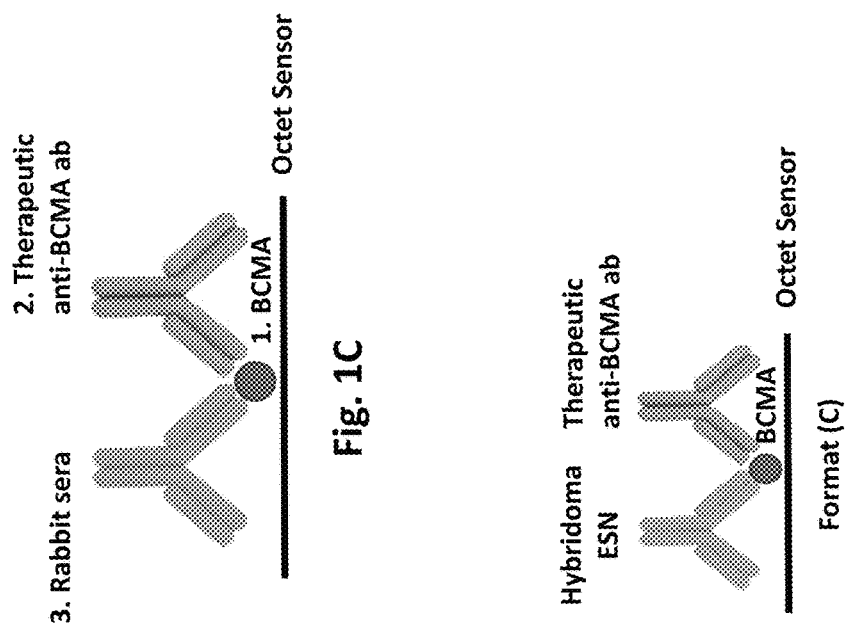
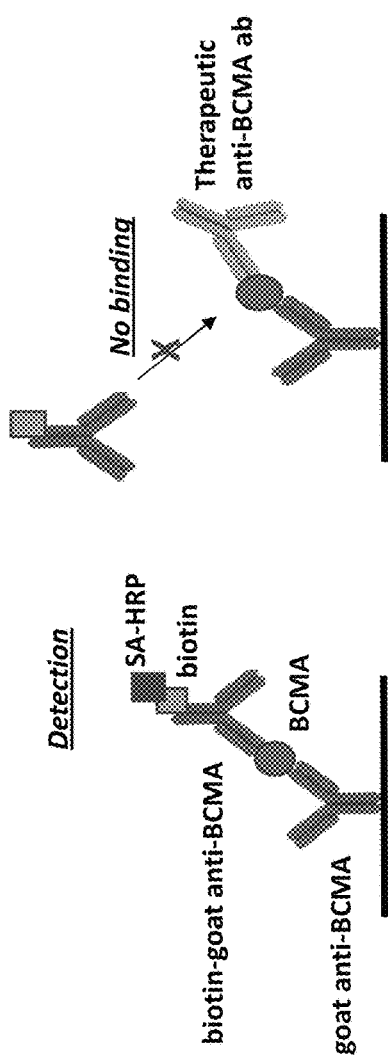
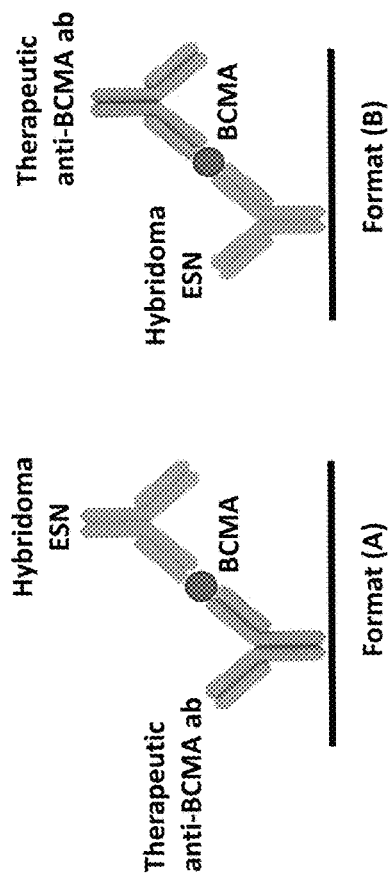
Fig. 1A
Fig. 1B
Fig. 1C

ANTIBODIES BINDING TO SOLUBLE BCMA

FIELD

The present invention relates to antibodies that bind to soluble BCMA (sBCMA). Moreover, the invention relates to a detection system comprising such antibodies. The antibodies or the detection system may be used for detecting or quantifying sBCMA, for diagnosing a disease associated with sBCMA, for patient stratification, monitoring disease progression, and evaluating the therapeutic response.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 34,276 bytes ASCII (Text) file named "53500A_Seqlisting.txt"; created on Sep. 27, 2019.

BACKGROUND

Multiple myeloma (MM) is a neoplastic plasma-cell disorder that is characterized by clonal proliferation of malignant plasma cells in the bone marrow microenvironment, monoclonal protein in the blood or urine and associated organ dysfunction. Multiple Myeloma (MM) accounts for almost 2% of all cancers and 20% of hematologic malignancies (SEER). Multiple myeloma remains an incurable cancer, although recent improved understanding of pathogenesis of myeloma has led to the development of new treatments and improved survival. Treatments include molecularly targeted therapies that are designed to inhibit signaling pathways that support neoplastic cell survival and proliferation. One such target is the B-cell maturation antigen which is largely expressed at relatively higher levels on malignant plasma cells than on normal plasma cells and induces proliferative signals through the binding of its ligands APRIL and BAFF.

B cell maturation antigen (BCMA, TNFRSF17, CD269) is a transmembrane protein belonging to the TNF receptor super family. BCMA expression is selectively induced during late stage plasma cell differentiation and is absent on naive and memory B cells. Upon BCMA binding to its ligands, B cell activating factor (BAFF) and a proliferation inducing ligand (APRIL), the survival of the bone marrow plasma cells and plasmablasts is promoted. BCMA does not maintain normal B cell homeostasis, but is required for the survival of long lived plasma cells. The mRNA expression of BCMA is highly elevated in malignant plasma cell disorders. By contrast, BCMA mRNA expression in normal tissues is very low and restricted to lymphoid tissues where normal long-lived plasma cells are located. BCMA protein expression is reported to be restricted to plasma cells only and confined to plasma blasts and long-lived plasma cells and cannot be detected on other normal human tissues. BCMA is expressed at a relatively higher level on the majority of malignant plasma cells compared to normal plasma cells in MM patients. Neither T cells nor myeloid cells or CD34+ hematopoietic stem cells express BCMA. The selective expression of BCMA in the majority of malignant plasma cells makes it a very attractive target for antibody-based and chimeric antigen receptor (CAR)-based therapies. There are reports of BCMA-negative profiles for MM patients suggesting that patient selection may be required for targeted therapy. Detection of BCMA may not be limited to protein expression. Recent studies have shown that change in serum BCMA may be a biomarker for therapeutic response or disease progression for patients with MM.

BCMA can be shed from the cell surface and was found in serum samples of multiple myeloma patients as well as in healthy subjects. A recent publication demonstrated that soluble BCMA (sBCMA) levels correlated with the proportion of plasma cells in bone marrow biopsies, clinical status, and can be tracked with changes in M-protein levels. In this study, healthy donors had a median sBCMA blood concentration similar to median levels observed in patients with complete response. Patients with smoldering multiple myeloma had higher concentrations, whereas patients with active untreated multiple myeloma had highest levels. Progression-free survival was longer for patients with sBCMA levels below the median when compared with those whose levels were above the median. Changes in sBCMA levels may be a rapid and reliable indicator of treatment efficacy for patients with MM. Soluble BCMA may be used for prognosing or monitoring disease progress, as this biomarker can be detected in patients with low tumor burden with non-secretory disease and is independent of renal function.

There is hence a high need for providing a reliable detection system for sBCMA in a biological sample, having high sensitivity, reproducibility and ideally providing stable results in the presence of potentially interfering therapeutic sBCMA-binding molecules such as antibodies or antibody constructs.

BRIEF DESCRIPTION OF THE DRAWINGS

FIG. 1A-C depicts the setup of the assays carried out according to Example 1. FIG. 1A shows the assay setup for testing the potential interference of a therapeutic anti-BCMA ab with a BCMA detection/quantitation ELISA kit. FIG. 1B shows three different Octet formats for the use of a capture and a detection antibody in the screening of XenoMouse® anti-BCMA hybridomas for binding to BCMA in the presence of a monoclonal therapeutic anti-sBCMA antibody. FIG. 1C shows the assay setup for screening rabbit sera for sandwiching with a therapeutic anti-BCMA ab.

SUMMARY AND DETAILED DESCRIPTION

Figure 2:
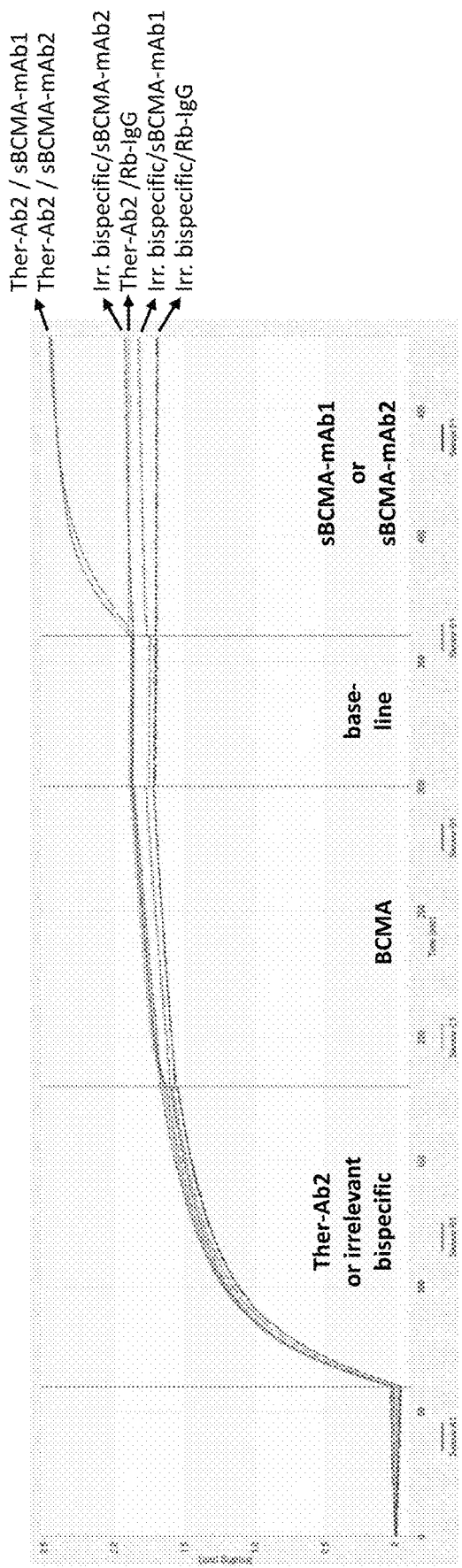
FIG. 2 shows the characterization of two rabbit monoclonal anti-sBCMA Abs (sBCMA-mAb1 and sBCMA-mAb2) for sandwiching with a therapeutic anti-BCMA Ab (Ther-Ab2) in an Octet assay (see Example 2a).

In an effort to generate an antibody pair to detect sBCMA, the present inventors have screened about 400 XenoMouse® hybridomas that had been generated against BCMA and tested positive in an ELISA assay for binding to BCMA. However, the screening of these XenoMouse® hybridomas in the presence of a monoclonal antibody binding to sBCMA did not identify any sandwiching antibody, even when testing different formats of the use of the capture and detection antibodies (see FIG. 1B). Next, rabbit immunization campaigns were carried out, and the rabbit sera were screened for sandwiching with the monoclonal antibody binding to sBCMA. The advantages of using rabbits for antibody generation in the present case are:

Different antibody repertoire, different epitope space (no competition)

Robust immune response

Gene conversion based immune system, higher rates of somatic hypermutation than rodents, leading to high affinities The existence of three sandwiching antibodies (out of a total number of 226 rabbit antibodies against sBCMA) could be demonstrated. Two of those (sBCMA-mAb1 and sBCMA-mAb2) were shown to compete with each other for the binding to sBCMA. They were both able to bind to sBCMA in the presence of a therapeutic anti-BCMA antibody construct. Antibody sBCMA-mAb3 was further shown to bind to sBCMA in the presence of both sBCMA-mAb1 and a therapeutic anti-BCMA antibody construct.

Therefore, the present invention provides in one aspect a monoclonal antibody (or antibody construct) that binds to soluble BCMA (sBCMA), wherein the binding of the antibody (or antibody construct) to sBCMA occurs in the presence of a second monoclonal antibody (or antibody construct) binding to sBCMA. The present invention also provides a monoclonal antibody (or antibody construct) that binds to soluble BCMA (sBCMA) in the presence of a second monoclonal antibody (or antibody construct) binding to sBCMA.

In the following, whenever the term "monoclonal antibody" is used (i.e. monoclonal antibody that binds to sBCMA), the term is meant to also encompass "antibody constructs" or "antibody fragments", as they will be defined herein below. Furthermore, the below provided definitions and specifications of the "monoclonal antibody (or antibody construct)" of the present invention (i.e. monoclonal antibody or antibody construct that binds to sBCMA) similarly apply to any "first monoclonal antibody (or antibody construct)" of the invention as well as any "second monoclonal antibody (or antibody construct)" of the invention.

An "antibody" (sometimes also known as an immunoglobulin) is a protein that immunospecifically binds to its target. The antibody recognizes a unique target, called an antigen, via its variable regions. An "antibody" may be of any immunoglobulin isotype, including IgG (including IgG1, IgG2, IgG3 and IgG4 subtypes), IgA (including IgA1 and IgA2 subtypes), IgM and IgE. The term "antibody" may include, for instance, monoclonal, chimeric, recombinant, deimmunized, affinity matured, humanized and human antibodies, as well as antibodies from other species such as rodent, rabbit, mouse, rat, hamster, goat etc. Antibodies may be derived solely from a single source, or may be "chimeric," that is, different portions of the antibody (such as CDRs, framework regions, variable region, constant region) may be derived from two different antibodies. The definition of "antibody" according to the invention comprises full-length antibodies, also including camelid antibodies, and other immunoglobulins generated by biotechnological or protein engineering methods or processes. An antibody may also be produced in hybridomas.

An intact IgG antibody generally will comprise two full-length heavy chains and two full-length light chains. A "light chain" includes a variable region ("VL") having one domain, and a constant region ("CL") having one domain. The variable region of the light chain is at the amino-terminus of the polypeptide. Light chains include kappa chains and lambda chains. A "heavy chain" includes a variable region ("VH") having one domain, and a constant region ("CH") having—in the case of an intact IgG antibody—three domains: CH1, CH2, and CH3. The VH is at the amino-terminus of the polypeptide, and the CH domains are at the carboxyl-terminus, with the CH3 being closest to the carboxy-terminus of the polypeptide.

In a classical full-length antibody or immunoglobulin, each light (L) chain is linked to a heavy (H) chain by one covalent disulfide bond, while the two H chains are linked to each other by one or more disulfide bonds depending on the H chain isotype. The heavy chain constant (CH) domain most proximal to VH is usually designated as CH1. The constant ("C") domains are not directly involved in antigen binding, but exhibit various effector functions, such as antibody-dependent cell-mediated cytotoxicity (ADCC) and complement activation (complement dependent cytotoxicity, CDC). The Fc region of an antibody is the "tail" region of a classical antibody that interacts with cell surface receptors called Fc receptors and some proteins of the complement system. In IgG, IgA and IgD antibody isotypes, the Fc region is composed of two identical protein fragments, derived from the second and third constant domains (CH2 and CH3) of the antibody's two heavy chains. IgM and IgE Fc regions contain three heavy chain constant domains (CH2, CH3 and CH4) in each polypeptide chain. The Fc regions also contains part of the so-called "hinge" region held together by one or more disulfides and noncovalent interactions. The Fc region of a naturally occurring IgG bears a highly conserved N-glycosylation site. Glycosylation of the Fc fragment is essential for Fc receptor-mediated activity.

It is envisaged that the monoclonal antibody of the present invention may be an IgG, IgD, IgE, IgM or IgA antibody. According to one embodiment, the monoclonal antibody is an IgG antibody, such as an IgG1, IgG2, IgG3 or IgG4 antibody. The isotype and subclass of the antibody may be of rabbit (e.g. rabbit IgG, rabbit IgG1 etc.).

In the context of the present invention, the term "variable" refers to those portions of antibody or immunoglobulin domains that exhibit variability in their sequence and that are involved in determining the specificity and binding affinity of a particular antibody (i.e., the "variable region(s)"). Usually, the pairing of a heavy chain variable region (VH) and a light chain variable region (VL) together forms a single antigen-binding site.

Variability is not evenly distributed throughout the variable regions of antibodies; it is concentrated in sub-domains of each of the heavy and light chain variable regions. These sub-domains are called "hypervariable regions" or "complementarity determining regions" (CDRs). The more conserved (i.e., non-hypervariable) portions of the variable regions are called the "framework" (FR) regions and provide a scaffold for the six CDRs in three-dimensional space to form an antigen-binding surface. The variable regions of naturally occurring antibody heavy and light chains each comprise four FR regions (FR1, FR2, FR3, and FR4), largely adopting a β-sheet configuration. Together with the CDRs, they form the following sequence within a variable heavy or light chain: FR1-CDR1-FR2-CDR2-FR3-CDR3-FR4. The hypervariable regions in each chain are held together in close proximity by the framework regions and, usually together with the hypervariable regions from the other chain, contribute to the formation of the antigen-binding site (see Kabat et al., Sequences of Proteins of Immunological Interest. Bethesda, National Institute of Health. 1991).

The terms "CDR", and its plural "CDRs", refer to the complementarity determining region of which three make up the binding character of a light chain variable region (CDR-L1, CDR-L2 and CDR-L3) and three make up the binding character of a heavy chain variable region (CDR-H1, CDR-H2 and CDR-H3). CDRs contain most of the residues responsible for specific interactions of the antibody (or antibody construct or binding domain) with the antigen and hence contribute to the functional activity of an antibody molecule: they are the main determinants of antigen specificity. The exact definition of CDR boundaries and lengths is subject to different classification and numbering systems. CDRs may therefore be referred to by Kabat, Chothia, contact or any other boundary definitions, including the numbering system described herein. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat (an approach based on cross-species sequence variability), Chothia (an approach based on crystallographic studies of antigen-antibody complexes), and/or MacCallum (Kabat et al., loc. cit.; Chothia et al., J. Mol. Biol, 1987, 196: 901-917; and MacCallum et al., J. Mol. Biol, 1996, 262: 732). Still another standard for characterizing the antigen binding site is the AbM definition used by Oxford Molecular's AbM antibody modeling software. See, e.g., Protein Sequence and Structure Analysis of Antibody Variable Domains. In: Antibody Engineering Lab Manual (Ed.: Duebel, S. and Kontermann, R., Springer-Verlag, Heidelberg). To the extent that two residue identification techniques define regions of overlapping, but not identical regions, they can be combined to define a hybrid CDR. However, the numbering in accordance with the so-called Kabat system is preferred.

Typically, CDRs form a loop structure that can be classified as a canonical structure. The term "canonical structure" refers to the main chain conformation that is adopted by the antigen binding (CDR) loops. From comparative structural studies, it has been found that five of the six antigen binding loops have only a limited repertoire of available conformations. Each canonical structure can be characterized by the torsion angles of the polypeptide backbone. Corresponding loops between antibodies may, therefore, have very similar three-dimensional structures, despite high amino acid sequence variability in most parts of the loops (Chothia and Lesk, J. Mol. Biol., 1987, 196: 901; Chothia et al., Nature, 1989, 342: 877; Martin and Thornton, J. Mol. Biol, 1996, 263: 800). Furthermore, there is a relationship between the adopted loop structure and the amino acid sequences surrounding it. The conformation of a particular canonical class is determined by the length of the loop and the amino acid residues residing at key positions within the loop, as well as within the conserved framework (i.e., outside of the loop). Assignment to a particular canonical class can therefore be made based on the presence of these key amino acid residues.

The term "canonical structure" may also include considerations as to the linear sequence of the antibody, for example, as catalogued by Kabat (Kabat et al.,loc. cit.). The Kabat numbering scheme (system) is a widely adopted standard for numbering the amino acid residues of an antibody variable region in a consistent manner and is the preferred scheme applied in the present invention as also mentioned elsewhere herein. Additional structural considerations can also be used to determine the canonical structure of an antibody. For example, those differences not fully reflected by Kabat numbering can be described by the numbering system of Chothia et al. and/or revealed by other techniques, for example, crystallography and two- or three-dimensional computational modeling. Accordingly, a given antibody sequence may be placed into a canonical class which allows for, among other things, identifying appropriate class sequences (e.g., based on a desire to include a variety of canonical structures in a library). Kabat numbering of antibody amino acid sequences and structural considerations as described by Chothia et al., loc. cit. and their implications for construing canonical aspects of antibody structure, are described in the literature. The subunit structures and three-dimensional configurations of different classes of immunoglobulins are well known in the art. For a review of the antibody structure, see Antibodies: A Laboratory Manual, Cold Spring Harbor Laboratory, eds. Harlow et al., 1988.

The CDR3 of the light chain and, particularly, the CDR3 of the heavy chain may constitute the most important determinants in antigen binding within the light and heavy chain variable regions. In some antibodies, antibody constructs or binding domains, the heavy chain CDR3 appears to constitute the major area of contact between the antigen and the antibody. In vitro selection schemes in which CDR3 alone is varied can be used to vary the binding properties of an antibody or antibody construct/binding domain or determine which residues contribute to the binding of an antigen. Hence, CDR3 is typically the greatest source of molecular diversity within the antibody binding site. CDR-H3, for example, can be as short as two amino acid residues or greater than 26 amino acids.

The sequence of antibody genes after assembly and somatic mutation is highly varied, and these varied genes are estimated to encode $10^{10}$ different antibody molecules (Immunoglobulin Genes, $2^{nd}$ ed., eds. Jonio et al., Academic Press, San Diego, Calif., 1995). Accordingly, the immune system provides a repertoire of immunoglobulins. The term "repertoire" refers to at least one nucleotide sequence derived wholly or partially from at least one sequence encoding at least one immunoglobulin. The sequence(s) may be generated by rearrangement in vivo of the V, D, and J segments of heavy chains, and the V and J segments of light chains. Alternatively, the sequence(s) can be generated from a cell in response to which rearrangement occurs, e.g., in vitro stimulation. Alternatively, part or all of the sequence(s) may be obtained by DNA splicing, nucleotide synthesis, mutagenesis, and other methods, see, e.g., U.S. Pat. No. 5,565,332. A repertoire may include only one sequence or may include a plurality of sequences, including ones in a genetically diverse collection.

The antibodies (and antibody constructs) of the present invention are envisaged to be monoclonal. As used herein, antibodies or antibody constructs that are denominated "monoclonal" (mAb) are obtained from a population of substantially homogeneous antibodies/antibody constructs, i.e., the individual antibodies/antibody constructs comprised in the population are identical (in particular with respect to their amino acid sequence) except for possible naturally occurring mutations and/or post-translational modifications (e.g., isomerizations, amidations) that may be present in minor amounts. Monoclonal antibodies/antibody constructs are highly specific, being directed against a single epitope within the antigen, in contrast to polyclonal antibody preparations which typically include different antibodies directed against different determinants (or epitopes). In addition to their specificity, monoclonal antibodies are advantageous in that they are synthesized by the hybridoma culture, hence uncontaminated by other immunoglobulins. The modifier "monoclonal" indicates the character of the antibody/antibody construct as being obtained from a substantially homogeneous population of antibodies/antibody constructs, and is not to be construed as requiring production of the antibody by any particular method.

For the preparation of monoclonal antibodies, any technique providing antibodies produced by continuous cell line cultures can be used. For example, monoclonal antibodies/antibody constructs to be used may be made by the hybridoma method first described by Koehler et al., Nature, 256: 495 (1975), or may be made by recombinant DNA methods (see, e.g., U.S. Pat. No. 4,816,567). Examples for further techniques to produce human monoclonal antibodies include the trioma technique, the human B-cell hybridoma technique (Kozbor, Immunology Today 4 (1983), 72) and the EBV-hybridoma technique (Cole et al., Monoclonal Antibodies and Cancer Therapy, Alan R. Liss, Inc. (1985), 77-96).

Hybridomas can then be screened using standard methods, such as enzyme-linked immunosorbent assay (ELISA) and surface plasmon resonance (BIACORE™) analysis, to identify one or more hybridomas that produce an antibody/antibody construct that immunospecifically binds to a specified antigen. Any form of the relevant antigen may be used as the immunogen, e.g., recombinant antigen, naturally occurring forms, chimeric antigens, any variants or fragments of the antigen, as well as an antigenic peptide thereof. Surface plasmon resonance as employed in the BIACORE™ system can be used to increase the efficiency of phage antibodies/antibody constructs which bind to an epitope of a target antigen (Schier, Human Antibodies Hybridomas 7 (1996), 97-105; Malmborg, J. Immunol. Methods 183 (1995), 7-13).

Another exemplary method of making antibodies, antibody constructs or binding domains includes screening protein expression libraries, e.g., phage display or ribosome display libraries. Phage display is described, for example, in Ladner et al., U.S. Pat. No. 5,223,409; Smith (1985) Science 228:1315-1317, Clackson et al., Nature, 352: 624-628 (1991) and Marks et al., J. Mol. Biol., 222: 581-597 (1991).

In addition to the use of display libraries, the relevant antigen can be used to immunize a non-human animal, e.g., a rodent (such as a mouse, hamster, rabbit or rat). In one embodiment, the non-human animal includes at least a part of a human immunoglobulin gene. For example, it is possible to engineer mouse strains deficient in mouse antibody production with large fragments of the human Ig (immunoglobulin) loci. Using the hybridoma technology, antigen-specific monoclonal antibodies derived from the genes with the desired specificity may be produced and selected. See, e.g., Xenomouse™, Green et al. (1994) Nature Genetics 7:13-21, US 2003-0070185, WO 96/34096, and WO 96/33735.

A monoclonal antibody can also be obtained from a non-human animal, and then modified, e.g., humanized, deimmunized, rendered chimeric etc., using recombinant DNA techniques known in the art. Examples of modified antibodies, constructs or binding domains include humanized variants of non-human antibodies/antibody constructs, "affinity matured" antibodies, constructs or binding domains (see, e.g. Hawkins et al. J. Mol. Biol. 254, 889-896 (1992) and Lowman et al., Biochemistry 30, 10832-10837 (1991)) and antibody variants or mutants with altered effector function(s) (see, e.g., U.S. Pat. No. 5,648,260, Kontermann and Dübel (2010), loc. cit. and Little (2009), loc. cit.).

In immunology, affinity maturation is the process by which B cells produce antibodies with increased affinity for antigen during the course of an immune response. With repeated exposures to the same antigen, a host will produce antibodies of successively greater affinities. Like the natural prototype, the in vitro affinity maturation is based on the principles of mutation and selection. The in vitro affinity maturation has successfully been used to optimize antibodies, antibody fragments, antibody variants, antibody constructs or binding domains. Random mutations inside the CDRs are introduced using radiation, chemical mutagens or error-prone PCR. In addition, the genetic diversity can be increased by chain shuffling. Two or three rounds of mutation and selection using display methods like phage display usually results in antibodies, antibody fragments, antibody variants, antibody constructs or binding domains with affinities in the low nanomolar range.

Amino acid sequence modifications of the antibodies (or antibody constructs) described herein are also contemplated. For example, it may be desirable to improve the binding affinity and/or other biological properties of the antibody. Amino acid sequence variants of the antibody are prepared by peptide synthesis or by introducing appropriate nucleotide changes into the nucleic acid molecule encoding the antibodies. All below described amino acid sequence modifications should result in antibodies which retain the desired biological activity of the unmodified parental molecule (binding to sBCMA).

The term "amino acid" or "amino acid residue" typically refers to an amino acid having its art recognized definition such as an amino acid selected from the group consisting of: alanine (Ala or A); arginine (Arg or R); asparagine (Asn or N); aspartic acid (Asp or D); cysteine (Cys or C); glutamine (Gln or Q); glutamic acid (Glu or E); glycine (Gly or G); histidine (His or H); isoleucine (Ile or I): leucine (Leu or L); lysine (Lys or K); methionine (Met or M); phenylalanine (Phe or F); proline (Pro or P); serine (Ser or S); threonine (Thr or T); tryptophan (Trp or W); tyrosine (Tyr or Y); and valine (Val or V), although modified, synthetic, or rare amino acids may be used as desired. There are basically four different classes of amino acids determined by different side chains:

(1) non-polar and neutral (uncharged): Ala, Gly, Ile, Leu, Met, Phe, Pro, Val
(2) polar and neutral (uncharged): Asn, Cys (being only slightly polar), Gln, Ser, Thr, Trp (being only slightly polar), Tyr
(3) acidic and polar (negatively charged): Asp and Glu
(4) basic and polar (positively charged): Arg, His, Lys Hydrophobic amino acids can be divided according to whether they have aliphatic or aromatic side chains. Phe and Trp (being very hydrophobic), Tyr and His (being less hydrophobic) are classified as aromatic amino acids. Strictly speaking, aliphatic means that the side chain contains only hydrogen and carbon atoms. By this strict definition, the amino acids with aliphatic side chains are alanine, isoleucine, leucine (also norleucine), proline and valine. Alanine's side chain, being very short, means that it is not particularly hydrophobic, and proline has an unusual geometry that gives it special roles in proteins. It is often convenient to consider methionine in the same category as isoleucine, leucine and valine, although it also contains a sulfur atom. The unifying theme is that these amino acids contain largely non-reactive and flexible side chains. The amino acids alanine, cysteine, glycine, proline, serine and threonine are often grouped together for the reason that they are all small in size. Gly and Pro may influence chain orientation.

Amino acid modifications include, for example, deletions of residues from, insertions of residues into, and/or substitutions of residues within the amino acid sequences of the monoclonal antibodies (antibody constructs). Any combination of deletion, insertion, and/or substitution is made to arrive at a final monoclonal antibody (antibody construct), provided that the final antibody possesses the desired characteristics, e.g. the biological activity of the unmodified parental molecule (such as binding sBCMA). The amino acid changes may also alter post-translational processes of the antibodies, such as changing the number or position of glycosylation sites.

For example, 1, 2, 3, 4, 5, or 6 amino acids may be inserted, deleted and/or substituted in each of the CDRs (of course, dependent on their respective length), while 1, 2, 3, 4, 5, 6, 7, 8, 9, 10, 11, 12, 13, 14, 15, 16, 17, 18, 19, 20, or 25 amino acids may be inserted, deleted and/or substituted in each of the FRs Amino acid sequence insertions also include N-terminal and/or C-terminal additions of amino acids ranging in length from e.g. 1, 2, 3, 4, 5, 6, 7, 8, 9 or 10 residues to polypeptides containing more than 10, e.g. one hundred or more residues, as well as intra-sequence insertions of single or multiple amino acid residues.

The sites of greatest interest for amino acid modifications, in particular for amino acid substitutions, include the hypervariable regions, in particular the individual CDRs of the heavy and/or light chain, but FR alterations in the heavy and/or light chain are also contemplated herein. The substitutions can be conservative substitutions as described herein. Preferably, 1, 2, 3, 4, 5, 6, 7, 8, 9, or 10 amino acids may be substituted in a CDR, while 1, 2, 3, 4, 5, 6, 7, 8, 9, 10, 11, 12, 13, 14, 15, 16, 17, 18, 19, 20, or 25 amino acids may be substituted in the framework regions (FRs), depending on the length of the CDR or FR, respectively. For example, if a CDR sequence encompasses 6 amino acids, it is envisaged that one, two or three of these amino acids are substituted. Similarly, if a CDR sequence encompasses 15 amino acids it is envisaged that one, two, three, four, five or six of these amino acids are substituted.

A useful method for the identification of certain residues or regions within the monoclonal antibody (antibody construct) that are preferred locations for mutagenesis is called "alanine scanning mutagenesis" and is described e.g. in Cunningham B. C. and Wells J. A. (Science. 1989 Jun. 2; 244(4908):1081-5). Here, a residue or group of residues within the antibody is/are identified (e.g. charged residues such as Arg, His, Lys, Asp, and Glu) and replaced by a neutral or non-polar amino acid (most preferably alanine or polyalanine) to affect the interaction of the respective amino acid(s) with the epitope of the target protein. Alanine scanning is a technique used to determine the contribution of a specific residue to the stability or function of given protein. Alanine is used because of its non-bulky, chemically inert, methyl functional group that nevertheless mimics the secondary structure preferences that many of the other amino acids possess. Sometimes bulky amino acids such as valine or leucine can be used in cases where conservation of the size of mutated residues is needed. This technique can also be useful to determine whether the side chain of a specific residue plays a significant role in bioactivity. Alanine scanning is usually accomplished by site-directed mutagenesis or randomly by creating a PCR library. Furthermore, computational methods to estimate thermodynamic parameters based on theoretical alanine substitutions have been developed. The data can be tested by IR/NMR Spectroscopy, mathematical methods, bioassays, etc.

Those amino acid locations demonstrating functional sensitivity to the substitutions (as determined e.g. by alanine scanning) can then be refined by introducing further or other variants at, or for, the sites of substitution. Thus, while the site or region for introducing an amino acid sequence variation is predetermined, the nature of the mutation per se needs not to be predetermined. For example, to analyze or optimize the performance of a mutation at a given site, alanine scanning or random mutagenesis may be conducted at a target codon or region, and the expressed monoclonal antibody/antibody construct variants are screened for the optimal combination of desired activity. Techniques for making substitution mutations at predetermined sites in the DNA having a known sequence are well known, for example, M13 primer mutagenesis and PCR mutagenesis. Screening of the mutants is done e.g. using assays of antigen (e.g. sBCMA) binding activity as described herein.

Generally, if amino acids are substituted in one or more or all of the CDRs of the heavy and/or light chain/variable regions, it is envisaged that the then-obtained "substituted" sequence is at least 60% or 65%, more preferably 70% or 75%, even more preferably 80% or 85%, and particularly preferably 90% or 95% identical/homologous/similar to the "original" or "parental" CDR sequence. This means that the degree of identity/homology/similarity between the original and the substituted sequence depends on the length of the CDR. For example, a CDR having 5 amino acids in total and comprising one amino acid substitution is 80% identical to the "original" or "parental" CDR sequence, while a CDR having 10 amino acids in total and comprising one amino acid substitution is 90% identical to the "original" or "parental" CDR sequence. Accordingly, the substituted CDRs of the monoclonal antibody of the invention may have different degrees of identity to their original sequences, e.g., CDRL1 may have 80%, while CDRL3 may have 90% of homology. The same considerations apply to the framework regions and to the entire VH and VL regions.

A "variant CDR" is a CDR with a specific sequence homology, similarity, or identity to the parent CDR of the invention, and shares biological function with the parent CDR, including, but not limited to, at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent CDR. Generally, the amino acid homology, similarity, or identity between individual variant CDRs is at least 60% to the parent sequences depicted herein, and more typically with increasing homologies, similarities or identities of at least 65% or 70%, preferably at least 75% or 80%, more preferably at least 85%, 90%, 91%, 92%, 93%, 94%, and most preferably 95%, 96%, 97%, 98%, 99%, and almost 100%. The same applies to "variant VH" and "variant VL". According to one embodiment, the sequence variations within a "variant VH" and/or a "variant VL" do not extend to the CDRs. The present invention is hence directed to a monoclonal antibody (or antibody construct) as defined herein, comprising VH and VL sequences having a certain sequence homology/identity/similarity (see above) to the specific sequences as defined herein (the "parental" VH and VL), wherein the CDR sequences are 100% identical to the specific CDR sequences as defined herein (the "parental" CDRs).

Preferred substitutions (or replacements) are conservative substitutions. However, any substitution (including non-conservative substitutions or one or more from the "exemplary substitutions" listed in Table 1, below) is envisaged, as long as the monoclonal antibody (antibody construct) retains its capacity to bind to sBCMA, and/or provided its CDRs, FRs, VH and/or VL sequences have a degree of identity to the original or parental sequence of at least 60% or 65%, more preferably at least 70% or 75%, even more preferably at least 80% or 85%, and particularly preferably at least 90% or 95%.

A conservative replacement (also called a conservative mutation or a conservative substitution) is an amino acid replacement that changes a given amino acid to a different amino acid with similar biochemical properties (e.g. charge, hydrophobicity, size). Conservative replacements in proteins often have a smaller effect on protein function than non-conservative replacements. Conservative substitutions are shown in Table 1. Exemplary conservative substitutions are shown as "exemplary substitutions". If such substitutions result in a change in biological activity, then more substantial changes, as further described herein in reference to amino acid classes, may be introduced and the products screened for a desired characteristic.

TABLE 1

Amino acid substitutions (aa = amino acid)

| Original aa | Conservative substitutions | Exemplary Substitutions |
|---|---|---|
| Ala (A) | Small aa | Gly, Ser, Thr |
| Arg (R) | Polar aa, in particular Lys | Lys, Gln, Asn |
| Asn (N) | Polar aa, in particular Asp | Asp, Gln, His, Lys, Arg |
| Asp (D) | Glu or other polar aa, in particular Asn | Glu, Asn |
| Cys (C) | Small aa | Ser, Ala |
| Gln (Q) | Polar aa, in particular Glu | Glu, Asn |
| Glu (E) | Asp or other polar aa, in particular Gln | Asp, Gln |
| Gly (G) | Small aa, such as Ala | Ala |
| His (H) | | Asn, Gln, Arg, Lys, Tyr |
| Ile (I) | Hydrophobic, in particular aliphatic aa | Ala, Val, Met, Leu, Phe |
| Leu (L) | Hydrophobic, in particular aliphatic aa | Norleucine, Ile, Ala, Val, Met |
| Lys (K) | Polar aa, in particular Arg | Arg, Gln, Asn |
| Met (M) | Hydrophobic, in particular aliphatic aa | Leu, Ala, Ile, Val, Phe |
| Phe (F) | Aromatic or hydrophobic aa, in particular Tyr | Tyr, Trp, Leu, Val, Ile, Ala |
| Pro (P) | Small aa | Ala |
| Ser (S) | Polar or small aa, in particular Thr | Thr |
| Thr (T) | Polar aa, in particular Ser | Ser |
| Trp (W) | Aromatic aa | Tyr, Phe |
| Tyr (Y) | Aromatic aa, in particular Phe | Phe, Trp, Thr, Ser |
| Val (V) | Hydrophobic, in particular aliphatic aa | Leu, Ile, Ala, Met, Phe |

Substantial modifications in the biological properties of the monoclonal antibody (antibody construct) of the present invention are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Non-conservative substitutions will usually entail exchanging a member of one of the above defined amino acid classes (such as polar, neutral, acidic, basic, aliphatic, aromatic, small . . . ) for another class. Any cysteine residue not involved in maintaining the proper conformation of the antibody may be substituted, generally with serine, to improve the oxidative stability of the antibody.

Sequence identity, homology and/or similarity of amino acid sequences is determined by using standard techniques known in the art, including, but not limited to, the local sequence identity algorithm of Smith and Waterman, 1981, Adv. Appl. Math. 2:482, the sequence identity alignment algorithm of Needleman and Wunsch (J Mol Biol. 1970 March; 48(3):443-53), the search for similarity method of Pearson and Lipman (Proc Natl Acad Sci USA. 1988 April; 85(8):2444-8), computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al. (Nucleic Acids Res.1984 Jan. 11; 12(1 Pt 1):387-95), preferably using the default settings, or by inspection. It is envisaged that percent identity is calculated by FastDB based upon the following parameters: mismatch penalty of 1; gap penalty of 1; gap size penalty of 0.33; and joining penalty of 30. See also "Current Methods in Sequence Comparison and Analysis," Macromolecule Sequencing and Synthesis, Selected Methods and Applications, pp 127-149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng and Doolittle (J Mol Evol. 1987; 25(4):351-60); the method is similar to that described by Higgins and Sharp (Comput Appl Biosci. 1989 April; 5(2):151-3). Useful PILEUP parameters include a default gap weight of 3.00, a default gap length weight of 0.10, and weighted end gaps.

Another example of a useful algorithm is the BLAST algorithm, described in: Altschul et al. (J Mol Biol. 1990 Oct. 5; 215(3):403-10.); Altschul et al., (Nucleic Acids Res. 1997 Sep 1; 25(17):3389-402); and Karlin and Altschul (Proc Natl Acad Sci USA. 1993 Jun. 15; 90(12):5873-7). A particularly useful BLAST program is the WU-Blast-2 program which was obtained from Altschul et al., (Methods Enzymol. 1996; 266:460-80). WU-Blast-2 uses several search parameters, most of which are set to the default values. The adjustable parameters are set with the following values: overlap span=1, overlap fraction=0.125, word threshold (T)=II. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al. (Nucleic Acids Res. 1997 Sep. 1; 25(17):3389-402). Gapped BLAST uses BLOSUM-62 substitution scores; threshold T parameter set to 9; the two-hit method to trigger ungapped extensions, charges gap lengths of k a cost of 10+k; Xu set to 16, and Xg set to 40 for database search stage and to 67 for the output stage of the algorithms. Gapped alignments are triggered by a score corresponding to about 22 bits.

In line herewith, the term "percent (%) nucleic acid sequence identity/homology/similarity" with respect to the nucleic acid sequence encoding the monoclonal antibodies (antibody constructs) identified herein is defined as the percentage of nucleotide residues in a candidate sequence that are identical with the nucleotide residues in the coding sequence of the antibody. One method to align two sequences and thereby determine their homology uses the BLASTN module of WU-Blast2 set to the default parameters, with overlap span and overlap fraction set to 1 and 0.125, respectively. Generally, the nucleic acid sequence homology, similarity, or identity between the nucleotide sequences encoding individual variant CDRs and the nucleotide sequences depicted herein are at least 60%, and more typically with increasing homologies, similarities or identities of at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99%, and almost 100%. Again, the same applies to nucleic acid sequence encoding the "variant VH" and/or "variant VL".

The term "antibody construct" refers to a molecule in which the structure and/or function is/are based on the structure and/or function of an antibody, e.g., of a full-length immunoglobulin molecule. An antibody construct hence immunospecifically binds to its target or antigen, and/or it comprises the heavy chain variable region (VH) and/or the light chain variable region (VL) of an antibody, or comprises domains derived therefrom. An antibody construct according to the invention comprises the minimum structural requirements of an antibody which allow for immunospecific target binding. This minimum requirement may e.g. be defined by the presence of at least three light chain CDRs (i.e. CDR1, CDR2 and CDR3 of the VL region) and/or three heavy chain CDRs (i.e. CDR1, CDR2 and CDR3 of the VH region), preferably of all six CDRs. An antibody construct may hence be characterized by the presence of three or six CDRs in a binding domain, and the skilled person knows where (in which order) those CDRs are located within the binding domain.

The term "antibody construct" according to the present invention may also comprise fragments of full-length antibodies, such as VH, VHH, VL, (s)dAb, Fv, light chain (VL-CL), Fd (VH-CH1), heavy chain, Fab, Fab', F(ab')$_2$ or "r IgG" ("half antibody" consisting of a heavy chain and a light chain). An antibody fragment may be produced by enzymatic or chemical cleavage of intact antibodies. Antibody constructs according to the invention may also comprise modified fragments of antibodies, also called antibody variants or antibody derivatives. Examples include, but are not limited to, scFv, di-scFv or bi(s)-scFv, scFv-Fc, scFv-zipper, scFab, Fab$_2$, Fab$_3$, diabodies, single chain diabodies, tandem diabodies (Tandab's), tandem di-scFv, tandem tri-scFv, "minibodies" exemplified by a structure which is as follows: (VH-VL-CH3)$_2$, (scFv-CH3)$_2$, ((scFv)$_2$-CH3+CH3), ((scFv)$_2$-CH3) or (scFv-CH3-scFv)2, multibodies such as triabodies or tetrabodies, and single domain antibodies such as nanobodies or single variable domain antibodies comprising merely one variable region, which might be VHH, VH or VL, that specifically binds to an antigen or target independently of other variable regions or domains. Further possible formats of the antibody constructs according to the invention are cross bodies, maxi bodies, hetero Fc constructs, mono Fc constructs and scFc constructs. Examples for those formats will be described herein below.

Furthermore, the definition of the term "antibody construct" includes bivalent and polyvalent/multivalent constructs as well as bispecific and polyspecific/multispecific constructs, which specifically bind to two, three or more antigenic structures, through distinct binding domains. An antibody construct can have more binding valences than specificities, e.g. in a case where it has two binding domains for one target and one binding domain for another target (such as CD3), or vice versa, in which case the construct is trivalent and bispecific. In general, the term "bispecific" includes the meaning that an antibody construct binds to (at least) two different antigens.

Moreover, the definition of the term "antibody construct" includes molecules consisting of only one polypeptide chain as well as molecules consisting of two, three, four or more polypeptide chains, which chains can be either identical (homodimers, homotrimers or homo oligomers) or different (heterodimer, heterotrimer or heterooligomer). Examples for the above identified antibodies and their fragments, variants, derivatives and antibody constructs derived therefrom are described inter alia in Harlow and Lane, Antibodies: A laboratory manual, CSHL Press (1988); Kontermann and Dübel, Antibody Engineering, Springer, 2nd ed. 2010; and Little, Recombinant Antibodies for Immunotherapy, Cambridge University Press 2009.

The term "binding domain" or "domain which binds to . . . " characterizes in connection with the present invention a domain of the antibody/antibody construct which immunospecifically binds to/interacts with/recognizes an epitope on the target or antigen (here: sBCMA). The structure and function of a binding domain is/are based on the structure and/or function of an antibody, e.g. of a full-length immunoglobulin molecule. The "binding domain" or "domain which binds to . . . " may hence comprise the minimum structural requirements of an antibody which allow for immunospecific target binding. This minimum structural requirement of a binding domain may e.g. be defined by the presence of at least three light chain CDRs (i.e. CDR1, CDR2 and CDR3 of the VL region) and/or of three heavy chain CDRs (i.e. CDR1, CDR2 and CDR3 of the VH region), preferably of all six CDRs. A "domain which binds to" (or a "binding domain") may typically comprise an antibody light chain variable region (VL) and an antibody heavy chain variable region (VH); however, it does not have to comprise both, but may comprise only one of VH or VL. Fd fragments, for example, often retain some antigen-binding function of the intact antigen-binding domain.

Examples for the format of a "domain which binds to" (or a "binding domain") or antibody constructs include, but are not limited to, full-length antibodies, fragments of full-length antibodies (such as VH, VHH, VL), (s)dAb, Fv, light chain (VL-CL), Fd (VH-CH1), heavy chain, Fab, Fab', F(ab')$_2$ or "r IgG" ("half antibody")), antibody variants or derivatives such as scFv, di-scFv or bi(s)-scFv, scFv-Fc, scFv-zipper, scFab, Fab$_2$, Fab$_3$, diabodies, single chain diabodies, tandem diabodies (Tandab's), tandem di-scFv, tandem tri-scFv, "minibodies" (selected from formats such as (VH-VL-CH3)$_2$, (scFv-CH3)$_2$, ((scFv)$_2$-CH3+CH3)), ((scFv)$_2$-CH3) or (scFv-CH3-scFv)$_2$, multibodies such as triabodies or tetrabodies, and single domain antibodies such as nanobodies or single variable domain antibodies comprising merely one variable region, which might be VHH, VH or VL. Further examples for the format of a "domain which binds to" (or a "binding domain") include (1) an antibody fragment or variant comprising VL, VH, CL and CH1 (such as Fab); (2) an antibody fragment or variant comprising two linked Fab fragments (such as a F(ab')$_2$); (3) an antibody fragment or variant comprising VH and CH$_1$ (such as Fd); (4) an antibody fragment or variant comprising VL and CL (such as the light chain); (5) an antibody fragment or variant comprising VL and VH (such as Fv); (5) a dAb fragment (Ward et al., (1989) Nature 341:544-546), which has a VH domain; (6) an antibody variant comprising at least three isolated CDRs of the heavy and/or the light chain; and (7) a single chain Fv (scFv). Examples for embodiments of antibody constructs or binding domains according to the invention are e.g. described in WO 00/006605, WO 2005/040220, WO 2008/119567, WO 2010/037838, WO 2013/026837, WO 2013/026833, US 2014/0308285, US 2014/0302037, WO 2014/144722, WO 2014/151910, and WO 2015/048272.

In an scFv, the VH region and the and VL region are arranged in the order VH-VL or VL-VH (from N- to C-terminus). It is envisaged that the VH and the VL regions are connected via a linker, preferably a peptide linker. According to one embodiment, the VH-region is positioned N-terminally of the linker, and the VL-region is positioned C-terminally of the linker. It is furthermore possible that two scFv domains of an antibody construct are connected via a linker, preferably a peptide linker. The antibody construct may e.g. comprise the domains in the order (from N-terminus to C-terminus) first domain-linker-second domain. The inverse order (second domain-linker-first domain) is also possible.

The linkers are preferably peptide linkers, more preferably short peptide linkers. In accordance with the present invention, a "peptide linker" comprises an amino acid sequence which connects the amino acid sequences of one domain with another (variable and/or binding) domain (e.g. a variable domain or a binding domain) of the antibody construct. An essential technical feature of such peptide linker is that it does not comprise any polymerization activity. Among the suitable peptide linkers are those described in U.S. Pat. Nos. 4,751,180 and 4,935,233 or WO 88/09344. The peptide linkers can also be used to attach other domains or modules or regions (such as half-life extending domains) to the antibody/antibody construct of the invention. In the present context, a "short" linker has between 2 and 50 amino acids, preferably between 3 and 35, between 4 and 30, between 5 and 25, between 6 and 20 or between 6 and 17 amino acids. The linker between two variable regions of one binding domain may have a different length (e.g. may be longer) than the linker between the two binding domains. For example, the linker between two variable regions of one binding domain may have a length between 7 and 15 amino acids, preferably between 9 and 13, and the linker between the two binding domains may have a length between 3 and 10 amino acids, preferably between 4 and 8. It is further envisaged that the peptide linkers are glycine/serine linkers. The majority of the amino acids in glycine/serine linkers are selected from glycine and serine.

In the event that a linker is used to connect two binding domains with different binding specificities, this linker is preferably of a length and sequence sufficient to ensure that each of the domains can, independently from one another, retain their differential binding specificities. For peptide linkers which connect at least two binding domains (or two variable regions forming one binding domain) in an antibody construct, those peptide linkers are envisaged which comprise only a few number of amino acid residues, e.g. 12 amino acid residues or less. Thus, peptide linkers of 12, 11, 10, 9, 8, 7, 6 or 5 amino acid residues are preferred. An envisaged peptide linker with less than 5 amino acids comprises 4, 3, 2 or one amino acid(s), wherein Gly-rich linkers are preferred. A "single amino acid" linker in the context of said "peptide linker" is Gly. Another embodiment of a peptide linker is characterized by the amino acid sequence Gly$_4$Ser, or polymers thereof, i.e. (Gly$_4$Ser)x, where x is an integer of 1 or greater (e.g. 2 or 3). The characteristics of said peptide linkers are known in the art and are described e.g. in Dall'Acqua et al. (Biochem. (1998) 37, 9266-9273), Cheadle et al. (Mol Immunol (1992) 29, 21-30) and Raag and Whitlow (FASEB (1995) 9(1), 73-80). Peptide linkers which do not promote any secondary structures are preferred. The linkage of said domains to each other can be provided, e.g., by genetic engineering. Methods for preparing fused and operatively linked bispecific single chain constructs and expressing them in mammalian cells or bacteria are well-known in the art (e.g. WO 99/54440 or Sambrook et al., Molecular Cloning: A Laboratory Manual, Cold Spring Harbor Laboratory Press, Cold Spring Harbor, N.Y., 2001).

According to one embodiment of the invention, an antibody construct of the invention which binds to sBCMA may be a "single chain antibody construct". Although the two domains of the Fv fragment, VL and VH, are coded for by separate genes, they can be joined, using recombinant methods, by an artificial linker—as described hereinbefore—that enables them to be made as a single protein chain in which the VL and VH regions pair to form a monovalent molecule; see e.g., Huston et al. (1988) Proc. Natl. Acad. Sci USA 85:5879-5883). These antibody fragments are obtained using conventional techniques known to those with skill in the art, and the fragments are evaluated for function in the same manner as are full-length antibodies or IgGs. A single-chain variable fragment (scFv) is hence a fusion protein of the variable region of the heavy chain (VH) and of the light chain (VL) of immunoglobulins, usually connected with a short linker peptide. The linker is usually rich in glycine for flexibility, as well as serine or also threonine for solubility, and can either connect the N-terminus of the VH with the C-terminus of the VL, or vice versa. This protein retains the specificity of the original immunoglobulin, despite removal of the constant regions and introduction of the linker.

Antibody constructs denominated "single domain antibodies" comprise one (monomeric) antibody variable region which is able to bind selectively to a specific antigen, independently of other variable regions. The first single domain antibodies were engineered from heavy chain antibodies found in camelids, and these are called V$_H$H fragments. Cartilaginous fishes also have heavy chain antibodies (IgNAR) from which single domain antibodies called V$_{NAR}$ fragments can be obtained. An alternative approach is to split the dimeric variable regions from common immunoglobulins into monomers, hence obtaining VH or VL as a single domain Ab. Although most research into single domain antibodies is currently based on heavy chain variable regions, nanobodies derived from light chains were also shown to bind specifically to target epitopes. Examples of single domain antibodies are called sdAb, nanobodies or single variable domain antibodies. A (single domain mAb)$_2$ is hence a monoclonal antibody construct composed of (at least) two single domain monoclonal antibody constructs, which are individually selected from the group comprising VH, VL, V$_H$H and V$_{NAR}$. The linker is preferably in the form of a peptide linker. Similarly, an "scFv-single domain mAb" is a monoclonal antibody construct composed of at least one single domain antibody as described above and one scFv molecule as described above. Again, the linker is preferably in the form of a peptide linker.

According to one embodiment, the antibody or antibody construct which binds to sBCMA is in the form of one or more polypeptides or in the form of proteins. In addition to proteinaceous parts, such polypeptides or proteins may include non-proteinaceous parts (e.g. chemical linkers or chemical cross-linking agents such as glutaraldehyde).

Peptides are short chains of amino acid monomers linked by covalent peptide (amide) bonds. Hence, peptides fall under the broad chemical classes of biological oligomers and polymers Amino acids that are part of a peptide or polypeptide chain are termed "residues" and can be consecutively numbered. All peptides except cyclic peptides have an N-terminal residue at one end and a C-terminal residue at the other end of the peptide. An oligopeptide consists of only a few amino acids (usually between two and twenty). A polypeptide is a longer, continuous, and unbranched peptide chain. Peptides are distinguished from proteins on the basis of size, and as an arbitrary benchmark can be understood to contain approximately 50 or fewer amino acids. Proteins consist of one or more polypeptides, usually arranged in a biologically functional way. While aspects of the lab techniques applied to peptides versus polypeptides and proteins differ (e.g., the specifics of electrophoresis, chromatography, etc.), the size boundaries that distinguish peptides from polypeptides and proteins are not absolute. Therefore, in the context of the present invention, the terms "peptide", "polypeptide" and "protein" may be used interchangeably, and the term "polypeptide" is often preferred.

Polypeptides may further form multimers such as dimers, trimers and higher oligomers, which consist of more than one polypeptide molecule. Polypeptide molecules forming such dimers, trimers etc. may be identical or non-identical. The corresponding structures of higher order of such multimers are, consequently, termed homo- or heterodimers, homo- or heterotrimers etc. An example for a hereteromultimer is an antibody or immunoglobulin molecule, which, in its naturally occurring form, consists of two identical light polypeptide chains and two identical heavy polypeptide chains. The terms "peptide", "polypeptide" and "protein" also refer to naturally modified peptides/polypeptides/proteins wherein the modification is accomplished e.g. by post-translational modifications like glycosylation, acetylation, phosphorylation and the like. A "peptide", "polypeptide" or "protein" when referred to herein may also be chemically modified such as pegylated. Such modifications are well known in the art and described herein below.

The terms "(specifically or immunospecifically) binds to", "(specifically or immunospecifically) recognizes", or "(specifically or immunospecifically) reacts with" mean in accordance with this invention that an antibody, antibody construct or a binding domain interacts or (immuno-) specifically interacts with a given epitope on the target molecule (antigen), here: sBCMA. This interaction or association occurs more frequently, more rapidly, with greater duration, with greater affinity, or with some combination of the aforementioned, to an epitope on the specific target than to alternative substances (non-target molecules). Because of the sequence similarity between homologous proteins in different species, an antibody, antibody construct or a binding domain that immunospecifically binds to its target (such as a human target) may, however, cross-react with homologous target molecules from different species (such as, from non-human primates). The term "specific/immunospecific binding" can hence include the binding of an antibody, antibody construct or binding domain to epitopes or structurally related epitopes in more than one species.

In the context of the present invention, the term "epitope" refers to the part or region of the antigen that is recognized/immunospecifically recognized by the binding domain, antibody or antibody construct. An "epitope" is antigenic, and thus the term epitope is sometimes also referred to as "antigenic structure" or "antigenic determinant". The part of the binding domain, antibody or antibody construct that binds to the epitope is called a paratope. Specific binding is believed to be accomplished by specific motifs in the amino acid sequence of the binding domain, antibody or antibody construct and the antigen. Thus, binding is achieved as a result of their primary, secondary and/or tertiary structure as well as the result of potential secondary modifications of said structures. The specific interaction of the paratope with its antigenic determinant may result in a simple binding of said site to the antigen. In some cases, the specific interaction may alternatively or additionally result in the initiation of a signal, e.g. due to the induction of a change of the conformation of the antigen, an oligomerization of the antigen, etc.

The epitopes of protein antigens are divided into two categories, conformational epitopes and linear epitopes, based on their structure and interaction with the paratope. A conformational epitope is composed of discontinuous sections of the antigen's amino acid sequence. These epitopes interact with the paratope based on the three-dimensional surface features and shape or tertiary structure (folding) of the antigen. Methods of determining the conformation of epitopes include, but are not limited to, x-ray crystallography, two-dimensional nuclear magnetic resonance (2D-NMR) spectroscopy and site-directed spin labelling and electron paramagnetic resonance (EPR) spectroscopy. By contrast, linear epitopes interact with the paratope based on their primary structure. A linear epitope is formed by a continuous sequence of amino acids from the antigen and typically includes at least 3 or at least 4, and more usually, at least 5 or at least 6 or at least 7, for example, about 8 to about 10 amino acids in a unique sequence.

A method for BCMA epitope mapping is described in the following: A pre-defined region (usually a contiguous amino acid stretch) within the extracellular domain of the human BCMA protein is exchanged/replaced with a corresponding region of BCMA of another species (such as mouse, but other species are also conceivable, so long as the antibody is not cross-reactive with the species). These human BCMA/mouse (or other species) BCMA chimeras may be expressed on the surface of host cells (such as CHO cells). Binding of the antibody or antibody construct can be tested via FACS analysis. When the binding of the antibody or antibody construct to the chimeric molecule is entirely abolished, or when a significant binding decrease is observed, it can be concluded that the region of human BCMA which was removed from this chimeric molecule is relevant for the immunospecific epitope-paratope recognition. Said decrease in binding is preferably at least 10%, 20%, 30%, 40%, or 50%; more preferably at least 60%, 70%, or 80%, and most preferably 90%, 95% or even 100% in comparison to the binding to human (wild-type) BCMA, whereby binding to human BCMA is set to be 100%. Alternatively, the above described epitope mapping analysis can be modified by introducing one or more point mutations into the sequence of BCMA. These point mutations can e.g. reflect the differences between human BCMA and mouse (or other species) BCMA.

A further method to determine the contribution of a specific residue of a target antigen to the recognition by an antibody, antibody construct or binding domain is alanine scanning (see e.g. Morrison K L & Weiss G A. Curr Opin Chem Biol. 2001 Jun.; 5(3):302-7), where each residue to be analyzed is replaced by alanine, e.g. via site-directed mutagenesis. Alanine is used because of its non-bulky, chemically inert, methyl functional group that nevertheless mimics the secondary structure references that many of the other amino acids possess. Sometimes bulky amino acids such as valine or leucine can be used in cases where conservation of the size of mutated residues is desired.

The interaction between the monoclonal antibody (or antibody construct) and the epitope of the target antigen implies that the variable regions exhibit appreciable or significant affinity for the epitope/the target antigen (here: sBCMA) and, generally, does not exhibit significant affinity for proteins or antigens other than the target antigen (here: sBCMA)— notwithstanding the above discussed cross-reactivity with homologous targets e.g. from other species. "Significant affinity" includes binding with an affinity (dissociation constant, KD) of about ≤$10^{-6}$ M. Preferably, binding is considered specific when the binding affinity is about ≤$10^{-7}$ M, ≤$10^{-8}$ M, ≤$10^{-9}$ M, or ≤$10^{-10}$ M. It is hence envisaged that the monoclonal antibodies (or antibody constructs) of the present invention have an affinity (KD) to sBCMA of about ≤10-7 M, ≤10-8 M, ≤10-9 M, or ≤10-10 M. These values are preferably measured in a surface plasmon resonance assay, such as a surface plasmon resonance (BIACORE™)assay. See Example 3.

Whether a monoclonal antibody (or antibody construct) (immuno-)specifically reacts with or binds to a target can be tested readily e.g. by comparing the affinity of said antibody to its desired target protein or antigen with the affinity of said antibody to non-target proteins or antigens (here: proteins other than sBCMA). Preferably, a monoclonal antibody (or antibody construct) of the invention does not significantly bind to proteins or antigens other than sBCMA—unless any further binding domain(s) directed against a further target is/are deliberately introduced into the antibody/antibody construct of the invention. The term "does not significantly bind" means that a monoclonal antibody (or antibody construct) of the present invention does not bind to a protein or antigen other than sBCMA. The antibody construct hence shows reactivity of ≤30%, preferably ≤20%, more preferably ≤10%, particularly preferably ≤9%, ≤8%, ≤7%, ≤6%, ≤5%, ≤4%, ≤3%, ≤2%, or ≤1% with proteins or antigens other than sBCMA, whereby binding to sBCMA is set to be 100%. The "reactivity" can e.g. be expressed in an affinity value (see above). It is envisaged that the monoclonal antibody (or antibody construct) of the invention does not bind to or does not significantly bind to, interact with, recognize, immunospecifically bind to or cross-react with human BAFF-R and/or human TACI.

The monoclonal antibody (or antibody construct) of the present invention may be an "in vitro generated antibody/antibody construct" and/or a "recombinant antibody/antibody construct". In the context of the present invention, the term "in vitro generated" refers to an antibody/antibody construct according to the above definition where all or part of the variable region (e.g., at least one CDR) is generated in a non-immune cell selection, e.g., in an in vitro phage display, on a protein chip or in any other method in which candidate amino acid sequences can be tested for their ability to bind to an antigen. This term thus preferably excludes sequences generated solely by genomic rearrangement in an immune cell in an animal It is envisaged that the antibody (or antibody construct) is produced by or obtainable by phage display or library screening methods or by grafting CDR sequences from a pre-existing (monoclonal) antibody into a scaffold. A "recombinant antibody/antibody construct" is an antibody/antibody construct generated or produced using (inter alia) recombinant DNA technology or genetic engineering.

A preferred type of an amino acid substitutional variation of the monoclonal antibody (or antibody construct) of the invention involves substituting one or more residues within the hypervariable region of a parent antibody structure. Generally, the resulting variant(s) selected for further development will have improved biological properties relative to the parent antibody structure from which they are generated. A convenient way for generating such substitutional variants involves affinity maturation using phage display. Briefly, several sites of the hypervariable region (e. g. 6-7 sites) are mutated to generate all possible amino acid substitutions at each site. The variants thus generated are displayed in a monovalent fashion from filamentous phage particles as fusions to the gene III product of M13 packaged within each particle. The phage-displayed variants are then screened for their biological activity (e.g. binding affinity) as disclosed herein. To identify candidate hypervariable region sites contributing significantly to antigen binding (candidates for modification), alanine scanning mutagenesis can also be performed. Alternatively, or additionally, it may be beneficial to analyze a crystal structure of the complex between the antigen and the antibody/antibody construct or the binding domain to identify contact points between the antibody/antibody construct binding domain and its specific antigen. Such contact residues and neighboring residues are candidates for substitution according to the techniques elaborated herein. Once such variants are generated, the panel of variants is subjected to screening as described herein and antibodies, their antigen-binding fragments, antibody constructs or binding domains with superior properties in one or more relevant assays may be selected for further development.

The monoclonal antibodies (or antibody constructs) of the present invention specifically include "chimeric" versions in which a portion of the heavy and/or light chain is identical with or homologous to corresponding sequences in antibodies derived from a particular species or belonging to a particular antibody class or subclass, while the remainder of the chain(s) is/are identical with or homologous to corresponding sequences in antibodies derived from another species or belonging to another antibody class or subclass, as well as fragments or variants of such antibodies, so long as they exhibit the desired biological activity (U.S. Pat. No. 4,816,567; Morrison et al., Proc. Natl. Acad. Sci. USA, 81: 6851-6855 (1984)). Chimeric antibodies, antibody constructs or binding domains of interest herein include "primitized" antibodies comprising e.g. variable domain antigen-binding sequences derived from a non-human primate (e.g., Old World Monkey, Ape etc.) and human constant region sequences. A variety of approaches for making chimeric antibodies or antibody constructs have been described. See e.g., Morrison et al., Proc. Natl. Acad. ScL U.S.A. 81:6851, 1985; Takeda et al., Nature 314:452, 1985, Cabilly et al., U.S. Pat. No. 4,816,567; Boss et al., U.S. Pat. No. 4,816,397; Tanaguchi et al., EP 0171496; EP 0173494; and GB 2177096.

"Humanized" monoclonal antibodies, variants or fragments thereof, antibody constructs and binding domains are based on immunoglobulins of mostly human sequences, which contain (a) minimal sequence(s) derived from non-human immunoglobulin. For the most part, humanized antibodies, variants or fragments thereof, antibody constructs and binding domains are based on human immunoglobulins (recipient antibodies) in which residues from a hypervariable region or CDR are replaced by residues from a hypervariable region or CDR of a non-human species (donor antibody) such as a rodent (e.g. mouse, hamster, rat or rabbit) having the desired specificity, affinity, capacity and/or biological activity. In some instances, Fv framework region (FR) residues of the human immunoglobulin are replaced by corresponding non-human residues. Furthermore, "humanized" antibodies, variants or fragments thereof, antibody constructs and binding domains as used herein may also comprise residues which are found neither in the recipient antibody nor the donor antibody. These modifications are made to further refine and optimize antibody performance. The humanized antibodies, variants or fragments thereof, antibody constructs and binding domains may also comprise at least a portion of an immunoglobulin constant region (such as Fc), typically that of a human immunoglobulin. For further details, see Jones et al., Nature, 321: 522-525 (1986); Reichmann et al., Nature, 332: 323-329 (1988); and Presta, Curr. Op. Struct. Biol., 2: 593-596 (1992).

Humanized antibodies, variants or fragments thereof, antibody constructs and binding domains can be generated by replacing sequences of the (Fv) variable region that are not directly involved in antigen binding with equivalent sequences from human (Fv) variable regions. Exemplary methods for generating such molecules are provided by Morrison (1985) Science 229:1202-1207; by Oi et al. (1986) BioTechniques 4:214; and by U.S. Pat. Nos. 5,585,089; 5,693,761; 5,693,762; 5,859,205; and 6,407,213. These methods include isolating, manipulating, and expressing the nucleic acid sequences that encode all or part of immunoglobulin (Fv) variable regions from at least one of a heavy or light chain. Such nucleic acids may be obtained from a hybridoma producing an antibody against a predetermined target, as described above, as well as from other sources. The recombinant DNA encoding the humanized antibody, variant or fragment thereof, antibody construct or binding domain can then be cloned into an appropriate expression vector.

Humanized antibodies, variants or fragments thereof, antibody constructs and binding domains may also be produced using transgenic animals such as mice that express human heavy and light chain genes, but are incapable of expressing the endogenous mouse immunoglobulin heavy and light chain genes. Winter describes an exemplary CDR grafting method that may be used to prepare the humanized molecules described herein (U.S. Pat. No. 5,225,539). All of the CDRs of a particular human sequence may be replaced with at least a portion of a non-human CDR, or only some of the CDRs may be replaced with non-human CDRs. It is only necessary to replace the number of CDRs required for binding of the humanized molecule to a predetermined antigen.

A humanized antibody, variant or fragment thereof, antibody construct or binding domain can be optimized by the introduction of conservative substitutions, consensus sequence substitutions, germline substitutions and/or back mutations. Such altered immunoglobulin molecules can be made by any of several techniques known in the art, (e.g., Teng et al., Proc. Natl. Acad. Sci. U.S.A., 80: 7308-7312, 1983; Kozbor et al., Immunology Today, 4: 7279, 1983; Olsson et al., Meth. Enzymol., 92: 3-16, 1982, and EP 239 400).

According to one embodiment, the monoclonal antibody (or antibody construct), is "rabbit". The term "rabbit antibody", "rabbit antibody construct" and "rabbit binding domain" includes antibodies, antibody constructs and binding domains, respectively, having antibody-derived regions such as variable and constant regions or domains which correspond substantially to rabbit germline immunoglobulin sequences known in the art. The rabbit antibody constructs or binding domains of the invention may include amino acid residues not encoded by rabbit germline immunoglobulin sequences (e.g., mutations introduced by random or site-specific mutagenesis in vitro or by somatic mutation in vivo), for example in the CDRs, and in particular in CDR3. The rabbit antibody antibodies, antibody constructs or binding domains can have at least one, two, three, four, five, or more positions replaced with an amino acid residue that is not encoded by the rabbit germline immunoglobulin sequence. The definition of rabbit antibodies, antibody constructs and binding domains as used herein also contemplates fully rabbit antibodies, antibody constructs and binding domains which include only non-artificially and/or genetically altered rabbit sequences of antibodies.

It is envisaged that the monoclonal antibodies (or antibody constructs) of the invention are "isolated" or "substantially pure" antibodies. "Isolated" or "substantially pure", when used to describe the antibodies described herein, means an antibody that has been identified, separated and/or recovered from a component of its production environment. Preferably, the antibody is free or substantially free of association with all other components from its production environment. Contaminant components of its production environment, such as that resulting from recombinant transfected cells, are materials that could interfere e.g. with diagnostic uses for the antibody (or antibody construct), and may include enzymes, hormones, and other proteinaceous or non-proteinaceous compounds. It is understood that the isolated or substantially pure antibody (or antibody construct) may constitute from 5% to 99.9% by weight of the total protein/polypeptide content in a given sample, depending on the circumstances. The desired antibody (or antibody construct) may be produced at a significantly higher concentration through the use of an inducible promoter or high expression promoter. The definition includes the production of an antibody (or antibody construct) in a wide variety of organisms and/or host cells that are known in the art. In certain embodiments, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver staining. Usually, however, an isolated antibody or antibody construct will be prepared by at least one purification step.

The monoclonal antibodies (or antibody constructs) of the present invention bind to soluble BCMA (sBCMA). "Soluble BCMA" is a cleaved fragment of membrane-bound BCMA. Cleavage occurs e.g. via secretases, and shed BCMA (sBCMA) is released from the cell surface. Soluble BCMA levels are usually increased in MM patients versus healthy individuals, but also in patients with other diseases. Furthermore, the sBCMA level in patient serum may be correlated with disease status and prognosis. The level of sBCMA can also be markedly decreased after successful therapy of a disease associated with BCMA overexpression or increased sBCMA levels. It is envisaged that the sBCMA is human sBCMA. The amino acid sequence of the entire (membrane-bound) human BCMA molecule (B cell maturation antigen, TNFRSF17, CD269) is shown in SEQ ID NO: 33, and the amino acid sequence of the extracellular domain of human BCMA is shown in SEQ ID NO: 34. This sequence also corresponds to the shed or soluble BCMA. In other words, sBCMA is envisaged to have the amino acid sequence as depicted in SEQ ID NO: 34.

The term "binding occurs in the presence of" means, in the context of the present invention, that there is simultaneous binding of two (or more) antibodies (or antibody constructs) to the same target (here: sBCMA). In other words, two (or more) antibodies (or antibody constructs) do not compete or do not significantly compete (with each other) for binding to the target (here: sBCMA). According to one embodiment, this could also mean that one monoclonal antibody (or antibody construct) binds to an sBCMA epitope that is different from the sBCMA epitope of a second monoclonal antibody or antibody construct (or in addition of a third antibody or antibody construct, see below).

According to one aspect of the present invention, the binding of the monoclonal antibody (or antibody construct) to sBCMA occurs—in addition to occurring in the presence of a second monoclonal antibody (or antibody construct) binding to sBCMA—in the presence of a third antibody or antibody construct binding to sBCMA. This third antibody or antibody construct may be a therapeutic antibody or antibody construct binding to the extracellular domain of BCMA.

In one embodiment of the present invention, the third antibody or antibody construct binds to epitope cluster 3 of BCMA. More preferably, it binds to epitope cluster 3 of human BCMA. An amino acid sequence for epitope cluster 3 of human BCMA is depicted in SEQ ID NO: 35. Antibody constructs having domains that bind to said epitope cluster 3 of BCMA are described in detail in WO 2013/072406, the content of which is hereby incorporated by reference. These antibody constructs were shown to have a very beneficial epitope/activity relationship. The "third antibody or antibody construct" of the present invention is envisaged to comprise a domain binding to BCMA and comprising a VH region comprising a VH-CDR1, VH-CDR2 and VH-CDR3 and a VL region comprising a VL-CDR1, VL-CDR2 and VL-CDR3 as claimed in WO 2013/072406. It is furthermore envisaged to comprise a domain binding to BCMA and comprising a VH region and/or a VL region as disclosed in the claims of WO 2013/072406. It is also envisaged to comprise a domain binding to BCMA and a domain binding to CD3 (such as human CD3, preferably CD3-epsilon or human CD3-epsilon), as disclosed and claimed in WO 2013/072406. It is also envisaged to bind to the same sBCMA epitope as the antibodies defined and claimed in WO 2013/072406, or compete for binding to sBCMA with the antibodies defined and claimed in WO 2013/072406.

Antibodies (or bispecific antibody constructs) directed against (human) CD3 or specifically against CD3 epsilon are known in the art, and their CDRs, VH and VL sequences can serve as a basis for a second binding domain of the "first", "second" or "third" antibody/antibody construct of the invention. For example, Kung et al. reported in 1979 the development of OKT3 (Ortho Kung T3), the first mAb recognizing CD3 (specifically, the epsilon chain of CD3) on human T cells. OKT3 (muromonab) was the first monoclonal antibody of murine origin to become available for therapy in humans. Newer anti-CD3 monoclonal antibodies include otelixizumab (TRX4), teplizumab (MGA031), foralumab and visilizumab, all targeting the epsilon chain of CD3. Bispecific antibody constructs directed against a (cancer) target and CD3 are also being developed and (pre-) clinically tested, and their CD3 binding domain (CDRs, VH, VL) may serve as a basis for a second binding domain of the first, second or third antibody/antibody construct of the invention. Examples include, but are not limited to, Blinatumomab, Solitomab (MT110, AMG 110), Catumaxomab, Duvortuxizumab, Ertumaxomab, Mosunetuzumab, FBTA05 (Bi20, TPBs05), CEA-TCB (RG7802, RO6958688), AFM11, and MGD006 (S80880). Other examples of CD3 binding domains are disclosed e.g. in U.S. Pat. Nos. 7,994,289 B2, 7,728,114 B2, 7,381,803 B1, 6,706,265 B1.

The third antibody construct of the present invention is furthermore envisaged to comprise a domain binding to BCMA as described herein, a domain binding to CD3 as described herein, and a domain which provides for a half-life extension of the antibody construct. This latter domain may comprise two polypeptide monomers, each comprising a hinge, a CH2 domain and a CH3 domain, wherein said two polypeptide monomers are fused to each other via a peptide linker. Such antibody constructs and HLE domains are described in detail in WO 2017/134134, the content of which is enclosed herein by reference.

In a further embodiment, the "third antibody or antibody construct" is an antibody/antibody construct disclosed in WO 2014/089335 as having the following amino acid sequences: VH-CDRs (SEQ ID NOs: 4-6), VL-CDRs (SEQ ID NOs: 106-108), VH (SEQ ID NO: 206), VL (SEQ ID NO: 240) of WO 2014/089335. The third antibody or antibody construct may hence comprise a VH region comprising a VH-CDR1 as depicted in SEQ ID NO: 4, a VH-CDR2 as depicted in SEQ ID NO: 5, and a VH-CDR3 as depicted in SEQ ID NO: 6 of WO 2014/089335, and a VL region comprising a VL-CDR1 as depicted in SEQ ID NO: 107, a VL-CDR2 as depicted in SEQ ID NO: 107, and a VL-CDR3 as depicted in SEQ ID NO: 108 of WO 2014/089335. It may also comprise a VH region as depicted in SEQ ID NO: 206 of WO 2014/089335, or a VL region as depicted in SEQ ID NO: 240 of WO 2014/089335. The third antibody or antibody construct may also bind to the same sBCMA epitope as the antibody defined herein above, or compete for binding to sBCMA with the antibody defined herein above (i.e. the antibody having the sequences cited from WO 2014/089335).

The monoclonal antibody/antibody construct of the present invention is envisaged to comprise (a) a rabbit VH region, (b) a rabbit VL region or (c) a rabbit VH region and a rabbit VL region. Furthermore, the entire monoclonal antibody can be a rabbit antibody. The variable regions or the antibody/antibody construct itself are hence derived from rabbit. The term "rabbit antibody", "rabbit antibody construct", "rabbit binding domain" and "rabbit VH/VL region" includes antibodies, antibody constructs, binding domains and VH/VL regions, respectively, comprising antibody-derived regions such as variable and constant regions or domains which correspond substantially to rabbit germline immunoglobulin sequences known in the art. The rabbit antibodies, antibody constructs or binding domains of the invention may include amino acid residues not encoded by rabbit germline immunoglobulin sequences (e.g., mutations introduced by random or site-specific mutagenesis in vitro or by somatic mutation in vivo), for example in the CDRs, and in particular in CDR3. The definition of rabbit antibodies, antibody constructs and binding domains as used herein also contemplates fully rabbit antibodies, antibody constructs, VH/VL regions and binding domains which include only non-artificially and/or genetically altered rabbit sequences of antibodies. They may e.g. be obtained by immunization campaigns with rabbits, using standard techniques known in the art. The monoclonal antibody of the invention may also comprise a rabbit VH region and/or a rabbit VL region and antibody constant regions, which are e.g. rabbit constant regions (such as the exemplary rabbit heavy chain constant region of SEQ ID NO: 31 or the exemplary rabbit light chain constant region of SEQ ID NO: 32), or constant regions from other species (human, mouse, rat, hamster, goat, etc.), depending on the requirements and the design of the sBCMA detection system.

According to one embodiment of the present invention, the monoclonal antibody or antibody construct comprises:

a) a VH region comprising a VH-CDR1 as depicted in SEQ ID NO: 1, a VH-CDR2 as depicted in SEQ ID NO: 2, and a VH-CDR3 as depicted in SEQ ID NO: 3, and a VL region comprising a VL-CDR1 as depicted in SEQ ID NO: 4, a VL-CDR2 as depicted in SEQ ID NO: 5, and a VL-CDR3 as depicted in SEQ ID NO: 6;

b) a VH region comprising a VH-CDR1 as depicted in SEQ ID NO: 11, a VH-CDR2 as depicted in SEQ ID NO: 12, and a VH-CDR3 as depicted in SEQ ID NO: 13, and a VL region comprising a VL-CDR1 as depicted in SEQ ID NO: 14, a VL-CDR2 as depicted in SEQ ID NO: 15, and a VL-CDR3 as depicted in SEQ ID NO: 16; or c) a VH region comprising a VH-CDR1 as depicted in SEQ ID NO: 21, a VH-CDR2 as depicted in SEQ ID NO: 22, and a VH-CDR3 as depicted in SEQ ID NO: 23, and a VL region comprising a VL-CDR1 as depicted in SEQ ID NO: 24, a VL-CDR2 as depicted in SEQ ID NO: 25, and a VL-CDR3 as depicted in SEQ ID NO: 26.

It is furthermore envisaged that the monoclonal antibody of the present invention binds to the same sBCMA epitope as the antibody of a), of b), or of c) above, or competes for binding to sBCMA with the antibody of a), of b), or of c) above.

Whether or not an antibody, antibody construct or binding domain binds to the same epitope of sBCMA (or of the extracellular domain of BCMA) as another given antibody, antibody construct or binding domain can be measured by different analyses, e.g. by epitope mapping with chimeric or mutated BCMA molecules, as described e.g. in WO 2013/072406. Other methods of determining epitopes are described herein, such as alanine scanning (see e.g. Morrison KL & Weiss GA. Curr Opin Chem Biol. 2001 Jun.; 5(3):302-7), where each residue within the target amino acid sequence to be analyzed is replaced by alanine, e.g. via site-directed mutagenesis. Alanine is used because of its non-bulky, chemically inert, methyl functional group that nevertheless mimics the secondary structure references that many of the other amino acids possess. Sometimes bulky amino acids such as valine or leucine can be used in cases where conservation of the size of mutated residues is desired. This method where systematic mutations of amino acids are introduced into the sequence of the target protein, and binding of an antibody to each mutated protein is tested to identify the amino acids that comprise the epitope, is also called "site-directed mutagenesis". Other methods available for mapping antibody epitopes on target antigens are high-throughput shotgun mutagenesis epitope mapping, cross-linking-coupled mass spectrometry, X-ray co-crystallography, cryogenic electron microscopy, and hydrogen-deuterium exchange.

Whether or not an antibody or antibody construct competes for binding to an antigen (such as BCMA or sBCMA) with another given antibody or antibody construct can be measured in a competition assay such as a competitive ELISA. Avidin-coupled microparticles (beads) can also be used. Similar to an avidin-coated ELISA plate, when reacted with a biotinylated protein, each of these beads can be used as a substrate on which an assay can be performed. Antigen is coated onto a bead and then precoated with the first antibody. The second antibody is added, and any additional binding is determined. Read-out occurs via flow cytometry. A cell-based competition assay may be used, using either cells that naturally express BCMA or cells that were stably or transiently transformed with BCMA. Furthermore, Example 2b) of the present invention describes an Octet competition assay which may also be used to determine competition between two antibodies/antibody constructs for binding to sBCMA. The term "competes for binding", in the present context, means that competition occurs between the two tested antibodies of at least 20%, at least 30%, at least 40%, at least 50%, at least 60%, at least 70%, at least 80% or at least 90%, as determined by any one of the assays disclosed above.

According to one embodiment of the present invention, the monoclonal antibody comprises:

a) a VH region as depicted in any one of SEQ ID NOs: 7, 17 or 27;

b) a VL region as depicted in any one of SEQ ID NOs: 8, 18 or 28;

c) a VH region as depicted in SEQ ID NO: 7 and a VL region as depicted in SEQ ID NO: 8;

d) a VH region as depicted in SEQ ID NO: 17 and a VL region as depicted in SEQ ID NO: 18;

e) a VH region as depicted in SEQ ID NO: 27 and a VL region as depicted in SEQ ID NO: 28; or the monoclonal antibody of the present invention f) binds to the same sBCMA epitope as the antibody of c) or competes for binding to sBCMA with the antibody of c);

g) binds to the same sBCMA epitope as the antibody of d) or competes for binding to sBCMA with the antibody of d); or h) binds to the same sBCMA epitope as the antibody of e) or competes for binding to sBCMA with the antibody of e).

It is envisaged that the monoclonal antibody of the present invention (or the "first monoclonal antibody") and/or the second monoclonal antibody as defined herein bind(s) to sBCMA in a sample. According to one embodiment, this sample may be a biological sample. According to one embodiment, the sample is a human sample, e.g. a human biological sample. The biological sample may be a (human) serum sample, plasma sample, blood sample, bone marrow sample or tissue sample. The sample may also be supernatant obtained from a cell culture of (human) bone marrow mononuclear cells or of (human) peripheral blood mononuclear cells. The sample may be obtained from a subject, e.g. a human subject, suspected of having, or having (being diagnosed with) a disease associated with sBCMA or increased sBCMA, or a subject having received treatment for a disease associated with sBCMA or increased sBCMA.

"Blood" is a body fluid in humans and other animals that delivers necessary substances such as nutrients and oxygen to the cells and transports metabolic waste products away from those same cells. In vertebrates, blood is composed of blood cells suspended in blood plasma. Blood plasma or "plasma" is the liquid component of the blood in which several types of blood cells are suspended. It is mostly water and contains dissolved proteins (such as serum albumins, globulins, fibrinogen, and others), glucose, clotting factors, electrolytes, hormones, carbon dioxide and oxygen. Blood serum or "serum" is plasma without clotting factors. Serum hence includes all plasma proteins not used in coagulation. "Bone marrow" is a semi-solid tissue which may be found within the spongy or cancellous portions of bones. A "tissue" is a cellular organizational level between cells and a complete organ. A tissue is an ensemble of similar cells and their extracellular matrix from the same origin that together carry out a specific function. Organs are then formed by the functional grouping together of multiple tissues.

Covalent modifications of the monoclonal antibody (or antibody construct) of the invention are also included within the scope of this invention, and are generally, but not always, done post-translationally. For example, several types of covalent modifications of the antibody are introduced into the molecule by reacting specific amino acid residues of the antibody with an organic derivatizing agent that is capable of reacting with selected side chains or with the N- or C-terminal residues. Derivatization with bifunctional agents is useful for crosslinking the antibody of the present invention to a water-insoluble support matrix or surface for use in a variety of methods, in particular, detection methods. Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention. Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco, 1983, pp. 79-86), acetylation of the N-terminal amine, and amidation of any C-terminal carboxyl group.

According to the present invention, the monoclonal antibody (or antibody construct), the "first" monoclonal antibody (or antibody construct) and/or the second monoclonal (or antibody construct) antibody is/are coupled to a detectable label. In some embodiments, the covalent modification of the monoclonal antibody of the invention comprises the addition of one or more labels, such as detection labels. The label or labelling group may be coupled to the antibody via spacer arms of various lengths to reduce potential steric hindrance. Various methods for labelling proteins are known in the art and can be used in performing the present invention. The term "label" or "labelling group" refers to any detectable label. In general, labels fall into a variety of classes, depending on the assay in which they are to be detected—the following examples include, but are not limited to:

a) isotopic labels, which may be radioactive or heavy isotopes, such as radioisotopes or radionuclides (e.g., $^{3}$H, $^{14}$C, $^{15}$7 N, $^{35}$S, $^{89}$Zr, $^{90}$Y, $^{99}$Tc, $^{111}$In, $^{125}$I, $^{131}$I)
b) magnetic labels (e.g., magnetic particles)
c) redox active moieties
d) optical dyes (including, but not limited to, chromophores, phosphors and fluorophores) such as fluorescent groups (e.g., FITC, rhodamine, lanthanide phosphors), chemiluminescent groups, and fluorophores which can be either "small molecule" fluores or proteinaceous fluores
e) enzymatic groups (e.g. horseradish peroxidase, β-galactosidase, luciferase, alkaline phosphatase)
f) biotinylated groups
g) predetermined polypeptide epitopes recognized by a secondary reporter (e.g., leucine zipper pair sequences, binding sites for secondary antibodies, metal binding domains, epitope tags, etc.)

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, Oreg.), FITC, Rhodamine, and Texas Red (Pierce, Rockford, Ill.), Cy5, Cy5.5, Cy7 (Amersham Life Science, Pittsburgh, PA). Suitable optical dyes, including fluorophores, are described in Molecular Probes Handbook by Richard P. Haugland.

Suitable proteinaceous fluorescent labels also include, but are not limited to, green fluorescent protein, including a Renilla, Ptilosarcus, or Aequorea species of GFP (Chalfie et al., 1994, *Science* 263:802-805), EGFP (Clontech Laboratories, Inc., Genbank® Accession Number U55762), blue fluorescent protein (BFP, Quantum Biotechnologies, Inc. 1801 de Maisonneuve Blvd. West, 8th Floor, Montreal, Quebec, Canada H3H 1J9; Stauber, 1998, *Biotechniques* 24:462-471; Heim et al., 1996, *Curr. Biol.* 6:178-182), enhanced yellow fluorescent protein (EYFP, Clontech Laboratories, Inc.), luciferase (Ichiki et al., 1993, *J. Immunol.* 150:5408-5417), β galactosidase (Nolan et al., 1988, *Proc. Natl. Acad. Sci. U.S.A.* 85:2603-2607) and Renilla (WO92/15673, WO95/07463, WO98/14605, WO98/26277, WO99/49019, U.S. Pat. Nos. 5,292,658; 5,418,155; 5,683,888; 5,741,668; 5,777,079; 5,804,387; 5,874,304; 5,876,995; 5,925,558).

The antibody/antibody construct of the invention may also comprise additional domains, which are e.g. helpful in the isolation of the molecule or relate to an adapted pharmacokinetic profile of the molecule. Domains helpful for the isolation of an antibody/antibody construct may be selected from peptide motives or secondarily introduced moieties, which can be captured in an isolation method, e.g. an isolation column. Non-limiting embodiments of such additional domains comprise peptide motives known as Myc-tag, HAT-tag, HA-tag, TAP-tag, GST-tag, chitin binding domain (CBD-tag), maltose binding protein (MBP-tag), Flag-tag, Strep-tag and variants thereof (e.g. StrepII-tag) and His-tag. All herein disclosed antibody constructs characterized by the identified CDRs may comprise a His-tag domain, which is generally known as a repeat of consecutive His residues in the amino acid sequence of a molecule, e.g. of five His residues, or of six His residues (hexa-histidine). The His-tag may be located e.g. at the N- or C-terminus of an antibody construct. In one embodiment, a hexa-histidine tag is linked via peptide bond to the C-terminus of an antibody construct according to the invention.

The invention further provides a polynucleotide/nucleic acid molecule encoding a monoclonal antibody (or antibody construct) of the invention. Nucleic acid molecules are biopolymers composed of nucleotides. A polynucleotide is a biopolymer composed of 13 or more nucleotide monomers covalently bonded in a chain. DNA (such as cDNA) and RNA (such as mRNA) are examples of polynucleotides/nucleic acid molecules with distinct biological function. Nucleotides are organic molecules that serve as the monomers or subunits of nucleic acid molecules like DNA or RNA. The nucleic acid molecule or polynucleotide of the present invention can be double stranded or single stranded, linear or circular. It is envisaged that the nucleic acid molecule or polynucleotide is comprised in a vector. It is furthermore envisaged that such vector is comprised in a host cell. Said host cell is, e.g. after transformation or transfection with the vector or the polynucleotide/nucleic acid molecule of the invention, capable of expressing the monoclonal antibody (or antibody construct). For this purpose, the polynucleotide or nucleic acid molecule is operatively linked with control sequences.

The genetic code is the set of rules by which information encoded within genetic material (nucleic acids) is translated into proteins. Biological decoding in living cells is accomplished by the ribosome which links amino acids in an order specified by mRNA, using tRNA molecules to carry amino acids and to read the mRNA three nucleotides at a time. The code defines how sequences of these nucleotide triplets, called codons, specify which amino acid will be added next during protein synthesis. With some exceptions, a three-nucleotide codon in a nucleic acid sequence specifies a single amino acid. Because the vast majority of genes are encoded with exactly the same code, this particular code is often referred to as the canonical or standard genetic code.

Degeneracy of codons is the redundancy of the genetic code, exhibited as the multiplicity of three-base pair codon combinations that specify an amino acid. Degeneracy results because there are more codons than encodable amino acids. The codons encoding one amino acid may differ in any of their three positions; however, more often than not, this difference is in the second or third position. For instance, codons GAA and GAG both specify glutamic acid and exhibit redundancy; but, neither specifies any other amino acid and thus demonstrate no ambiguity. The genetic codes of different organisms can be biased towards using one of the several codons that encode the same amino acid over the others—that is, a greater frequency of one will be found than expected by chance. For example, leucine is specified by six distinct codons, some of which are rarely used. Codon usage tables detailing genomic codon usage frequencies for most organisms are available. Recombinant gene technologies commonly take advantage of this effect by implementing a technique termed codon optimization, in which those codons are used to design a polynucleotide which are preferred by the respective host cell (such as a cell of human hamster origin, an *Escherichia coli* cell, or a *Saccharomyces cerevisiae* cell), e.g. in order to increase protein expression. It is hence envisaged that the polynucleotides/nucleic acid molecules of the present disclosure are codon optimized. Nevertheless, the polynucleotide/nucleic acid molecule encoding a monoclonal antibody (or antibody construct) of the invention may be designed using any codon that encodes the desired amino acid.

According to one embodiment, the polynucleotide/nucleic acid molecule of the present invention encoding the monoclonal antibody (or antibody construct) of the invention is in the form of one single molecule or in the form of two or more separate molecules. If the antibody construct of the present invention is a single chain antibody construct, the polynucleotide/nucleic acid molecule encoding such construct will most likely also be in the form of one single molecule. However, it is also envisaged that different components of the monoclonal antibody (such as the heavy chain and the light chain) or of the antibody construct are located on separate polypeptide chains, in which case the polynucleotide/nucleic acid molecule is most likely in the form of two (or more) separate molecules.

The same applies for the vector comprising a polynucleotide/nucleic acid molecule of the present invention. If the antibody construct of the present invention is a single chain antibody construct, one vector may comprise the polynucleotide which encodes the antibody construct in one single location (as one single open reading frame, ORF). One vector may also comprise two or more polynucleotides/nucleic acid molecules at separate locations (with individual ORFs), each one of them encoding a different component of the monoclonal antibody, such as the heavy chain and the light chain, or of the antibody construct of the invention. It is envisaged that the vector comprising the polynucleotide/nucleic acid molecule of the present invention is in the form of one single vector or two or more separate vectors. In one embodiment, and for the purpose of expressing the monoclonal antibody (or antibody construct) in a host cell, the host cell of the invention should comprise the polynucleotide/nucleic acid molecule encoding the monoclonal antibody (or antibody construct) or the vector comprising such polynucleotide/nucleic acid molecule in their entirety, meaning that all components of the monoclonal antibody (or antibody construct)—whether encoded as one single molecule or in separate molecules/locations—will assemble after translation and form together the biologically active monoclonal antibody (or antibody construct) of the invention.

The invention also provides a vector comprising a polynucleotide/nucleic acid molecule of the invention. A vector is a nucleic acid molecule used as a vehicle to transfer (foreign) genetic material into a cell, usually for the purpose of replication and/or expression. The term "vector" encompasses—but is not restricted to—plasmids, viruses, cosmids, and artificial chromosomes. Some vectors are designed specifically for cloning (cloning vectors), others for protein expression (expression vectors). So-called transcription vectors are mainly used to amplify their insert. The manipulation of DNA is normally conducted on *E. coli* vectors, which contain elements necessary for their maintenance in *E. coli*. However, vectors may also have elements that allow them to be maintained in another organism such as yeast, plant or mammalian cells, and these vectors are called shuttle vectors. Insertion of a vector into the target or host cell is usually called transformation for bacterial cells and transfection for eukaryotic cells, while insertion of a viral vector is often called transduction.

In general, engineered vectors comprise an origin of replication, a multicloning site and a selectable marker. The vector itself is generally a nucleotide sequence, commonly a DNA sequence, that comprises an insert (transgene) and a larger sequence that serves as the "backbone" of the vector. While the genetic code determines the polypeptide sequence for a given coding region, other genomic regions can influence when and where these polypeptides are produced. Modern vectors may therefore encompass additional features besides the transgene insert and a backbone: promoter, genetic marker, antibiotic resistance, reporter gene, targeting sequence, protein purification tag. Vectors called expression vectors (expression constructs) specifically are for the expression of the transgene in the target cell, and generally have control sequences.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, a Kozak sequence and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the nucleotide sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Transfection" is the process of deliberately introducing nucleic acid molecules or polynucleotides (including vectors) into target cells. The term is mostly used for non-viral methods in eukaryotic cells. Transduction is often used to describe virus-mediated transfer of nucleic acid molecules or polynucleotides. Transfection of animal cells typically involves opening transient pores or "holes" in the cell membrane, to allow the uptake of material. Transfection can be carried out using biological particles (such as viral transfection, also called viral transduction), chemical-based methods (such as using calcium phosphate, lipofection, Fugene, cationic polymers, nanoparticles) or physical treatment (such as electroporation, microinjection, gene gun, cell squeezing, magnetofection, hydrostatic pressure, impalefection, sonication, optical transfection, heat shock).

The term "transformation" is used to describe non-viral transfer of nucleic acid molecules or polynucleotides (including vectors) into bacteria, and also into non-animal eukaryotic cells, including plant cells. Transformation is hence the genetic alteration of a bacterial or non-animal eukaryotic cell resulting from the direct uptake through the cell membrane(s) from its surroundings and subsequent incorporation of exogenous genetic material (nucleic acid molecules). Transformation can be carried out by artificial means. For transformation to happen, cells or bacteria must be in a state of competence, which might occur as a time-limited response to environmental conditions such as starvation and cell density, and can also be artificially induced.

Moreover, the invention provides a host cell transformed or transfected with the polynucleotide/nucleic acid molecule of the invention or with the vector of the invention. As used herein, the terms "host cell" or "recipient cell" are intended to include any individual cell or cell culture that can be or has been recipient of vectors, exogenous nucleic acid molecules and/or polynucleotides encoding the monoclonal antibody (or antibody construct) of the present invention; and/or recipients of the monoclonal antibody (or antibody construct) itself. The introduction of the respective material into the cell is carried out by way of transformation, transfection and the like (vide supra). The term "host cell" is also intended to include progeny or potential progeny of a single cell. Because certain modifications may occur in succeeding generations due to either natural, accidental, or deliberate mutation or due to environmental influences, such progeny may not, in fact, be completely identical (in morphology or in genomic or total DNA complement) to the parent cell, but is still included within the scope of the term as used herein. Suitable host cells include prokaryotic or eukaryotic cells, and also include—but are not limited to—bacteria (such as *E. coli*), yeast cells, fungi cells, plant cells, and animal cells such as insect cells and mammalian cells, e.g., hamster, murine, rat, macaque or human cells.

In addition to prokaryotes, eukaryotic microbes such as filamentous fungi or yeast are suitable cloning or expression hosts for the monoclonal antibody (or antibody construct) of the invention. *Saccharomyces cerevisiae*, or common baker's yeast, is the most commonly used among lower eukaryotic host microorganisms. However, a number of other genera, species, and strains are commonly available and useful herein, such as Schizosaccharomyces pombe, Kluyveromyces hosts such as *K. lactis, K. fragilis* (ATCC 12424), *K. bulgaricus* (ATCC 16045), *K. wickeramii* (ATCC 24178), *K. waltii* (ATCC 56500), *K. drosophilarum* (ATCC 36906), *K. thermotolerans*, and *K. marxianus*; yarrowia (EP 402 226); *Pichia pastoris* (EP 183 070); Candida; *Trichoderma reesia* (EP 244 234); *Neurospora crassa;* Schwanniomyces such as *Schwanniomyces occidentalis*; and filamentous fungi such as Neurospora, Penicillium, Tolypocladium, and Aspergillus hosts such as *A. nidulans* and *A. niger.*

Suitable host cells for the expression of a glycosylated monoclonal antibody (or antibody construct) are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruit fly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, *Arabidopsis* and tobacco can also be used as hosts. Cloning and expression vectors useful in the production of proteins in plant cell culture are known to those of skill in the art. See e.g. Hiatt et al., Nature (1989) 342: 76-78, Owen et al. (1992) Bio/Technology 10: 790-794, Artsaenko et al. (1995) The Plant J 8: 745-750, and Fecker et al. (1996) Plant Mol Biol 32: 979-986.

However, interest has been greatest in vertebrate cells, and propagation of vertebrate cells in culture (cell culture) has become a routine procedure. Examples of useful mammalian host cell lines are monkey kidney CV1 line transformed by SV40 (such as COS-7, ATCC CRL 1651); human embryonic kidney line (such as 293 or 293 cells subcloned for growth in suspension culture, Graham et al., J. Gen Virol. 36: 59 (1977)); baby hamster kidney cells (such as BHK, ATCC CCL 10); Chinese hamster ovary cells/-DHFR (such as CHO, Urlaub et al., Proc. Natl. Acad. Sci. USA 77: 4216 (1980)); mouse sertoli cells (such as TM4, Mather, Biol. Reprod. 23: 243-251 (1980)); monkey kidney cells (such as CVI ATCC CCL 70); African green monkey kidney cells (such as VERO-76, ATCC CRL1587); human cervical carcinoma cells (such as HELA, ATCC CCL 2); canine kidney cells (such as MDCK, ATCC CCL 34); buffalo rat liver cells (such as BRL 3A, ATCC CRL 1442); human lung cells (such as W138, ATCC CCL 75); human liver cells (such as Hep G2,1413 8065); mouse mammary tumor (such as MMT 060562, ATCC CCL-51); TRI cells (Mather et al., Annals N. Y Acad. Sci. (1982) 383: 44-68); MRC 5 cells; FS4 cells; and a human hepatoma line (such as Hep G2).

In a further embodiment, the invention provides a process for producing a monoclonal antibody (or antibody construct) of the invention, said process comprising culturing a host cell of the invention under conditions allowing the expression of the monoclonal antibody (or antibody construct) of the invention and recovering the produced monoclonal antibody (or antibody construct) from the culture.

As used herein, the term "culturing" refers to the in vitro maintenance, differentiation, growth, proliferation and/or propagation of cells under suitable conditions in a medium. Cells are grown and maintained in a cell growth medium at an appropriate temperature and gas mixture. Culture conditions vary widely for each cell type. Typical growth conditions are a temperature of about 37° C., a $CO_2$ concentration of about 5% and a humidity of about 95%. Recipes for growth media can vary e.g. in pH, concentration of the carbon source (such as glucose), nature and concentration of growth factors, and the presence of other nutrients (such as amino acids or vitamins). The growth factors used to supplement media are often derived from the serum of animal blood, such as fetal bovine serum (FBS), bovine calf serum (FCS), equine serum, and porcine serum. Cells can be grown either in suspension or as adherent cultures. There are also cell lines that have been modified to be able to survive in suspension cultures so they can be grown to a higher density than adherent conditions would allow.

The term "expression" includes any step involved in the production of a monoclonal antibody (or antibody construct) of the invention including, but not limited to, transcription, post-transcriptional modification, translation, folding, post-translational modification, targeting to specific subcellular or extracellular locations, and secretion. The term "recovering" refers to a series of processes intended to isolate the monoclonal antibody (or antibody construct) from the cell culture. The "recovering" or "purification" process may separate the protein and non-protein parts of the cell culture, and finally separate the desired monoclonal antibody (or antibody construct) from all other polypeptides and proteins. Separation steps usually exploit differences in protein size, physico-chemical properties, binding affinity and biological activity. Preparative purifications aim to produce a relatively large quantity of purified proteins for subsequent use, while analytical purification produces a relatively small amount of a protein for a variety of research or analytical purposes.

When using recombinant techniques, the monoclonal antibody (or antibody construct) can be produced intracellularly, in the periplasmic space, or directly secreted into the medium. If the monoclonal antibody (or antibody construct) is produced intracellularly, as a first step, the particulate debris, either host cells or lysed fragments, are removed, for example, by centrifugation or ultrafiltration. The monoclonal antibody (or antibody construct) of the invention may e.g. be produced in bacteria such as E. coli. After expression, the construct is isolated from the bacterial cell paste in a soluble fraction and can be purified e.g. via affinity chromatography and/or size exclusion. Final purification can be carried out in a manner similar to the process for purifying a monoclonal antibody (or antibody construct) expressed in mammalian cells and secreted into the medium. Carter et al. (Biotechnology (NY) 1992 Feb.; 10(2):163-7) describe a procedure for isolating antibodies which are secreted to the periplasmic space of E. coli.

Where the monoclonal antibody (or antibody construct) is secreted into the medium, supernatants from such expression systems are generally first concentrated using a commercially available protein concentration filter, for example, an ultrafiltration unit.

The monoclonal antibody (or antibody construct) of the invention prepared from the host cells can be recovered or purified using, for example, hydroxylapatite chromatography, gel electrophoresis, dialysis, and affinity chromatography. Other techniques for protein purification such as fractionation on an ion-exchange column, mixed mode ion exchange, HIC, ethanol precipitation, size exclusion chromatography, reverse phase HPLC, chromatography on silica, chromatography on heparin sepharose, chromatography on an anion or cation exchange resin (such as a polyaspartic acid column), immunoaffinity (such as Protein A/G/L) chromatography, chromato-focusing, SDS-PAGE, ultracentrifugation, and ammonium sulfate precipitation are also available depending on the monoclonal antibody (or antibody construct) to be recovered. A protease inhibitor may be included in any of the foregoing steps to inhibit proteolysis, and antibiotics may be included to prevent the growth of contaminants.

Moreover, the invention provides a composition or formulation comprising the monoclonal antibody (or antibody construct) of the invention or comprising the monoclonal antibody (or antibody construct) produced according to the process of the invention. The composition is preferably a diagnostic composition. As used herein, the term "diagnostic composition" relates to a composition which is suitable for use in a diagnostic kit or in a detection system. One possible diagnostic composition of this invention comprises one or a plurality of the monoclonal antibodies (or antibody constructs) of the invention, preferably in an amount that is useful for the detection of sBCMA in a sample. The diagnostic composition may further comprise suitable formulations of one or more carriers, stabilizers, excipients, diluents, solubilizers, surfactants, emulsifiers, preservatives and/or adjuvants. Diagnostic compositions of the invention include, but are not limited to, liquid, frozen, and lyophilized compositions.

The compositions may comprise a carrier such as a diagnostically acceptable carrier. In general, as used herein, "diagnostically acceptable carrier" means any and all aqueous and non-aqueous solutions, sterile solutions, solvents, buffers, e.g. phosphate buffered saline (PBS) solutions, water, suspensions, emulsions, such as oil/water emulsions, various types of wetting agents, liposomes, dispersion media and coatings, which are compatible with diagnostic use. The use of such media and agents in diagnostic compositions is well known in the art, and the compositions comprising such carriers can be formulated by well-known conventional methods.

Certain embodiments provide diagnostic compositions comprising the antibody (or antibody construct) of the invention and further one or more excipients such as those illustratively described in this section and elsewhere herein. Excipients can be used in the invention for a wide variety of purposes, such as adjusting physical, chemical, or biological properties of formulations, such as adjustment of viscosity, and or processes of the invention to improve effectiveness and/or to stabilize such formulations and processes against degradation and spoilage e.g. due to stresses that occur during manufacturing, shipping, storage, pre-use preparation, administration, and thereafter. Excipients should in general be used in their lowest effective concentrations.

In certain embodiments, the diagnostic composition may contain formulation materials for the purpose of modifying, maintaining or preserving certain characteristics of the composition such as the pH, osmolarity, viscosity, clarity, color, isotonicity, odor, sterility, stability, rate of dissolution or release, adsorption or penetration (see, Remington's Pharmaceutical Sciences, 18" Edition, 1990, Mack Publishing Company). In such embodiments, suitable formulation materials may include, but are not limited to:
 amino acids
 antimicrobials such as antibacterial and antifungal agents
 antioxidants
 buffers, buffer systems and buffering agents which are used to maintain the composition at physiological pH or at a slightly lower pH, typically within a pH range of from about 5 to about 8 or 9
 non-aqueous solvents, vegetable oils, and injectable organic esters
 aqueous carriers including water, alcoholic/aqueous solutions, emulsions or suspensions, including saline and buffered media biodegradable polymers such as polyesters
bulking agents
chelating agents
isotonic and absorption delaying agents
complexing agents
fillers
carbohydrates
(low molecular weight) proteins, polypeptides or proteinaceous carriers, preferably of human origin
coloring and flavouring agents
sulfur containing reducing agents
diluting agents
emulsifying agents
hydrophilic polymers
salt-forming counter-ions
preservatives
metal complexes
solvents and co-solvents
sugars and sugar alcohols
suspending agents
surfactants or wetting agents
stability enhancing agents
tonicity enhancing agents
parenteral delivery vehicles
intravenous delivery vehicles It is common knowledge that the different constituents of the diagnostic composition can have different effects, for example, and amino acid can act as a buffer, a stabilizer and/or an antioxidant; mannitol can act as a bulking agent and/or a tonicity enhancing agent; sodium chloride can act as delivery vehicle and/or tonicity enhancing agent; etc.

According to a further aspect, the present invention provides a detection system comprising:
a) a first monoclonal antibody (or antibody construct) which binds to sBCMA, and
b) a second monoclonal antibody (or antibody construct) which binds to sBCMA, wherein the binding of the first monoclonal antibody (or antibody construct) to sBCMA occurs in the presence of the second monoclonal antibody (or antibody construct) binding to sBCMA.

The present invention also provides a detection system comprising:
a) a first monoclonal antibody (or antibody construct) which binds to sBCMA, and
b) a second monoclonal antibody (or antibody construct) which binds to sBCMA, wherein the binding of the second monoclonal antibody (or antibody construct) to sBCMA occurs in the presence of the first monoclonal antibody (or antibody construct) binding to sBCMA.

The present invention also provides a detection system comprising:
a) a first monoclonal antibody (or antibody construct) which binds to sBCMA, and
b) a second monoclonal antibody (or antibody construct) which binds to sBCMA, wherein the binding of the first monoclonal antibody (or antibody construct) to sBCMA occurs in the presence of the second monoclonal antibody (or antibody construct) binding to sBCMA, and wherein the binding of the second monoclonal antibody (or antibody construct) to sBCMA occurs in the presence of the first monoclonal antibody (or antibody construct) binding to sBCMA.

A "detection system" is a kit or tool (or a diagnostic kit/tool) comprising reagents for carrying out an analytical assay. In the context of the present invention, the assay detects and/or quantifies the presence of sBCMA in a sample, usually a liquid sample. The detection system comprises a pair of antibodies (first and second monoclonal antibody) which bind to sBCMA. Usually, the detection system involves the use of a solid support (such as a microtiter plate or a membrane) which serves as a surface to immobilize either the antigen to be detected (e.g. in the case of a "direct ELISA") or the (monoclonal) antibody binding to sBCMA (the "capture antibody"), or a "secondary antibody" (e.g. an anti-Fc antibody) which binds to the antibody binding to sBCMA (the capture antibody). In general, the immobilization occurs either non-specifically (via adsorption to the surface) or specifically (via capture by an antibody, e.g. a secondary antibody). A detection system may furthermore comprise a (monoclonal) detection antibody binding to sBCMA (optionally coupled with an enzyme, a detectable label or a reporter group), and optionally a secondary antibody (e.g. an anti-Fc antibody) which binds to the detection antibody and which is coupled with an enzyme, a detectable label or a reporter group. In the present case, the capture antibody may be the "first monoclonal antibody (or antibody construct) which binds to sBCMA" and the detection antibody may be the "second monoclonal antibody (or antibody construct) which binds to sBCMA", or vice versa. In other words, either the first or the second monoclonal antibody or antibody construct of the invention may be coupled with an enzyme, a detectable label or a reporter group.

A very well know detection system is the ELISA assay, which can be used for the purposes of the present invention. A "sandwich" ELISA is used to detect sample antigen (here: sBCMA) or to quantify an unknown amount of the antigen. The steps may include: A surface is provided to which a known quantity of so-called "capture antibody" is bound. This binding may occur directly via adsorption of the capture antibody to the surface or via a secondary antibody (e.g. an anti-Fc antibody) which is adsorbed to the surface and which binds to the capture antibody. Any nonspecific binding sites on the surface are blocked. The antigen-containing sample is applied to the surface, and antigen is captured (bound) by the antibody. The plate is washed to remove unbound antigen. A "detection antibody" is added and binds to the antigen. This detection antibody may be coupled (e.g. covalently linked) with an enzyme, a detectable label or a reporter group. If this is not the case, a secondary antibody is applied that is coupled with an enzyme, a detectable label or a reporter group and that binds to the detection antibody, e.g. to its Fc region. The plate is washed to remove any unbound antibodies. A chemical substrate is added that is converted (e.g. by the enzyme) to a detectable form, such as an optical signal (e.g. color or fluorescent) or an electrochemical signal. The absorbance or fluorescence or electrochemical signal (e.g., current) of the plate wells or surface is measured to determine the presence and/or quantity of the antigen. Commonly used enzymatic markers include:

OPD (o-phenylenediamine dihydrochloride) turns amber to detect horseradish peroxidase (HRP) which is often used as conjugated protein TMB (3,3',5,5'-tetramethylbenzidine) turns blue when detecting HRP and turns yellow sulfuric or phosphoric acid ABTS (2,2'-Azinobis [3-ethylbenzothiazoline-6-sulfonic acid]-diammonium salt) turns green when detecting HRP PNPP (p-Nitrophenyl Phosphate, Disodium Salt) turns yellow when detecting alkaline phosphatase Traditional ELISA typically involves chromogenic reporters and substrates that produce observable color change to indicate the presence of antigen. Newer ELISA-like techniques use fluorogenic, electrochemiluminescent and quantitative PCR reporters to create quantifiable signals. These new reporters can have various advantages, including higher sensitivities and multiplexing. In technical terms, these assays are not strictly "ELISAs", as they are not "enzyme-linked", but are instead linked to some non-enzymatic reporter. However, given that the general principles in these assays are largely similar, they are often grouped in the same category as ELISAs.

The detection system may be used in a qualitative or quantitative format. Qualitative results provide a simple positive or negative result (yes or no) for a sample. The cutoff between positive and negative may be statistical. Two or three times the standard deviation (error inherent in a test) is often used to distinguish positive from negative samples. In a quantitative format, the optical density (OD) of the sample or the electrochemical signal is compared to a standard curve, which is typically a serial dilution of a known-concentration solution of the target molecule (sBCMA).

The definitions and specifications of the monoclonal antibody according to the invention and the second monoclonal antibody, as provided herein above, similarly apply for the first monoclonal antibody and the second monoclonal antibody that are comprised within the detection system of the invention. For example, it is envisaged that sBCMA has the amino acid sequence as depicted in SEQ ID NO: 34. It is also envisaged that the binding of the first monoclonal antibody to sBCMA and the binding of the second monoclonal antibody to sBCMA occur in the presence of a third antibody or antibody construct binding to sBCMA. This third antibody or antibody construct may be a therapeutic anti-BCMA antibody or antibody construct, such as an antibody drug conjugate (ADC) or a CD3xBCMA bispecific antibody. The third antibody or antibody construct can be present in the sample (e.g. biological sample) to be analyzed using the detection system. See herein above for more details on the third antibody/antibody construct binding to sBCMA. Furthermore, it is envisaged that the first monoclonal antibody (or antibody construct) of the detection system comprises (a) a rabbit VH region, (b) a rabbit VL region or (c) a rabbit VH region and a rabbit VL region. Likewise, the second monoclonal antibody (or antibody construct) of the detection system may comprise (a) a rabbit VH region, (b) a rabbit VL region or (c) a rabbit VH region and a rabbit VL region. Furthermore, the entire first monoclonal antibody and/or the entire second monoclonal antibody of the detection system can be a rabbit antibody. It is also envisaged that the first monoclonal antibody and/or the second monoclonal antibody of the detection system has/have an affinity (KD) to sBCMA of about $\leq 10^{-7}$ M, $\leq 10^{-8}$ M, $\leq 10^{-9}$ M, or $\leq 10^{-10}$ M. It is also envisaged that the first monoclonal antibody of the detection system and/or the second monoclonal antibody of the detection system is/are an IgG, IgD, IgE, IgM or IgA antibody. According to one embodiment, the first and/or second monoclonal antibody is an IgG antibody, such as an IgG1, IgG2, IgG3 or IgG4 antibody. The isotype and subclass of the antibody may be of rabbit (e.g. rabbit IgG, rabbit IgG1 etc.).

The present invention also provides that the first monoclonal antibody (or antibody construct) of the detection system:
  a) comprises a VH region comprising a VH-CDR1 as depicted in SEQ ID NO: 1, a VH-CDR2 as depicted in SEQ ID NO: 2, and a VH-CDR3 as depicted in SEQ ID NO: 3, and a VL region comprising a VL-CDR1 as depicted in SEQ ID NO: 4, a VL-CDR2 as depicted in SEQ ID NO: 5, and a VL-CDR3 as depicted in SEQ ID NO: 6;
  b) comprises a VH region comprising a VH-CDR1 as depicted in SEQ ID NO: 11, a VH-CDR2 as depicted in SEQ ID NO: 12, and a VH-CDR3 as depicted in SEQ ID NO: 13, and a VL region comprising a VL-CDR1 as depicted in SEQ ID NO: 14, a VL-CDR2 as depicted in SEQ ID NO: 15, and a VL-CDR3 as depicted in SEQ ID NO: 16;
  c) binds to the same sBCMA epitope as the antibody of a), or competes for binding to sBCMA with the antibody of a); or
  d) binds to the same sBCMA epitope as the antibody of b), or competes for binding to sBCMA with the antibody of b); and/or that the second monoclonal antibody (or antibody construct) of the detection system:
  e) comprises a VH region comprising a VH-CDR1 as depicted in SEQ ID NO: 21, a VH-CDR2 as depicted in SEQ ID NO: 22, and a VH-CDR3 as depicted in SEQ ID NO: 23, and a VL region comprising a VL-CDR1 as depicted in SEQ ID NO: 24, a VL-CDR2 as depicted in SEQ ID NO: 25, and a VL-CDR3 as depicted in SEQ ID NO: 26; or
  f) binds to the same sBCMA epitope as the antibody of e) or competes for binding to sBCMA with the antibody of e).

The present invention also provides that the first monoclonal antibody (or antibody construct) of the detection system:
  a) comprises a VH region as depicted in SEQ ID NO: 7 or 17;
  b) comprises a VL region as depicted in SEQ ID NO: 8 or 18;
  c) comprises a VH region as depicted in SEQ ID NO: 7 and a VL region as depicted in SEQ ID NO: 8;
  d) comprises a VH region as depicted in SEQ ID NO: 17 and a VL region as depicted in SEQ ID NO: 18;
  e) binds to the same sBCMA epitope as the antibody of c), or competes for binding to sBCMA with the antibody of c); or
  f) binds to the same sBCMA epitope as the antibody of d), or competes for binding to sBCMA with the antibody of d); and/or that the second monoclonal antibody (or antibody construct) of the detection system:
  g) comprises a VH region as depicted in SEQ ID NO: 27;
  h) comprises a VL region as depicted in SEQ ID NO: 28;
  i) comprises a VH region as depicted in SEQ ID NO: 27 and a VL region as depicted in SEQ ID NO: 28; or
  j) binds to the same sBCMA epitope as the antibody of i) or competes for binding to sBCMA with the antibody of i).

It is envisaged for the detection system that
  a) either the first monoclonal antibody (or antibody construct) is used as capture antibody, and the second monoclonal antibody (or antibody construct) is used as detection antibody, or
  b) the first monoclonal antibody (or antibody construct) is used as detection antibody, and the second monoclonal antibody (or antibody construct) is used as capture antibody.

In a further aspect, the present invention also provides the use of a monoclonal antibody (or antibody construct) of the present invention or the use of the detection system of the present invention for:

detecting sBCMA in a sample;
quantifying sBCMA in a sample;
diagnosing a disease associated with sBCMA or increased sBCMA;
stratifying patients diagnosed with a disease associated with sBCMA or increased sBCMA;
monitoring the progression of a disease associated with sBCMA or increased sBCMA; or
monitoring the response to treatment of a disease associated with sBCMA or increased sBCMA.

In one embodiment, the sample is a biological sample, such as a human biological sample. A sample (biological sample/human biological sample) may be a serum sample, plasma sample, blood sample, bone marrow sample or tissue sample. The sample may also be supernatant obtained from a cell culture of bone marrow mononuclear cells or of peripheral blood mononuclear cells. The sample may be obtained from a subject, e.g. a human subject, suspected of having or having (being diagnosed with) a disease associated with sBCMA or increased sBCMA, or a subject having received treatment for a disease associated with sBCMA or increased sBCMA.

A disease is a particular abnormal condition that negatively affects the structure or function of part or all of an organism, such as a human, and that is not due to any external injury. Diseases are often construed as "medical conditions" or "disorders" that are associated with specific signs and symptoms. The disease according to the present invention is associated with sBCMA or increased sBCMA. This sBCMA can e.g. be detected and/or quantified in the bone marrow, blood, serum or plasma, e.g. of a human subject, or in the supernatant obtained from a cell culture of bone marrow mononuclear cells or of peripheral blood mononuclear cells, e.g. of a human subject. The term "increased" is used comparison with a healthy subject, i.e. a subject that does not have such disease. According to one embodiment, the disease associated with sBCMA or increased sBCMA is a "BCMA positive neoplasm".

A "neoplasm" is an abnormal growth of tissue, usually but not always forming a mass. When also forming a mass, it is commonly referred to as a "tumor". In brain tumors, the uncontrolled division of cells means that the mass of a neoplasm increases in size, and in a confined space such as the intracranial cavity this quickly becomes problematic because the mass invades the space of the brain pushing it aside, leading to compression of the brain tissue and increased intracranial pressure and destruction of parenchyma. According to the invention, the "neoplasm" or "tumor" also refers to a condition that would benefit from treatment with a therapy directed to BCMA, in particular, BCMA expressed on the cell surface (such as BCMA-specific antibodies—including naked antibodies, antibody-drug conjugates (ADCs), bispecific antibodies such as those directed against BCMA and CD3—as well as cellular therapies such as chimeric antigen receptor T-cells (CAR-T)), such therapies including but not limited to AMG 420, AMG 701, GSK 916, JNJ-64007957 (JNJ-7957), PF-06863135 (PF-3135), CC-93269, REGN5458, HPN217, TNB-383B, P-BCMA-101, JNJ-68284528, JCARH125, and bb2121. This condition includes chronic and acute disorders or diseases including those pathological conditions that predispose a mammal to the condition (neoplasm or tumor) in question.

Neoplasms or tumors can be benign, potentially malignant (pre-cancerous), or malignant (cancerous). Malignant neoplasms/tumors are commonly called cancer. They usually invade and destroy the surrounding tissue and may form metastases, i.e., they spread to other parts, tissues or organs of the body. A "primary tumor" is a tumor growing at the anatomical site where tumor progression began and proceeded to yield a cancerous mass. For example, a brain tumor occurs when abnormal cells form within the brain. Most cancers develop at their primary site but then go on to form metastases or spread to other parts (e.g. tissues and organs) of the body. These further tumors are secondary tumors. Most cancers continue to be called after their primary site, even after they have spread to other parts of the body.

Lymphomas and leukemias are hematopoietic or lymphoid neoplasms. For the purposes of the present invention, lymphomas and leukemias are also encompassed by the terms "tumor", "cancer" or "neoplasm". Lymphoma is a group of blood cancers that develop from lymphocytes (a type of white blood cell). Leukemia is a group of cancers that usually begin in the bone marrow and result in high numbers of abnormal white blood cells. These white blood cells are not fully developed and are called blasts or leukemia cells. Lymphomas and leukemias are a part of the broader group of tumors of the hematopoietic and lymphoid tissues.

For the purposes of the present invention, the terms "neoplasm", "tumor" and "cancer" may be used interchangeably, and they comprise both primary tumors/cancers and secondary tumors/cancers (or "metastases"), as well as mass-forming neoplasms (tumors) and lymphoid neoplasms (such as lymphomas and leukemias), and also MRD.

The term "minimal residual disease" (MRD) refers to the evidence for the presence of small numbers of residual cancer cells that remain in the patient after cancer treatment, e.g. when the patient is in remission (the patient has no symptoms or signs of disease). A very small number of remaining cancer cells usually cannot be detected by routine means because the standard tests used to assess or detect cancer are not sensitive enough to detect MRD. Nowadays, very sensitive molecular biology tests for MRD are available, such as flow cytometry, PCR and next-generation sequencing. These tests can measure minimal levels of cancer cells in tissue samples, sometimes as low as one cancer cell in a million normal cells. In the context of the present invention, the terms "prevention", "treatment" or "amelioration" of a neoplasm are envisaged to also encompass "prevention, treatment or amelioration of MRD", whether the MRD was detected or not.

Is it envisaged that the BCMA positive neoplasm is a B cell neoplasm or a plasma cell neoplasm. B cells, also known as B lymphocytes, are a type of white blood cell of the lymphocyte subtype. They function in the humoral immunity component of the adaptive immune system by secreting antibodies. Additionally, B cells present antigen (they are also classified as professional antigen-presenting cells) and secrete cytokines. In mammals, B cells mature in the bone marrow, which is at the core of most bones. B cells, unlike the other two classes of lymphocytes—T cells and natural killer (NK) cells—express B cell receptors (BCRs) on their cell membrane. BCRs allow the B cell to bind to a specific antigen, against which it will initiate an antibody response. Plasma cells, also called plasma B cells, plasmocytes, or effector B cells, are white blood cells that secrete large volumes of antibodies. They are usually transported by the blood plasma and the lymphatic system. Plasma cells originate in the bone marrow. B cells differentiate into plasma cells that produce antibody molecules closely modelled after the receptors of the precursor B cell. Once released into the blood and lymph, these antibody molecules bind to the target antigen and initiate its neutralization or destruction.

The "disease associated with sBCMA or increased sBCMA", the "BCMA positive neoplasm" or the "(BCMA positive) B cell neoplasm or plasma cell neoplasm" may be selected from the group including, but not limited to, multiple myeloma, relapsed and/or refractory multiple myeloma, heavy chain multiple myeloma, light chain multiple myeloma, extramedullary myeloma (extramedullary plasmacytoma, extramedullary multiple myeloma), plasmacytoma, plasma cell leukemia, Waldenstrom's macroglobulinemia (lymphoplasmacytic lymphoma), smoldering myeloma (smoldering multiple myeloma), chronic lymphocytic leukemia (CLL), primary CNS lymphoma (PCNSL) and B-cell non-Hodgkin lymphoma (B-NHL). The Multiple Myeloma can be selected from the group consisting of or comprising relapsed and/or refractory multiple myeloma, heavy chain multiple myeloma, light chain multiple myeloma, extramedullary multiple myeloma, and smoldering multiple myeloma.

"Diagnosis" or "medical diagnosis" is the process of determining which disorder or condition explains a subject's symptoms and signs. Usually, one or more diagnostic procedures, such as diagnostic or medical tests, are done during the process. In medicine, the term "monitoring" refers to the observation of a disease, condition or one or several medical parameters over time. It can be performed by continuously measuring certain parameters by using a medical monitor and/or by repeatedly performing medical tests. A diagnostic or medical test is a medical procedure performed to detect, diagnose or monitor diseases, disease processes, susceptibility, and/or determine a course of treatment. It is related to clinical chemistry and molecular diagnostics, and the procedures are typically performed in a medical laboratory.

Medical therapies or treatments are efforts to cure or improve a disease. In the medical field, common treatments include medications. A medication (also referred to as medicine, pharmaceutical drug or drug) is used to diagnose, cure, treat or prevent a disease. The term "treatment" hence refers to both therapeutic treatment and prophylactic or preventative measures. In the context of the present invention, treatment includes the application or administration of an anti-BCMA antibody or antibody construct to the body, to an isolated tissue, or to a cell from a patient or a subject in need who has a disease as described herein, a symptom of such disease, or a predisposition toward such disease, with the purpose to cure, heal, alleviate, relieve, alter, remedy, ameliorate, improve, or affect the disease, the symptom of the disease, or the predisposition toward the disease.

In a further aspect, the present invention also provides a method for detecting and/or quantifying sBCMA in a sample, comprising the steps of:
(a) using a monoclonal antibody (or antibody construct) of the present invention, or using a detection system of the present invention for determining the content of sBCMA in a sample; and
(b) comparing the content of sBCMA determined in step (a) to
(i) a pre-defined value for the sBCMA content,
(ii) the content of sBCMA determined in a control sample, or
(iii) the content of sBCMA determined in a sample obtained from the same source or subject at a previous time point.

For the purposes of the present invention, the term "content" (of sBCMA) may be used interchangeably with the terms "level", "amount" or "concentration" (of sBCMA).

The "pre-defined value for the sBCMA content" may be a "cut-off value" which has been pre-determined. This value can e.g. indicate that a certain sBCMA content in a sample is indicative for a disease associated with sBCMA or increased sBCMA, or a BCMA positive neoplasm. For example, if the sBCMA content in a sample is determined to be three standard deviations above the predetermined cut-off value, the subject from which the sample was obtained is considered positive for multiple myeloma (or other diseases as described herein). The "control sample" is usually obtained from a source of the same nature as the sample to be analyzed (such as a serum sample). The control sample may be a sample ("negative control sample") representing a "normal" sBCMA content (e.g. representing a healthy subject), or it may be a sample ("positive control sample") representing an "abnormally increased" sBCMA content (e.g. representing a subject having a disease as defined herein).

In a further aspect, the present invention provides a method for diagnosing a disease associated with sBCMA or increased sBCMA, comprising the steps of:
(a) using a monoclonal antibody (or antibody construct) of the present invention, or using a detection system of the present invention, for determining the content of sBCMA in a sample; and
(b) comparing the content of sBCMA determined in step (a) to
(i) a pre-defined cut-off value for the sBCMA content, indicating absence of such disease, or
(ii) the content of sBCMA determined in a control sample representing absence of such disease,
wherein a higher content of sBCMA determined in step (a) as compared to the pre-defined cut-off value of (i) or the content of sBCMA determined in the control sample of (ii) indicates the presence of a disease associated with sBCMA or increased sBCMA.

In a further aspect, the present invention also provides a method for monitoring the progression of a disease associated with sBCMA or increased sBCMA or for monitoring the response to treatment of a disease associated with sBCMA or increased sBCMA, comprising the steps of:
(a) using a monoclonal antibody (or antibody construct) of the present invention, or using a detection system of the present invention, for determining the content of sBCMA at a first time point in a biological sample obtained from a subject diagnosed with such disease;
(b) using a monoclonal antibody (or antibody construct) of the present invention, or using a detection system of the present invention, for determining the content of sBCMA at a second (later) time point or after treatment in a biological sample obtained from the subject; and
(c) comparing the content of sBCMA determined in step (a) to the content of sBCMA determined in step (b);
wherein a higher content of sBCMA determined in step (a) as compared to the content of sBCMA determined in step (b) indicates that the disease is progressing, and/or wherein a lower content of sBCMA determined in step (a) as compared to the content of sBCMA determined in step (b) indicates that said disease is entering remission or that said disease is responding to the treatment.

It is envisaged for the above methods that the "sample" is a biological sample, such as a human biological sample. The sample may be a (human) serum sample, plasma sample, blood sample, bone marrow sample, tissue sample, or supernatant obtained from a cell culture of (human) bone marrow mononuclear cells or (human) peripheral blood mononuclear cells. The "sample" may also be obtained from a human subject, preferably a human subject suspected of having or having (being diagnosed with) a disease associated with sBCMA or increased sBCMA, or a subject having received treatment for a disease associated with sBCMA or increased sBCMA, as defined herein above.

It is envisaged for the above methods, that the "disease associated with sBCMA or increased sBCMA" may be a BCMA positive neoplasm. The disease or the BCMA positive neoplasm may be selected from the group consisting of multiple myeloma, relapsed and/or refractory multiple myeloma, heavy chain multiple myeloma, light chain multiple myeloma, extramedullary myeloma (extramedullary plasmacytoma, extramedullary multiple myeloma), plasmacytoma, plasma cell leukemia, Waldenstrom's macroglobulinemia (lymphoplasmacytic lymphoma), smoldering myeloma (smoldering multiple myeloma), chronic lymphocytic leukemia (CLL), primary CNS lymphoma (PCNSL) and B-cell non-Hodgkin lymphoma (B-NHL).

The present invention refers to the following items:

Item 1. A monoclonal antibody that binds to soluble BCMA (sBCMA), wherein the binding of the antibody to sBCMA occurs in the presence of a second monoclonal antibody binding to sBCMA.

Item 2. The monoclonal antibody according to item 1, wherein sBCMA has the amino acid sequence as depicted in SEQ ID NO: 34.

Item 3. The monoclonal antibody according to item 1 or 2, wherein the binding of the monoclonal antibody to sBCMA occurs in the presence of a third antibody or antibody construct binding to sBCMA.

Item 4. The monoclonal antibody according to item 3, wherein the third monoclonal antibody or antibody construct binds to epitope cluster 3 of BCMA, preferably to epitope cluster 3 of human BCMA, preferably having an amino acid sequence as depicted in SEQ ID NO: 35.

Item 5. The monoclonal antibody according to any of the preceding items, wherein the monoclonal antibody comprises a rabbit VH region and/or a rabbit VL region.

Item 6. The monoclonal antibody according to any one of the preceding items, wherein the monoclonal antibody has an affinity (KD) to sBCMA of about $\leq 10^{-7}$ M, $\leq 10^{-8}$ M, $\leq 10^{-9}$ M, or $\leq 10^{-10}$ M.

Item 7. The monoclonal antibody according to item 6, wherein the affinity is determined in a surface plasmon resonance (BIACORE™)assay.

Item 8. The monoclonal antibody according to any one of the preceding items, wherein the monoclonal antibody:
  a) comprises a VH region comprising a VH-CDR1 as depicted in SEQ ID NO: 1, a VH-CDR2 as depicted in SEQ ID NO: 2, and a VH-CDR3 as depicted in SEQ ID NO: 3, and a VL region comprising a VL-CDR1 as depicted in SEQ ID NO: 4, a VL-CDR2 as depicted in SEQ ID NO: 5, and a VL-CDR3 as depicted in SEQ ID NO: 6;
  b) comprises a VH region comprising a VH-CDR1 as depicted in SEQ ID NO: 11, a VH-CDR2 as depicted in SEQ ID NO: 12, and a VH-CDR3 as depicted in SEQ ID NO: 13, and a VL region comprising a VL-CDR1 as depicted in SEQ ID NO: 14, a VL-CDR2 as depicted in SEQ ID NO: 15, and a VL-CDR3 as depicted in SEQ ID NO: 16;
  c) comprises a VH region comprising a VH-CDR1 as depicted in SEQ ID NO: 21, a VH-CDR2 as depicted in SEQ ID NO: 22, and a VH-CDR3 as depicted in SEQ ID NO: 23, and a VL region comprising a VL-CDR1 as depicted in SEQ ID NO: 24, a VL-CDR2 as depicted in SEQ ID NO: 25, and a VL-CDR3 as depicted in SEQ ID NO: 26;
  d) binds to the same sBCMA epitope as the antibody of a) or competes for binding to sBCMA with the antibody of a);
  e) binds to the same sBCMA epitope as the antibody of b) or competes for binding to sBCMA with the antibody of b); or
  f) binds to the same sBCMA epitope as the antibody of c) or competes for binding to sBCMA with the antibody of c).

Item 9. The monoclonal antibody according to item 8, comprising:
  a) a VH region comprising an amino acid sequence which is at least 60%, 65% or 70%, preferably at least 75% or 80%, more preferably at least 85%, 90%, 91%, 92%, 93%, 94%, and most preferably 95%, 96%, 97%, 98%, or 99% homologous to SEQ ID NO: 7; and a VL region comprising an amino acid sequence which is at least 60%, 65% or 70%, preferably at least 75% or 80%, more preferably at least 85%, 90%, 91%, 92%, 93%, 94%, and most preferably 95%, 96%, 97%, 98%, or 99% homologous to SEQ ID NO: 8; and optionally comprising a VH-CDR1 as depicted in SEQ ID NO: 1, a VH-CDR2 as depicted in SEQ ID NO: 2, and a VH-CDR3 as depicted in SEQ ID NO: 3, and optionally comprising a VL-CDR1 as depicted in SEQ ID NO: 4, a VL-CDR2 as depicted in SEQ ID NO: 5, and a VL-CDR3 as depicted in SEQ ID NO: 6;
  b) a VH region comprising an amino acid sequence which is at least 60%, 65% or 70%, preferably at least 75% or 80%, more preferably at least 85%, 90%, 91%, 92%, 93%, 94%, and most preferably 95%, 96%, 97%, 98%, or 99% homologous to SEQ ID NO: 17; and a VL region comprising an amino acid sequence which is at least 60%, 65% or 70%, preferably at least 75% or 80%, more preferably at least 85%, 90%, 91%, 92%, 93%, 94%, and most preferably 95%, 96%, 97%, 98%, or 99% homologous to SEQ ID NO: 18; and optionally comprising a VH region comprising a VH-CDR1 as depicted in SEQ ID NO: 11, a VH-CDR2 as depicted in SEQ ID NO: 12, and a VH-CDR3 as depicted in SEQ ID NO: 13, and a VL region comprising a VL-CDR1 as depicted in SEQ ID NO: 14, a VL-CDR2 as depicted in SEQ ID NO: 15, and a VL-CDR3 as depicted in SEQ ID NO: 16; or
  c) a VH region comprising an amino acid sequence which is at least 60%, 65% or 70%, preferably at least 75% or 80%, more preferably at least 85%, 90%, 91%, 92%, 93%, 94%, and most preferably 95%, 96%, 97%, 98%, or 99% homologous to SEQ ID NO: 27; and a VL region comprising an amino acid sequence which is at least 60%, 65% or 70%, preferably at least 75% or 80%, more preferably at least 85%, 90%, 91%, 92%, 93%, 94%, and most preferably 95%, 96%, 97%, 98%, or 99% homologous to SEQ ID NO: 28; and optionally comprising a VH region comprising a VH-CDR1 as depicted in SEQ ID NO: 21, a VH-CDR2 as depicted in SEQ ID NO: 22, and a VH-CDR3 as depicted in SEQ ID NO: 23, and a VL region comprising a VL-CDR1 as depicted in SEQ ID NO: 24, a VL-CDR2 as depicted in SEQ ID NO: 25, and a VL-CDR3 as depicted in SEQ ID NO: 26;

Item 10. The monoclonal antibody according to item 8, wherein the monoclonal antibody:
  a) comprises a VH region as depicted in any one of SEQ ID NOs: 7, 17 or 27;
  b) comprises a VL region as depicted in any one of SEQ ID NOs: 8, 18 or 28;
  c) comprises a VH region as depicted in SEQ ID NO: 7 and a VL region as depicted in SEQ ID NO: 8;
  d) comprises a VH region as depicted in SEQ ID NO: 17 and a VL region as depicted in SEQ ID NO: 18;
  e) comprises a VH region as depicted in SEQ ID NO: 27 and a VL region as depicted in SEQ ID NO: 28;
  f) binds to the same sBCMA epitope as the antibody of c) or competes for binding to sBCMA with the antibody of c);
  g) binds to the same sBCMA epitope as the antibody of d) or competes for binding to sBCMA with the antibody of d); or
  h) binds to the same sBCMA epitope as the antibody of e) or competes for binding to sBCMA with the antibody of e).

Item 11. The monoclonal antibody according to any one of items 7 to 10, wherein the binding to the sBCMA epitope is determined via epitope mapping with chimeric or mutated BCMA molecules, site-directed mutagenesis (e.g. alanine scanning), high-throughput shotgun mutagenesis epitope mapping, cross-linking-coupled mass spectrometry, X-ray co-crystallography, cryogenic electron microscopy, and hydrogen-deuterium exchange.

Item 12. The monoclonal antibody according to any one of items 7 to 10, wherein the competition for binding to sBCMA is determined in a competitive ELISA assay, in an Octet competition assay (as described in Example 2 herein) or in a competition assay using avidin-coupled microparticles.

Item 13. The monoclonal antibody according to any one of items 7 to 10 or 12, wherein the competition for binding to sBCMA is defined as a competition occurring between the two tested antibodies of at least 20%, at least 30%, at least 40%, at least 50%, at least 60%, at least 70%, at least 80% or at least 90%.

Item 14. The monoclonal antibody according to any one of the preceding items, which is an IgG, IgD, IgE, IgM or IgA antibody, preferably an IgG antibody, such as an IgG1, IgG2, IgG3 or IgG4 antibody.

Item 15. The monoclonal antibody according to any one of the preceding items, wherein the monoclonal antibody and/or the second monoclonal antibody bind(s) to sBCMA in a biological sample, preferably a human biological sample, such as a (human) serum sample, a (human) plasma sample, a (human) blood sample, a (human) bone marrow sample, a (human) tissue sample, or supernatant obtained from a cell culture of (human) bone marrow mononuclear cells or (human) peripheral blood mononuclear cells.

Item 16. A polynucleotide encoding a monoclonal antibody as defined in any one of the preceding items.

Item 17. A vector comprising the polynucleotide as defined in item 16.

Item 18. A host cell transformed or transfected with the polynucleotide as defined in item 16 or with the vector as defined in item 17.

Item 19. A process for producing a monoclonal antibody as defined in any one of items 1 to 15, said process comprising culturing a host cell as defined in item 18 under conditions allowing the expression of said monoclonal antibody and recovering the produced monoclonal antibody from the culture.

Item 20. A composition comprising a monoclonal antibody as defined in any one of items 1 to 15, or produced according to the process of item 19.

Item 21. A detection system comprising:
  a) a first monoclonal antibody which binds to sBCMA, and
  b) a second monoclonal antibody a first monoclonal to sBCMA, wherein the binding of the first monoclonal antibody to sBCMA occurs in the presence of the second monoclonal antibody binding to sBCMA, and/or wherein the binding of the second monoclonal antibody to sBCMA occurs in the presence of the first monoclonal antibody binding to sBCMA.

Item 22. The detection system according to item 21, wherein sBCMA has the amino acid sequence as depicted in SEQ ID NO: 34.

Item 23. The detection system according to item 21 or 22, wherein the binding of the first monoclonal antibody to sBCMA and the binding of the second monoclonal antibody to sBCMA occur in the presence of a third antibody or antibody construct binding to sBCMA.

Item 24. The detection system according to item 23, wherein the third antibody or antibody construct binds to epitope cluster 3 of BCMA, preferably to epitope cluster 3 of human BCMA, preferably having an amino acid sequence as depicted in SEQ ID NO: 35.

Item 25. The detection system according to any one of items 21 to 24, wherein the first monoclonal antibody and/or the second monoclonal antibody comprise(s) a rabbit VH region and/or a rabbit VL region.

Item 26. The detection system according to any one of items 21 to 25, wherein the first monoclonal antibody and/or the second monoclonal antibody has an affinity (KD) to sBCMA of about $\leq 10^{-7}$ M, $\leq 10^{-8}$ M, $\leq 10^{-9}$ M, or $\leq 10^{-10}$ M.

Item 27. The detection system according to any one of items 21 to 26, wherein the first monoclonal antibody:
  a) comprises a VH region comprising a VH-CDR1 as depicted in SEQ ID NO: 1, a VH-CDR2 as depicted in SEQ ID NO: 2, and a VH-CDR3 as depicted in SEQ ID NO: 3, and a VL region comprising a VL-CDR1 as depicted in SEQ ID NO: 4, a VL-CDR2 as depicted in SEQ ID NO: 5, and a VL-CDR3 as depicted in SEQ ID NO: 6;
  b) comprises a VH region comprising a VH-CDR1 as depicted in SEQ ID NO: 11, a VH-CDR2 as depicted in SEQ ID NO: 12, and a VH-CDR3 as depicted in SEQ ID NO: 13, and a VL region comprising a VL-CDR1 as depicted in SEQ ID NO: 14, a VL-CDR2 as depicted in SEQ ID NO: 15, and a VL-CDR3 as depicted in SEQ ID NO: 16; or
  c) binds to the same sBCMA epitope as the antibody of a) or b), or competes for binding to sBCMA with the antibody of a) or b); and/or wherein the second monoclonal antibody:
  d) comprises a VH region comprising a VH-CDR1 as depicted in SEQ ID NO: 21, a VH-CDR2 as depicted in SEQ ID NO: 22, and a VH-CDR3 as depicted in SEQ ID NO: 23, and a VL region comprising a VL-CDR1 as depicted in SEQ ID NO: 24, a VL-CDR2 as depicted in SEQ ID NO: 25, and a VL-CDR3 as depicted in SEQ ID NO: 26; or
  e) binds to the same sBCMA epitope as the antibody of d) or competes for binding to sBCMA with the antibody of d).

Item 28. The detection system according to item 27, wherein the first monoclonal antibody:
a) comprises a VH region as depicted in SEQ ID NO: 7 or 17;
b) comprises a VL region as depicted in SEQ ID NO: 8 or 18;
c) comprises a VH region as depicted in SEQ ID NO: 7 and a VL region as depicted in SEQ ID NO: 8;
d) comprises a VH region as depicted in SEQ ID NO: 17 and a VL region as depicted in SEQ ID NO: 18; or
e) binds to the same sBCMA epitope as the antibody of c) or d), or competes for binding to sBCMA with the antibody of c) or d); and/or wherein the second monoclonal antibody:
f) comprises a VH region as depicted in SEQ ID NO: 27;
g) comprises a VL region as depicted in SEQ ID NO: 28;
h) comprises a VH region as depicted in SEQ ID NO: 27 and a VL region as depicted in SEQ ID NO: 28; or
i) binds to the same sBCMA epitope as the antibody of h) or competes for binding to sBCMA with the antibody of h).

Item 29. The detection system according to any one of items 21 to 28, wherein the first monoclonal antibody and/or the second monoclonal antibody is/are an IgG, IgD, IgE, IgM or IgA antibody, preferably an IgG antibody, such as an IgG1, IgG2, IgG3 or IgG4 antibody.

Item 30. The detection system according to any one of items 21 to 29, wherein the first monoclonal antibody is used as capture antibody, and the second monoclonal antibody is used as detection antibody, or wherein the first monoclonal antibody is used as detection antibody, and the second monoclonal antibody is used as capture antibody.

Item 31. Use of a monoclonal antibody of any one of items 1 to 15 or of the detection system of any one of items 21 to 30 for:
detecting sBCMA in a sample;
quantifying sBCMA in a sample;
diagnosing a disease associated with sBCMA or increased sBCMA;
stratifying patients diagnosed with a disease associated with sBCMA or increased sBCMA;
monitoring the progression of a disease associated with sBCMA or increased sBCMA; or
monitoring the response to treatment of a disease associated with sBCMA or increased sBCMA.

Item 32. A method for detecting and/or quantifying sBCMA in a sample, comprising the steps of:
(a) using a monoclonal antibody (or antibody construct) of any one of items 1 to 15, or using a detection system of any one of items 21 to 30, for determining the content of sBCMA in a sample; and
(b) comparing the content of sBCMA determined in step (a) to
(i) a pre-defined value for the sBCMA content,
(ii) the content of sBCMA determined in a control sample, or
(iii) the content of sBCMA determined in a sample obtained from the same source or subject at a previous time point.

Item 33. A method for diagnosing a disease associated with sBCMA or increased sBCMA, comprising the steps of:
(a) using a monoclonal antibody (or antibody construct) of any one of items 1 to 15, or using a detection system of any one of items 21 to 30, for determining the content of sBCMA in a sample; and
(b) comparing the content of sBCMA determined in step (a) to
(i) a pre-defined cut-off value for the sBCMA content, indicating absence of such disease, or
(ii) the content of sBCMA determined in a control sample representing absence of such disease,
wherein a higher content of sBCMA determined in step (a) as compared to the pre-defined cut-off value of (i) or the content of sBCMA determined in the control sample of (ii) indicates the presence of a disease associated with sBCMA or increased sBCMA.

Item 34. A method for monitoring the progression of a disease associated with sBCMA or increased sBCMA or for monitoring the response to treatment of a disease associated with sBCMA or increased sBCMA, comprising the steps of:
(a) using a monoclonal antibody (or antibody construct) of any one of items 1 to 15, or using a detection system of any one of items 21 to 30, for determining the content of sBCMA at a first time point in a biological sample obtained from a subject diagnosed with such disease;
(b) using a monoclonal antibody (or antibody construct) of any one of items 1 to 15, or using a detection system of any one of items 21 to 30, for determining the content of sBCMA at a second time point or after treatment in a biological sample obtained from the subject; and
(c) comparing the content of sBCMA determined in step (a) to the content of sBCMA determined in step (b);
wherein a higher content of sBCMA determined in step (a) as compared to the content of sBCMA determined in step (b) indicates that the disease is progressing, and/or wherein a lower content of sBCMA determined in step (a) as compared to the content of sBCMA determined in step (b) indicates that said disease is entering remission or that said disease is responding to the treatment.

Item 35. The use of item 31 or the method of any one of items 32 to 34, wherein the sample is a biological sample, preferably a human biological sample, such as a serum sample, a plasma sample, a blood sample, a bone marrow sample, a tissue sample, or supernatant obtained from a cell culture of bone marrow mononuclear cells or peripheral blood mononuclear cells.

Item 36. The use of item 31 or 35 or the method of any one of items 32 to 35, wherein the sample is obtained from a human subject, preferably a human subject suspected of having or having a disease associated with sBCMA or increased sBCMA, or a subject having received treatment for a disease associated with sBCMA or increased sBCMA.

Item 37. The use of any one of items 31, 35 or 36 or the method of any one of items 32 to 36, wherein the disease is selected from the group consisting of multiple myeloma, relapsed and/or refractory multiple myeloma, heavy chain multiple myeloma, light chain multiple myeloma, extramedullary myeloma (extramedullary plasmacytoma, extramedullary multiple myeloma), plasmacytoma, plasma cell leukemia, Waldenstrom's macroglobulinemia (lymphoplasmacytic lymphoma), smoldering myeloma (smoldering multiple myeloma), chronic lymphocytic leukemia (CLL), primary CNS lymphoma (PCNSL) and B-cell non-Hodgkin lymphoma (B-NHL).

As used herein, the singular forms "a", "an", and "the" include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within ±20%, preferably within ±15%, more preferably within ±10%, and most preferably within ±5% of a given value or range. It also includes the concrete value, e.g., "about 50" includes the value "50".

Throughout this specification and the claims, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein, any of the terms "comprising", "consisting essentially of" and "consisting of" may be replaced with either of the other two terms.

It should be understood that the above description and the below examples provide exemplary arrangemens, but the present invention is not limited to the particular methodologies, techniques, protocols, material, reagents, substances, etc., described herein and as such can vary. The terminology used herein is for the purpose of describing particular embodiments only, and is not intended to limit the scope of the present invention, which is defined solely by the claims. Aspects of the invention are provided in the independent claims. Some optional features of the invention are provided in the dependent claims.

All publications and patents cited throughout the text of this specification (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

A better understanding of the present invention and of its advantages will be obtained from the following examples, offered for illustrative purposes only. The examples are not intended and should not be construed as to limit the scope of the present invention in any way.

EXAMPLES

Example 1

Generation of Rabbit Monoclonal Anti-sBCMA Sandwiching mAbs

The aim of the present efforts was to generate a non-interfering antibody pair ("sandwich pair") to detect sBCMA, even in the presence of a therapeutic anti-BCMA antibody or antibody construct, such as "Ther-Ab1" or "Ther-Ab2" or other antibodies/antibody constructs, such as those having the same or similar CDRs and/or binding to the same epitope within sBCMA. Ther-Ab2 is a CD3xBCMA bispecific half-life extended antibody construct which was previously shown to bind to epitope cluster 3 (SEQ ID NO: 35) of the BCMA extracellular domain, see WO 2013/072406. Ther-Ab1 has an IgG1 format and was presently shown to interfere with BCMA detection/quantitation using a commercial ELISA kit (R&D systems goat polyclonal antibody BCMA capture and detect), see FIG. 1A). Ther-Ab1 is disclosed in WO 2014/089335 as having the following amino acid sequences: VH-CDRs (SEQ ID NOs: 4-6), VL-CDRs (SEQ ID NOs: 106-108), VH (SEQ ID NO: 206), VL (SEQ ID NO: 240) of WO 2014/089335.

In a next step, about 400 XenoMouse® hybridomas were generated against BCMA and tested positive in an ELISA assay for binding to BCMA. However, screening these XenoMouse® hybridomas did not identify any Ther-Ab1 sandwiching antibodies, even when using different Octet formats (see FIG. 1B).

In a subsequent step, rabbit immunization campaigns were carried out with a chimeric protein comprising BCMA as immunogen. The rabbit sera were screened for sandwiching with Ther-Ab1. The following materials were used:

Streptavidin biosensors (Pall ForteBio 18-5021)
Biotinylated BCMA
Ther-Ab 1
Rabbit terminal bleeds
Rabbit irrelevant IgG (Abcam 172730)
384 well flat bottom black polypropylene microplate (Greiner BioOne 781209)
96 well flat bottom black polypropylene microplate (Greiner BioOne 655209)
ForteBio Octet HTX
Octet assay buffer (10 mM Tris, 0.1% Triton, 150 mM NaCl, 1 mM $CaCl_2$, 0.1 mg/mL BSA, pH7.4)

All samples were prepared in Octet assay buffer. Ther-Ab1 and rabbit irrelevant IgG were prepared at 10 µg/ml and Biotin-BCMA at 0.15 µg/ml. Samples were added to a 384 well plate at 80 µL/well. The biosensors were preincubated in 200 µL of Octet buffer using the 96 well plates.

The assay was set up on the ForteBio HTX to run as follows (see also FIG. 1C)):
1. Baseline (octet buffer, 60 seconds)
2. Loading (Biotin-BCMA, 300 seconds)
3. Association (Ther-Ab1, 900 seconds)
4. Baseline (octet buffer, 60 seconds)
5. Sandwich antibody (rabbit sera or irrelevant IgG antibody, 300 seconds)

The reporter point analysis function on the Octet was used to determine the binding signal in the antibody sandwich step. Antibody sandwich step was first aligned to zero so that the signal calculated was the absolute value. Ther-Ab1 sandwiching antibodies were confirmed in rabbit sera by Octet.

After further enrichment of rabbit-derived cells that bind to BCMA, another Octet BCMA sandwich assay was carried out with Ther-Ab2, confirming the existence of Ther-Ab2 sandwiching antibodies.

Finally, three new rabbit anti-sBCMA antibodies were identified (sBCMA-mAb1, sBCMA-mAb2, and sBCMA-mAb3), and their heavy and light chain variable regions were sequenced. In the following assays, these antibodies were characterized in more detail.

Example 2

Characterization of Rabbit Monoclonal Anti-sBCMA Sandwiching mAbs in Octet Assays a) Purified recombinant antibodies sBCMA-mAb1 and sBCMA-mAb2 were screened for sandwiching with Ther-Ab2. The following materials were used:

Anti-huFc (kinetic) biosensors (Pall ForteBio 18-5064)
BCMA
Ther-Ab2
Irrelevant (CD3 x target-X) bispecific antibody construct (differing from Ther-Ab2 only in the target binding domain)
sBCMA-mAb2 unpurified but quantified supernatant
sBCMA-mAb1
Rabbit irrelevant IgG (Abcam 172730)
384 well tilted bottom black polypropylene microplate (ForteBio 18-5080)
96 well flat bottom black polypropylene microplate (GreinerBioOne 655209)
ForteBio Octet HTX
Octet assay buffer (10 mM Tris,0.1% Triton, 150 mM NaCl, 1 mM $CaCl_2$, 0.1 mg/mL BSA, pH7.4)

All samples were prepared in Octet assay buffer. Test antibodies, rabbit irrelevant IgG and irrelevant bispecific antibody construct were prepared at 5 µg/mL. BCMA was prepared at 2 µg/mL. Samples were added to the 384 well plate at 60 µL/well. The biosensors were preincubated in 200 µL of Octet buffer using the 96 well plates.

The assay was set up on the ForteBio HTX to run as follows:

1. Baseline (Octet buffer, 60 seconds)
2. First antibody loading (Ther-Ab2 or irrelevant bispecific antibody construct, 120 seconds)
3. Activation (BCMA, 120 seconds)
4. Baseline (Octet buffer, 60 seconds)
5. Second antibody (sBCMA-mAb2, sBCMA-mAb1 or irrelevant Rabbit antibody, 120 seconds)

The reporter point analysis function on the Octet was used to determine the binding signal in the second antibody step. The second antibody step was first aligned to zero so that the signal calculated is the absolute value. Results are shown in FIG. 2. The rabbit anti-sBCMA antibodies sBCMA-mAb1 and sBCMA-mAb2 were shown to sandwich with Ther-Ab2.

b) In line with the assay described in Example 2a), further Octet assays were carried out. The following set-up demonstrated that antibodies sBCMA-mAb1 and sBCMA-mAb2 share a similar sBCMA epitope (competition assay):

1. Baseline (Octet buffer)
2. First antibody loading (Ther-Ab2)
3. Activation (BCMA)
4. Baseline (Octet buffer)
5. Rabbit antibody 1 (sBCMA-mAb1, sBCMA-mAb2 or irrelevant rabbit IgG antibody, see below table 2)
6. Rabbit antibody 2 (sBCMA-mAb2, sBCMA-mAb1 or irrelevant rabbit IgG antibody, see below table 2)

TABLE 2

Combinations of rabbit antibodies 1 and 2 in different experimental approaches (1-9)

| Assay | Rb antibody 1 | Rb antibody 2 |
|---|---|---|
| 1 | sBCMA-mAb1 | sBCMA-mAb1 |
| 2 | sBCMA-mAb1 | sBCMA-mAb2 |
| 3 | sBCMA-mAb1 | irr Rb IgG |
| 4 | sBCMA-mAb2 | sBCMA-mAb1 |
| 5 | sBCMA-mAb2 | sBCMA-mAb2 |
| 6 | sBCMA-mAb2 | irr Rb IgG |
| 7 | irr Rb-IgG | sBCMA-mAb1 |
| 8 | irr Rb-IgG | sBCMA-mAb2 |
| 9 | irr Rb-IgG | irr Rb IgG | c) Notably, only one out of the 226 rabbit antibodies against sBCMA was able to sandwich with Ther-Ab2 and sBCMA-mAb1, namely, sBCMA-mAb3. This was demonstrated in an Octet sandwich assay comprising the following steps:

1. Capture B-goat anti-rabbit Fc on SA Octet sensor
2. Bind sBCMA-mAb1
3. Block sensor with irrelevant IgG
4. Bind either Ther-Ab2 or irrelevant bispecific antibody construct+/−BCMA
5. Bind sBCMA-mAb3

Figure 3:
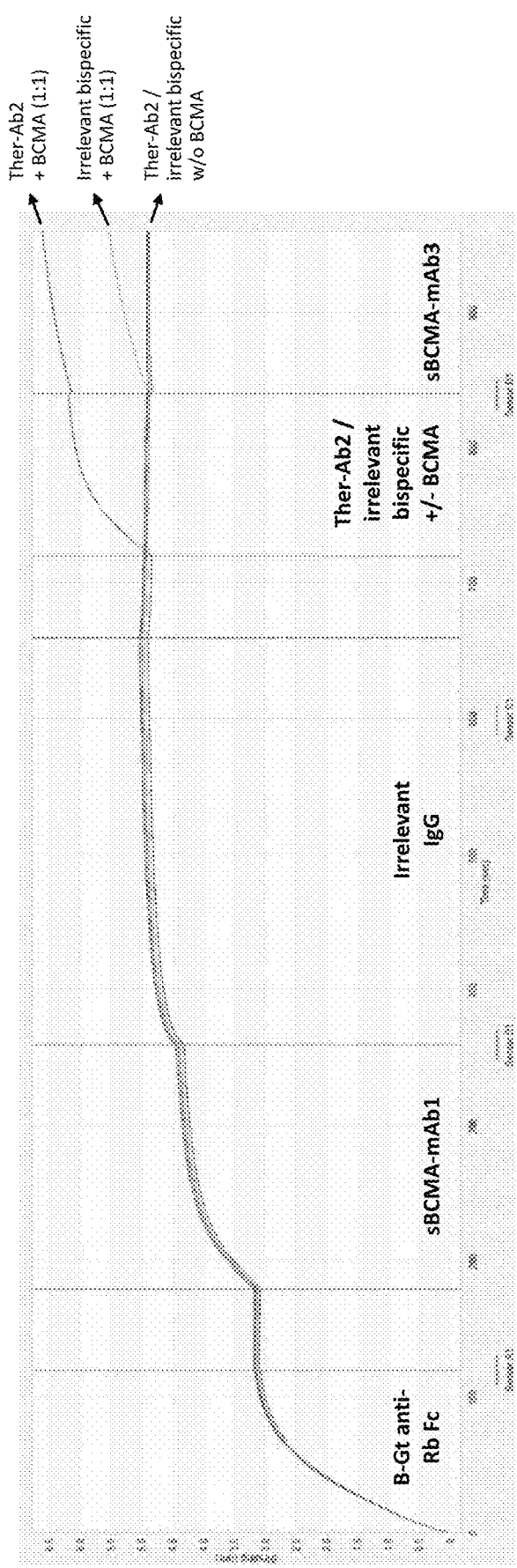
FIG. 3 shows the results of an Octet assay demonstrating that rabbit monoclonal anti-sBCMA-mAb3 is able to sandwich with sBCMA-mAb1 and therapeutic anti-BCMA antibody Ther-Ab2 (see Example 2c).

The results are shown in FIG. 3. They were confirmed in a further assay using sBCMA-mAb1 and sBCMA-mAb3 as purified recombinant antibodies and comprising the following Octet sandwich steps:

1. Capture B-goat anti-rabbit Fc on SA Octet sensor
2. Bind sBCMA-mAb1
3. Block sensor with irrelevant IgG
4. Bind+/−BCMA
5. Bind Ther-Ab2
6. Bind sBCMA-mAb3

Figure 4:
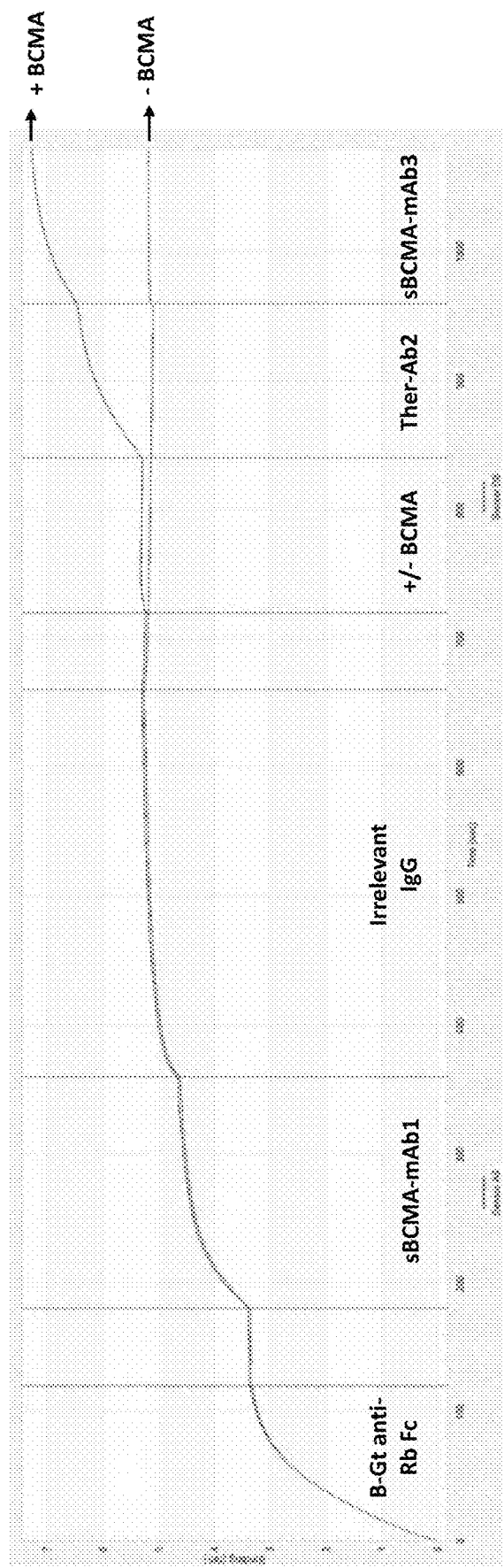
FIG. 4 shows the results of an Octet assay confirming the outcome shown in FIG. 3 (see Example 2c).

The results are shown in FIG. 4. Replacing sBCMA-mAb1 by an irrelevant IgG in step 2 did not lead to any signal in the assay after further addition of BCMA, Ther-Ab2 and sBCMA-mAb3 (negative control).

d) The following set-up demonstrated that the optimal sBCMA/Ther-Ab2 sandwich—in terms of minimal interference with Ther-Ab2—is to capture with sBCMA-mAb1 and to detect with sBCMA-mAb3:

1. Capture B-goat anti-rabbit Fc on SA Octet sensor
2. Bind sBCMA-mAb1 (set-up 1) or bind sBCMA-mAb3 (set-up 2)
3. Block sensor with irrelevant IgG
4. Bind+/−BCMA
5. Bind Ther-Ab2
6. Bind sBCMA-mAb3 (set-up 1) or bind sBCMA-mAb1 (set-up 2)

The signal difference between a set-up with and without BCMA was more pronounced when using sBCMA-mAb1 as capture antibody compared with using sBCMA-mAb3 as capture antibody.

Example 3

Affinity Determination of Rabbit Monoclonal Anti-sBCMA Sandwiching mAbs

Binding affinity profiles were measured for the following rabbit monoclonal anti-sBCMA sandwiching mAbs:
sBCMA-mAb1 (stock concentration 1.43 mg/ml)
sBCMA-mAb2 (stock concentration 2.251 mg/ml)
sBCMA-mAb3 (stock concentration 0.78 mg/ml)

Experiments were performed using a surface plasmon resonance assay (BIACORE™)3000 (GE Healthcare) at 25° C. The running buffer was HBS-P (10 mM HEPES, pH7.4, 150 mM NaCl, 0.05% Surfactant P-20)+0.1% BSA, and kinetics were performed at a high flowrate (100 μl/min). 10 mM Glycine, pH 1.7 was used for regeneration.

Surface preparation: A goat anti-rabbit IgG Fc (Prod. #111-005-046 from Jackson Research) was diluted 1/20 in NaAcetate, pH 5 and covalently coupled to the sample and reference Fc (Fc 1) of a CM5 sensor chip using amine coupling. Individual mAbs were diluted in HBS-P+0.1% BSA and captured on either Fc 2, 3, or 4 at 0.3 μg/ml for kinetic analysis of binding to sBCMA.

Interaction Parameters: sBCMA (1.19 mg/ml stock) was injected as analyte at 600 nM, 300 nM, 150 nM, 75 nM, 37.5 nM, 18.8 nM, and 9.4 nM with the 75 nM concentrated run twice to gage reproducibility. The association rate was monitored for 2.5 minutes. The dissociation time was 20 minutes to determine more accurate kinetics for those mAbs with slower off-rates. The data was double background referenced in that both a reference Fc and a 0 nM analyte concentration were subtracted from the data. A 1:1 Langmuir binding model with mass transfer was used from the surface plasmon resonance assay (BIACORE™) evaluation software.

Figure 5:
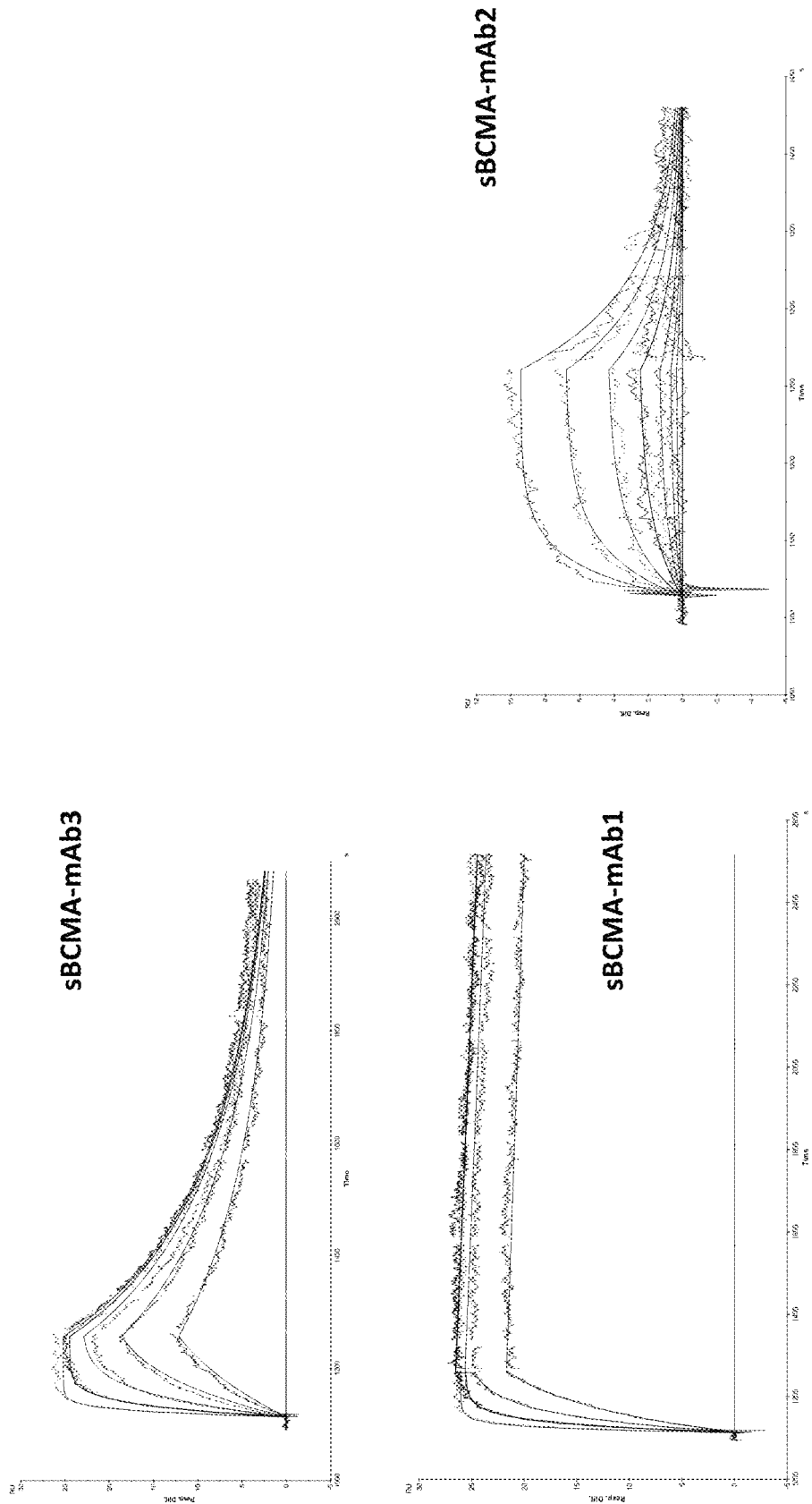
FIG. 5 shows the results of the affinity determination of rabbit monoclonal anti-sBCMA sandwiching mAbs (sBCMA-mAb1, -mAb2 and -mAb3) via surface plasmon resonance (BIACORE™)(see Example 3).

Results are shown in FIG. 5 and in the following Table 3:

TABLE 3

Affinity determination of rabbit monoclonal anti-sBCMA sandwiching mAbs

| mAb | KD (M) | ka (1/Ms) | kd (1/s) |
|---|---|---|---|
| sBCMA-mAb1 | $1.03 \times 10^{-10}$ | $6.3 \times 10^{5}$ | $6.47 \times 10^{-5}$ |
| sBCMA-mAb2 | $3.77 \times 10^{-7}$ | $4.92 \times 10^{4}$ | 0.0185 |
| sBCMA-mAb3 | $4.5 \times 10^{-9}$ | $9.01 \times 10^{5}$ | $4.05 \times 10^{-3}$ |

TABLE 4

Sequence table

| SEQ ID NO | Designation | Format / source | Amino acid sequence |
|---|---|---|---|
| 1 | sBCMA-mAb1 | VH-CDR1 | SGYYIC |
| 2 | | VH-CDR2 | CIYTGSSGSTDYASWAKG |
| 3 | | VH-CDR3 | DYGHSYWNL |
| 4 | | VL-CDR1 | QASEDISSRLA |
| 5 | | VL-CDR2 | AASTLAS |
| 6 | | VL-CDR3 | LGDYYVSSYGNA |
| 7 | | VH | QSLEESGGDLVKPGAFLTLTCTASGFSFSSGYYICWVRQAPGKGLEWIACIYTGSSGSTDYASWAKGRFTISKTSSTTVTLQMTSLTAADTATYFCARDYGHSYWNLWGPGTLVTVSS |
| 8 | | VL | DIVMTQTPASVEAAVGGTVTIKCQASEDISSRLAWYQQKPGQPPKLLIGAASTLASGVSSRFKGSRSGTEYTLTISDLECADAATYYCLGDYYVSSYGNAFGGGTEVVVK |
| 9 | | H | QSLEESGGDLVKPGAFLTLTCTASGFSFSSGYYICWVRQAPGKGLEWIACIYTGSSGSTDYASWAKGRFTISKTSSTTVTLQMTSLTAADTATYFCARDYGHSYWNLWGPGTLVTVSSGQPKAPSVFPLAPCCGDTPSSTVTLGCLVKGYLPEPVTVTWNSGTLTNGVRTFPSVRQSSGLYSLSSVVSVTSSSQPVTCNVAHPATNTKVDKTVAPSTCSKPTCPPPELLGGPSVFIFPPKPKDTLMISRTPEVTCVVVDVSQDDPEVQFTWYINNEQVRTARPPLREQQFNSTIRVVSTLPIAHQDWLRGKEFKCKVHNKALPAPIEKTISKARGQPLEPKVYTMGPPREELSSRSVSLTCMINGFYPSDISVEWEKNGKAEDNYKTTPAVLDSDGSYFLYSKLSVPTSEWQRGDVFTCSVMHEALHNHYTQKSISRSPGK |
| 10 | | L | DIVMTQTPASVEAAVGGTVTIKCQASEDISSRLAWYQQKPGQPPKLLIGAASTLASGVSSRFKGSRSGTEYTLTISDLECADAATYYCLGDYYVSSYGNAFGGGTEVVVKGDPVAPTVLLFPPSSDEVATGTVTIVCVANKYFPDVTVTWEVDGTTQTTGIENSKTPQNSADCTYNLSSTLTLTSTQYNSHKEYTCKVTQGTTSVVQSFSRKNC |
| 11 | sBCMA-mAb2 | VH-CDR1 | SSYWIC |
| 12 | | VH-CDR2 | CIYAGSGDFTYYASWAKG |
| 13 | | VH-CDR3 | DAATSYYSHYFTL |
| 14 | | VL-CDR1 | QASQSIYSGLA |
| 15 | | VL-CDR2 | DASDLAS |
| 16 | | VL-CDR3 | QVTHYESGVP |

TABLE 4-continued

Sequence table

| SEQ ID NO | Desig- nation | Format / source | Amino acid sequence |
|---|---|---|---|
| 17 | | VH | QSLEESGGDLVKPGASLTLTCTASGFSFSSSYWICWVRQAPGKGLEWIACI YAGSGDFTYYASWAKGRFTVSKTSSTTVTLQMTSLTAADTATYFCARDAAT SYYSHYFTLWGPGTLVTVSS |
| 18 | | VL | DVVMTQTPASVSEPVGGTVTIKCQASQSIYSGLAWYQQKPGQPPKLLIYDA SDLASGVPSRFSGSGYGTEFTLTISGVQCEDAATYYCQVTHYESGVPLGGG TEVVVE |
| 19 | | H | QSLEESGGDLVKPGASLTLTCTASGFSFSSSYWICWVRQAPGKGLEWIACI YAGSGDFTYYASWAKGRFTVSKTSSTTVTLQMTSLTAADTATYFCARDAAT SYYSHYFTLWGPGTLVTVSSGQPKAPSVFPLAPCCGDTPSSTVTLGCLVKG YLPEPVTVTWNSGTLTNGVRTFPSVRQSSGLYSLSSVVSVTSSSQPVTCNV AHPATNTKVDKTVAPSTCSKPTCPPPELLGGPSVFIFPPKPKDTLMISRTP EVTCVVVDVSQDDPEVQFTWYINNEQVRTARPPLREQQFNSTIRVVSTLPI AHQDWLRGKEFKCKVHNKALPAPIEKTISKARGQPLEPKVYTMGPPREELS SRSVSLTCMINGFYPSDISVEWEKNGKAEDNYKTTPAVLDSDGSYFLYSKL SVPTSEWQRGDVFTCSVMHEALHNHYTQKSISRSPGK |
| 20 | | L | DVVMTQTPASVSEPVGGTVTIKCQASQSIYSGLAWYQQKPGQPPKLLIYDA SDLASGVPSRFSGSGYGTEFTLTISGVQCEDAATYYCQVTHYESGVPLGGG TEVVVEGDPVAPTVLLFPPSSDEVATGTVTIVCVANKYFPDVTVTWEVDGT TQTTGIENSKTPQNSADCTYNLSSTLTLTSTQYNSHKEYTCKVTQGTTSVV QSFSRKNC |
| 21 | sBCMA- mAb3 | VH-CDR1 | SYYYMC |
| 22 | | VH-CDR2 | CIFSDSGGHTAYASWAEG |
| 23 | | VH-CDR3 | DRRDVVYIRDL |
| 24 | | VL-CDR1 | QSSESVYNNNALA |
| 25 | | VL-CDR2 | GASSLAS |
| 26 | | VL-CDR3 | AGYKRYNNDGHA |
| 27 | | VH | QEQLEESGGGLVKPGGTLTLTCKASGMDFSSYYYMCWVRQAPGKGLEWIAC IFSDSGGHTAYASWAEGRFTISKTSSTTVTLQMTSLTVADTATYFCARDRR DVVYIRDLWGPGTLVTVSS |
| 28 | | VL | ALVMTQTPSPVSAAVGGTVTISCQSSESVYNNNALAWYQQKPGQPPKLLIY GASSLASGVPSRFKGSGSGTQFTLTISDLECDDAATYYCAGYKRYNNDGHA FGGGTEVVVK |
| 29 | | H | QEQLEESGGGLVKPGGTLTLTCKASGMDFSSYYYMCWVRQAPGKGLEWIAC IFSDSGGHTAYASWAEGRFTISKTSSTTVTLQMTSLTVADTATYFCARDRR DVVYIRDLWGPGTLVTVSSGQPKAPSVFPLAPCCGDTPSSTVTLGCLVKGY LPEPVTVTWNSGTLTNGVRTFPSVRQSSGLYSLSSVVSVTSSSQPVTCNVA HPATNTKVDKTVAPSTCSKPTCPPPELLGGPSVFIFPPKPKDTLMISRTPE VTCVVVDVSQDDPEVQFTWYINNEQVRTARPPLREQQFNSTIRVVSTLPIA HQDWLRGKEFKCKVHNKALPAPIEKTISKARGQPLEPKVYTMGPPREELSS RSVSLTCMINGFYPSDISVEWEKNGKAEDNYKTTPAVLDSDGSYFLYSKLS VPTSEWQRGDVFTCSVMHEALHNHYTQKSISRSPGK |
| 30 | | L | ALVMTQTPSPVSAAVGGTVTISCQSSESVYNNNALAWYQQKPGQPPKLLTY GASSLASGVPSRFKGSGSGTQFTLTISDLECDDAATYYCAGYKRYNNDGHA EGGGTEVVVKGDPVAPTVLLFPPSSDEVATGTVTIVCVANKYFPDVTVTWE VDGTTQTTGIENSKTPQNSADCTYNLSSTLTLTSTQYNSHKEYTCKVTQGT TSVVQSFSRKNC |
| 31 | Exemplary heavy chain constant region | rabbit | GQPKAPSVFPLAPCCGDTPSSTVTLGCLVKGYLPEPVTVTWNSGTLTNGVR TFPSVRQSSGLYSLSSVVSVTSSSQPVTCNVAHPATNTKVDKTVAPSTCSK PTCPPPELLGGPSVFIFPPKPKDTLMISRTPEVTCVVVDVSQDDPEVQFTW YINNEQVRTARPPLREQQFNSTIRVVSTLPTAHQDWLRGKEFKCKVHNKAL PAPIEKTISKARGQPLEPKVYTMGPPREELSSRSVSLTCMINGFYPSDISV EWEKNGKAEDNYKTTPAVLDSDGSYFLYSKLSVPTSEWQRGDVFTCSVMHE ALHNHYTQKSISRSPGK |
| 32 | Exemplary light chain constant region | rabbit | GDPVAPTVLLFPPSSDEVATGTVTIVCVANKYFPDVTVTWEVDGTTQTTGI ENSKTPQNSADCTYNLSSTLTLTSTQYNSHKEYTCKVTQGTTSVVQSFSRK NC |

TABLE 4-continued

Sequence table

| SEQ ID NO | Designation | Format / source | Amino acid sequence |
|---|---|---|---|
| 33 | BCMA | human | MLQMAGQCSQNEYFDSLLHACIPCQLRCSSNTPPLTCQRYCNASVTNSVKG TNAILWTCLGLSLIISLAVFVLMFLLRKINSEPLKDEFKNTGSGLLGMANI DLEKSRTGDEIILPRGLEYTVEECTCEDCIKSKPKVDSDHCFPLPAMEEGA TILVTTKTNDYCKSLPAALSATEIEKSISAR |
| 34 | BCMA ECD (sBCMA) | human | MLQMAGQCSQNEYFDSLLHACIPCQLRCSSNTPPLTCQRYCNASVTNSVKG TNA |
| 35 | BCMA ECD epitope cluster 3 | human | CQLRCSSNTPPLTCQRYC |

The invention claimed is:

1. A monoclonal antibody that binds to soluble B cell maturation antigen (sBCMA), wherein the antibody comprises:
   a) a VH region comprising a VH-CDR1 as depicted in SEQ ID NO: 1, a VH-CDR2 as depicted in SEQ ID NO: 2, and a VH-CDR3 as depicted in SEQ ID NO: 3, and a VL region comprising a VL-CDR1 as depicted in SEQ ID NO: 4, a VL-CDR2 as depicted in SEQ ID NO: 5, and a VL-CDR3 as depicted in SEQ ID NO: 6;
   b) a VH region comprising a VH-CDR1 as depicted in SEQ ID NO: 11, a VH-CDR2 as depicted in SEQ ID NO: 12, and a VH-CDR3 as depicted in SEQ ID NO: 13, and a VL region comprising a VL-CDR1 as depicted in SEQ ID NO: 14, a VL-CDR2 as depicted in SEQ ID NO: 15, and a VL-CDR3 as depicted in SEQ ID NO: 16; or
   c) a VH region comprising a VH-CDR1 as depicted in SEQ ID NO: 21, a VH-CDR2 as depicted in SEQ ID NO: 22, and a VH-CDR3 as depicted in SEQ ID NO: 23, and a VL region comprising a VL-CDR1 as depicted in SEQ ID NO: 24, a VL-CDR2 as depicted in SEQ ID NO: 25, and a VL-CDR3 as depicted in SEQ ID NO: 26.

2. The monoclonal antibody according to claim 1, wherein sBCMA has the amino acid sequence as depicted in SEQ ID NO: 34.

3. The monoclonal antibody according to claim 1, wherein the binding of the monoclonal antibody to sBCMA occurs in the presence of a second monoclonal antibody binding to sBCMA, and optionally in the presence of a third antibody or antibody construct binding to sBCMA.

4. The monoclonal antibody according to claim 1, wherein the monoclonal antibody comprises a rabbit VH region and/or a rabbit VL region.

5. The monoclonal antibody according to claim 1, wherein the monoclonal antibody has an affinity to sBCMA of about $\leq 10^{-7}$ M, $\leq 10^{-8}$ M, $\leq 10^{-9}$ M, or $\leq 10^{-19}$ M.

6. The monoclonal antibody according to claim 5, wherein the affinity is determined in a surface plasmon resonance assay.

7. The monoclonal antibody according to claim 1, wherein the monoclonal antibody:
   a) binds to the same sBCMA epitope as the antibody comprising a VH region comprising a VH-CDR1 as depicted in SEQ ID NO: 1, a VH-CDR2 as depicted in SEQ ID NO: 2, and a VH-CDR3 as depicted in SEQ ID NO: 3, and a VL region comprising a VL-CDR1 as depicted in SEQ ID NO: 4, a VL-CDR2 as depicted in SEQ ID NO: 5, and a VL-CDR3 as depicted in SEQ ID NO: 6, or competes for binding to sBCMA with the antibody comprising a VH region comprising a VH-CDR1 as depicted in SEQ ID NO: 1, a VH-CDR2 as depicted in SEQ ID NO: 2, and a VH-CDR3 as depicted in SEQ ID NO: 3, and a VL region comprising a VL-CDR1 as depicted in SEQ ID NO: 4, a VL-CDR2 as depicted in SEQ ID NO: 5, and a VL-CDR3 as depicted in SEQ ID NO: 6;

b) binds to the same sBCMA epitope as the antibody comprising a VH region comprising a VH-CDR1 as depicted in SEQ ID NO: 11, a VH-CDR2 as depicted in SEQ ID NO: 12, and a VH-CDR3 as depicted in SEQ ID NO: 13, and a VL region comprising a VL-CDR1 as depicted in SEQ ID NO: 14, a VL-CDR2 as depicted in SEQ ID NO: 15, and a VL-CDR3 as depicted in SEQ ID NO: 16, or competes for binding to sBCMA with the antibody comprising a VH region comprising a VH-CDR1 as depicted in SEQ ID NO: 11, a VH-CDR2 as depicted in SEQ ID NO: 12, and a VH-CDR3 as depicted in SEQ ID NO: 13, and a VL region comprising a VL-CDR1 as depicted in SEQ ID NO: 14, a VL-CDR2 as depicted in SEQ ID NO: 15, and a VL-CDR3 as depicted in SEQ ID NO: 16; or c) binds to the same sBCMA epitope as the antibody comprising a VH region comprising a VH-CDR1 as depicted in SEQ ID NO: 21, a VH-CDR2 as depicted in SEQ ID NO: 22, and a VH-CDR3 as depicted in SEQ ID NO: 23, and a VL region comprising a VL-CDR1 as depicted in SEQ ID NO: 24, a VL-CDR2 as depicted in SEQ ID NO: 25, and a VL-CDR3 as depicted in SEQ ID NO: 26, or competes for binding to sBCMA with the antibody comprising a VH region comprising a VH-CDR1 as depicted in SEQ ID NO: 21, a VH-CDR2 as depicted in SEQ ID NO: 22, and a VH-CDR3 as depicted in SEQ ID NO: 23, and a VL region comprising a VL-CDR1 as depicted in SEQ ID NO: 24, a VL-CDR2 as depicted in SEQ ID NO: 25, and a VL-CDR3 as depicted in SEQ ID NO: 26.

8. The monoclonal antibody according to claim 1, wherein the monoclonal antibody:
a) comprises a VH region as depicted in any one of SEQ ID NOs: 7, 17 or 27;
b) comprises a VL region as depicted in any one of SEQ ID NOs: 8, 18 or 28;
c) comprises a VH region as depicted in SEQ ID NO: 7 and a VL region as depicted in SEQ ID NO: 8;
d) comprises a VH region as depicted in SEQ ID NO: 17 and a VL region as depicted in SEQ ID NO: 18;
e) comprises a VH region as depicted in SEQ ID NO: 27 and a VL region as depicted in SEQ ID NO: 28;
f) binds to the same sBCMA epitope as the antibody of c) or competes for binding to sBCMA with the antibody of c);
g) binds to the same sBCMA epitope as the antibody of d) or competes for binding to sBCMA with the antibody of d); or
h) binds to the same sBCMA epitope as the antibody of e) or competes for binding to sBCMA with the antibody of e).

9. The monoclonal antibody according to claim 1, wherein the antibody is an IgG, IgD, IgE, IgM or IgA antibody.

10. The monoclonal antibody according to claim 3, wherein the monoclonal antibody and/or the second monoclonal antibody bind(s) to sBCMA in a human serum, human plasma or human blood sample.

11. A nucleic acid comprising a polynucleotide encoding the monoclonal antibody of claim 1.

12. A vector comprising the nucleic acid of claim 11.

13. A host cell transformed or transfected with the nucleic acid of claim 12.

14. A process for producing a monoclonal antibody, said process comprising culturing the host cell of claim 13 under conditions allowing the expression of said monoclonal antibody and recovering the produced monoclonal antibody from the culture.

15. A composition comprising the monoclonal antibody of claim 1.

16. A detection system comprising
a) a first monoclonal antibody which binds to soluble B cell maturation antigen (sBCMA), and
b) a second monoclonal antibody which binds to sBCMA, wherein the first monoclonal antibody comprises:
i) a VH region comprising a VH-CDR1 as depicted in SEQ ID NO: 1, a VH-CDR2 as depicted in SEQ ID NO: 2, and a VH-CDR3 as depicted in SEQ ID NO: 3, and a VL region comprising a VL-CDR1 as depicted in SEQ ID NO: 4, a VL-CDR2 as depicted in SEQ ID NO: 5, and a VL-CDR3 as depicted in SEQ ID NO: 6; or
ii) a VH region comprising a VH-CDR1 as depicted in SEQ ID NO: 11, a VH-CDR2 as depicted in SEQ ID NO: 12, and a VH-CDR3 as depicted in SEQ ID NO: 13, and a VL region comprising a VL-CDR1 as depicted in SEQ ID NO: 14, a VL-CDR2 as depicted in SEQ ID NO: 15, and a VL-CDR3 as depicted in SEQ ID NO: 16; and/or
wherein the second monoclonal antibody comprises:
a VH region comprising a VH-CDR1 as depicted in SEQ ID NO: 21, a VH-CDR2 as depicted in SEQ ID NO: 22, and a VH-CDR3 as depicted in SEQ ID NO: 23, and a VL region comprising a VL-CDR1 as depicted in SEQ ID NO: 24, a VL-CDR2 as depicted in SEQ ID NO: 25, and a VL-CDR3 as depicted in SEQ ID NO: 26.

17. The detection system according to claim 16, wherein sBCMA has the amino acid sequence as depicted in SEQ ID NO: 34.

18. The detection system according to claim 16, wherein the binding of the first monoclonal antibody to sBCMA occurs in the presence of the second monoclonal antibody binding to sBCMA, and/or wherein the binding of the second monoclonal antibody to sBCMA occurs in the presence of the first monoclonal antibody binding to sBCMA; and optionally wherein the binding of the first monoclonal antibody to sBCMA and the binding of the second monoclonal antibody to sBCMA occur in the presence of a third antibody or antibody construct binding to sBCMA.

19. The detection system according to claim 16, wherein the first monoclonal antibody and/or the second monoclonal antibody comprise(s) a rabbit VH region and/or a rabbit VL region.

20. The detection system according to claim 16, wherein the first monoclonal antibody and/or the second monoclonal antibody has an affinity to sBCMA of about $\leq 10^{-7}$ M, $\leq 10^{-8}$ M, $\leq 10^{-9}$ M, or $\leq 10^{-10}$ M.

21. The detection system according to claim 16, wherein the first monoclonal antibody
binds to the same sBCMA epitope as the antibody comprising:

a) a VH region comprising a VH-CDR1 as depicted in SEQ ID NO: 1, a VH-CDR2 as depicted in SEQ ID NO: 2, and a VH-CDR3 as depicted in SEQ ID NO: 3, and a VL region comprising a VL-CDR1 as depicted in SEQ ID NO: 4, a VL-CDR2 as depicted in SEQ ID NO: 5, and a VL-CDR3 as depicted in SEQ ID NO: 6; or b) a VH region comprising a VH-CDR1 as depicted in SEQ ID NO: 11, a VH-CDR2 as depicted in SEQ ID NO: 12, and a VH-CDR3 as depicted in SEQ ID NO: 13, and a VL region comprising a VL-CDR1 as depicted in SEQ ID NO: 14, a VL-CDR2 as depicted in SEQ ID NO: 15, and a VL-CDR3 as depicted in SEQ ID NO: 16; or competes for binding to sBCMA with the antibody of a) or b);

and/or wherein the second monoclonal antibody binds to the same sBCMA epitope as the antibody comprising:

a VH region comprising a VH-CDR1 as depicted in SEQ ID NO: 21, a VH-CDR2 as depicted in SEQ ID NO: 22, and a VH-CDR3 as depicted in SEQ ID NO: 23, and a VL region comprising a VL-CDR1 as depicted in SEQ ID NO: 24, a VL-CDR2 as depicted in SEQ ID NO: 25, and a VL-CDR3 as depicted in SEQ ID NO: 26; or competes for binding to sBCMA with the antibody comprising a VH region comprising a VH-CDR1 as depicted in SEQ ID NO: 21, a VH-CDR2 as depicted in SEQ ID NO: 22, and a VH-CDR3 as depicted in SEQ ID NO: 23, and a VL region comprising a VL-CDR1 as depicted in SEQ ID NO: 24, a VL-CDR2 as depicted in SEQ ID NO: 25, and a VL-CDR3 as depicted in SEQ ID NO: 26.

22. The detection system according to claim 16, wherein the first monoclonal antibody:

a) comprises a VH region as depicted in SEQ ID NO: 7 or 17;

b) comprises a VL region as depicted in SEQ ID NO: 8 or 18;

c) comprises a VH region as depicted in SEQ ID NO: 7 and a VL region as depicted in SEQ ID NO: 8;

d) comprises a VH region as depicted in SEQ ID NO: 17 and a VL region as depicted in SEQ ID NO: 18; or e) binds to the same sBCMA epitope as the antibody of c) or d), or competes for binding to sBCMA with the antibody of c) or d);

and/or wherein the second monoclonal antibody:

f) comprises a VH region as depicted in SEQ ID NO: 27;

g) comprises a VL region as depicted in SEQ ID NO: 28;

h) comprises a VH region as depicted in SEQ ID NO: 27 and a VL region as depicted in SEQ ID NO: 28; or i) binds to the same sBCMA epitope as the antibody of h) or competes for binding to sBCMA with the antibody of h).

23. The detection system according to claim 16, wherein the first monoclonal antibody and/or the second monoclonal antibody is/are an IgG, IgD, IgE, IgM or IgA antibody.

24. The detection system according to claim 16, wherein the first monoclonal antibody is used as capture antibody, and the second monoclonal antibody is used as detection antibody, or wherein the first monoclonal antibody is used as detection antibody, and the second monoclonal antibody is used as capture antibody.

25. The monoclonal antibody according to claim 9, wherein the antibody is an IgG antibody.

26. The monoclonal antibody according to claim 25, wherein the IgG antibody is an IgG1, IgG2, IgG3 or IgG4 antibody.

27. The detection system according to claim 23, wherein the first monoclonal antibody and/or the second monoclonal antibody is/are an IgG antibody.

28. The detection system according to claim 27, wherein the IgG antibody is an IgG1, IgG2, IgG3 or IgG4 antibody.

* * * * *

UNITED STATES PATENT AND TRADEMARK OFFICE
CERTIFICATE OF CORRECTION

PATENT NO. : 11,505,614 B2
APPLICATION NO. : 16/585318
DATED : November 22, 2022
INVENTOR(S) : Agnieszka Kielczewska et al.

It is certified that error appears in the above-identified patent and that said Letters Patent is hereby corrected as shown below:

In the Claims

At Column 84, Line 57, "$\leq 10^{-19}$ M." should be -- $\leq 10^{-10}$ M. --.

Signed and Sealed this
Eighth Day of August, 2023

Katherine Kelly Vidal
*Director of the United States Patent and Trademark Office*

SEQUENCE LISTING

<160> NUMBER OF SEQ ID NOS: 35

<210> SEQ ID NO 1
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 1

Ser Gly Tyr Tyr Ile Cys
1               5

<210> SEQ ID NO 2
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 2

Cys Ile Tyr Thr Gly Ser Ser Gly Ser Thr Asp Tyr Ala Ser Trp Ala
1               5                   10                  15

Lys Gly

<210> SEQ ID NO 3
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 3

Asp Tyr Gly His Ser Tyr Trp Asn Leu
1               5

<210> SEQ ID NO 4
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 4

Gln Ala Ser Glu Asp Ile Ser Ser Arg Leu Ala

<210> SEQ ID NO 5
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 5

```
Ala Ala Ser Thr Leu Ala Ser
1               5
```

<210> SEQ ID NO 6
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 6

```
Leu Gly Asp Tyr Tyr Val Ser Ser Tyr Gly Asn Ala
1               5                   10
```

<210> SEQ ID NO 7
<211> LENGTH: 118
<212> TYPE: PRT
<213> ORGANISM: Artificial Sequence
<220> FEATURE:
<223> OTHER INFORMATION: Synthetic Polypeptide

<400> SEQUENCE: 7

```
Gln Ser Leu Glu Glu Ser Gly Gly Asp Leu Val Lys Pro Gly Ala Phe
1               5                   10                  15

Leu Thr Leu Thr Cys Thr Ala Ser Gly Phe Ser Phe Ser Ser Gly Tyr
                20                  25                  30

Tyr Ile Cys Trp Val Arg Gln Ala Pro Gly Lys Gly Leu Glu Trp Ile
            35                  40                  45

Ala Cys Ile Tyr Thr Gly Ser Ser Gly Ser Thr Asp Tyr Ala Ser Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Asp Tyr Gly His Ser Tyr Trp Asn Leu Trp Gly Pro Gly Thr
            100                 105                 110

Leu Val Thr Val Ser Ser
        115
```

<210> SEQ ID NO 8
<211> LENGTH: 110
<212> TYPE: PRT
<213> ORGANISM: Artificial Sequence
<220> FEATURE:
<223> OTHER INFORMATION: Synthetic Polypeptide

<400> SEQUENCE: 8

```
Asp Ile Val Met Thr Gln Thr Pro Ala Ser Val Glu Ala Ala Val Gly
1               5                   10                  15

Gly Thr Val Thr Ile Lys Cys Gln Ala Ser Glu Asp Ile Ser Ser Arg
                20                  25                  30

Leu Ala Trp Tyr Gln Gln Lys Pro Gly Gln Pro Pro Lys Leu Leu Ile
```

```
                35                  40                  45
Gly Ala Ala Ser Thr Leu Ala Ser Gly Val Ser Ser Arg Phe Lys Gly
         50                  55                  60

Ser Arg Ser Gly Thr Glu Tyr Thr Leu Thr Ile Ser Asp Leu Glu Cys
 65                  70                  75                  80

Ala Asp Ala Ala Thr Tyr Tyr Cys Leu Gly Asp Tyr Tyr Val Ser Ser
                 85                  90                  95

Tyr Gly Asn Ala Phe Gly Gly Thr Glu Val Val Val Lys
            100                 105                 110

<210> SEQ ID NO 9
<211> LENGTH: 441
<212> TYPE: PRT
<213> ORGANISM: Artificial Sequence
<220> FEATURE:
<223> OTHER INFORMATION: Synthetic Polypeptide

<400> SEQUENCE: 9

Gln Ser Leu Glu Glu Ser Gly Gly Asp Leu Val Lys Pro Gly Ala Phe
 1               5                  10                  15

Leu Thr Leu Thr Cys Thr Ala Ser Gly Phe Ser Phe Ser Ser Gly Tyr
                20                  25                  30

Tyr Ile Cys Trp Val Arg Gln Ala Pro Gly Lys Gly Leu Glu Trp Ile
             35                  40                  45

Ala Cys Ile Tyr Thr Gly Ser Ser Gly Ser Thr Asp Tyr Ala Ser Trp
 50                  55                  60

Ala Lys Gly Arg Phe Thr Ile Ser Lys Thr Ser Thr Thr Val Thr
 65                  70                  75                  80

Leu Gln Met Thr Ser Leu Thr Ala Ala Asp Thr Ala Thr Tyr Phe Cys
                 85                  90                  95

Ala Arg Asp Tyr Gly His Ser Tyr Trp Asn Leu Trp Gly Pro Gly Thr
            100                 105                 110

Leu Val Thr Val Ser Ser Gly Gln Pro Lys Ala Pro Ser Val Phe Pro
            115                 120                 125

Leu Ala Pro Cys Cys Gly Asp Thr Pro Ser Ser Thr Val Thr Leu Gly
        130                 135                 140

Cys Leu Val Lys Gly Tyr Leu Pro Glu Pro Val Thr Val Thr Trp Asn
145                 150                 155                 160

Ser Gly Thr Leu Thr Asn Gly Val Arg Thr Phe Pro Ser Val Arg Gln
                165                 170                 175

Ser Ser Gly Leu Tyr Ser Leu Ser Ser Val Val Ser Val Thr Ser Ser
            180                 185                 190

Ser Gln Pro Val Thr Cys Asn Val Ala His Pro Ala Thr Asn Thr Lys
        195                 200                 205

Val Asp Lys Thr Val Ala Pro Ser Thr Cys Ser Lys Pro Thr Cys Pro
210                 215                 220

Pro Pro Glu Leu Leu Gly Gly Pro Ser Val Phe Ile Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser Gln Asp Asp Pro Glu Val Gln Phe Thr Trp Tyr
            260                 265                 270

Ile Asn Asn Glu Gln Val Arg Thr Ala Arg Pro Pro Leu Arg Glu Gln
        275                 280                 285

Gln Phe Asn Ser Thr Ile Arg Val Val Ser Thr Leu Pro Ile Ala His
```

```
                    290                 295                 300
Gln Asp Trp Leu Arg Gly Lys Glu Phe Lys Cys Lys Val His Asn Lys
305                 310                 315                 320

Ala Leu Pro Ala Pro Ile Glu Lys Thr Ile Ser Lys Ala Arg Gly Gln
                325                 330                 335

Pro Leu Glu Pro Lys Val Tyr Thr Met Gly Pro Pro Arg Glu Glu Leu
            340                 345                 350

Ser Ser Arg Ser Val Ser Leu Thr Cys Met Ile Asn Gly Phe Tyr Pro
            355                 360                 365

Ser Asp Ile Ser Val Glu Trp Glu Lys Asn Gly Lys Ala Glu Asp Asn
            370                 375                 380

Tyr Lys Thr Thr Pro Ala Val Leu Asp Ser Asp Gly Ser Tyr Phe Leu
385                 390                 395                 400

Tyr Ser Lys Leu Ser Val Pro Thr Ser Glu Trp Gln Arg Gly Asp Val
                405                 410                 415

Phe Thr Cys Ser Val Met His Glu Ala Leu His Asn His Tyr Thr Gln
                420                 425                 430

Lys Ser Ile Ser Arg Ser Pro Gly Lys
            435                 440

<210> SEQ ID NO 10
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 10

Asp Ile Val Met Thr Gln Thr Pro Ala Ser Val Glu Ala Ala Val Gly
1               5                   10                  15

Gly Thr Val Thr Ile Lys Cys Gln Ala Ser Glu Asp Ile Ser Ser Arg
            20                  25                  30

Leu Ala Trp Tyr Gln Gln Lys Pro Gly Gln Pro Pro Lys Leu Leu Ile
        35                  40                  45

Gly Ala Ala Ser Thr Leu Ala Ser Gly Val Ser Ser Arg Phe Lys Gly
50                  55                  60

Ser Arg Ser Gly Thr Glu Tyr Thr Leu Thr Ile Ser Asp Leu Glu Cys
65                  70                  75                  80

Ala Asp Ala Ala Thr Tyr Tyr Cys Leu Gly Asp Tyr Tyr Val Ser Ser
                85                  90                  95

Tyr Gly Asn Ala Phe Gly Gly Gly Thr Glu Val Val Val Lys Gly Asp
            100                 105                 110

Pro Val Ala Pro Thr Val Leu Leu Phe Pro Pro Ser Ser Asp Glu Val
        115                 120                 125

Ala Thr Gly Thr Val Thr Ile Val Cys Val Ala Asn Lys Tyr Phe Pro
130                 135                 140

Asp Val Thr Val Thr Trp Glu Val Asp Gly Thr Thr Gln Thr Thr Gly
145                 150                 155                 160

Ile Glu Asn Ser Lys Thr Pro Gln Asn Ser Ala Asp Cys Thr Tyr Asn
                165                 170                 175

Leu Ser Ser Thr Leu Thr Leu Thr Ser Thr Gln Tyr Asn Ser His Lys
            180                 185                 190

Glu Tyr Thr Cys Lys Val Thr Gln Gly Thr Thr Ser Val Val Gln Ser
        195                 200                 205

Phe Ser Arg Lys Asn Cys
```

-continued

```
<210> SEQ ID NO 11
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 11

Ser Ser Tyr Trp Ile Cys
1               5

<210> SEQ ID NO 12
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 12

Cys Ile Tyr Ala Gly Ser Gly Asp Phe Thr Tyr Tyr Ala Ser Trp Ala
1               5                   10                  15

Lys Gly

<210> SEQ ID NO 13
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 13

Asp Ala Ala Thr Ser Tyr Tyr Ser His Tyr Phe Thr Leu
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 14

Gln Ala Ser Gln Ser Ile Tyr Ser Gly Leu Ala
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 15

Asp Ala Ser Asp Leu Ala Ser
1               5

<210> SEQ ID NO 16
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 16
```

Gln Val Thr His Tyr Glu Ser Gly Val Pro
1               5                   10

<210> SEQ ID NO 17
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 17

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Ser Tyr
                20                  25                  30

Trp Ile Cys Trp Val Arg Gln Ala Pro Gly Lys Gly Leu Glu Trp Ile
            35                  40                  45

Ala Cys Ile Tyr Ala Gly Ser Gly Asp Phe Thr Tyr Tyr Ala Ser Trp
        50                  55                  60

Ala Lys Gly Arg Phe Thr Val Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Asp Ala Ala Thr Ser Tyr Tyr Ser His Tyr Phe Thr Leu Trp
            100                 105                 110

Gly Pro Gly Thr Leu Val Thr Val Ser Ser
        115                 120

<210> SEQ ID NO 18
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 18

Asp Val Val Met Thr Gln Thr Pro Ala Ser Val Ser Glu Pro Val Gly
1               5                   10                  15

Gly Thr Val Thr Ile Lys Cys Gln Ala Ser Gln Ser Ile Tyr Ser Gly
                20                  25                  30

Leu Ala Trp Tyr Gln Gln Lys Pro Gly Gln Pro Pro Lys Leu Leu Ile
            35                  40                  45

Tyr Asp Ala Ser Asp Leu Ala Ser Gly Val Pro Ser Arg Phe Ser Gly
        50                  55                  60

Ser Gly Tyr Gly Thr Glu Phe Thr Leu Thr Ile Ser Gly Val Gln Cys
65                  70                  75                  80

Glu Asp Ala Ala Thr Tyr Tyr Cys Gln Val Thr His Tyr Glu Ser Gly
                85                  90                  95

Val Pro Leu Gly Gly Gly Thr Glu Val Val Val Glu
            100                 105

<210> SEQ ID NO 19
<211> LENGTH: 445
<212> TYPE: PRT
<213> ORGANISM: Artificial Sequence
<220> FEATURE:
<223> OTHER INFORMATION: Synthetic Polypeptide

<400> SEQUENCE: 19

Gln Ser Leu Glu Glu Ser Gly Gly Asp Leu Val Lys Pro Gly Ala Ser

-continued

```
1               5                   10                  15
Leu Thr Leu Thr Cys Thr Ala Ser Gly Phe Ser Phe Ser Ser Ser Tyr
            20                  25                  30

Trp Ile Cys Trp Val Arg Gln Ala Pro Gly Lys Gly Leu Glu Trp Ile
            35                  40                  45

Ala Cys Ile Tyr Ala Gly Ser Gly Asp Phe Thr Tyr Tyr Ala Ser Trp
            50                  55                  60

Ala Lys Gly Arg Phe Thr Val Ser Lys Thr Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Asp Ala Ala Thr Ser Tyr Tyr Ser His Tyr Phe Thr Leu Trp
                100                 105                 110

Gly Pro Gly Thr Leu Val Thr Val Ser Ser Gly Gln Pro Lys Ala Pro
                115                 120                 125

Ser Val Phe Pro Leu Ala Pro Cys Cys Gly Asp Thr Pro Ser Ser Thr
            130                 135                 140

Val Thr Leu Gly Cys Leu Val Lys Gly Tyr Leu Pro Glu Pro Val Thr
145                 150                 155                 160

Val Thr Trp Asn Ser Gly Thr Leu Thr Asn Gly Val Arg Thr Phe Pro
            165                 170                 175

Ser Val Arg Gln Ser Ser Gly Leu Tyr Ser Leu Ser Ser Val Val Ser
            180                 185                 190

Val Thr Ser Ser Ser Gln Pro Val Thr Cys Asn Val Ala His Pro Ala
            195                 200                 205

Thr Asn Thr Lys Val Asp Lys Thr Val Ala Pro Ser Thr Cys Ser Lys
210                 215                 220

Pro Thr Cys Pro Pro Pro Glu Leu Leu Gly Gly Pro Ser Val Phe Ile
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser Gln Asp Asp Pro Glu Val Gln
            260                 265                 270

Phe Thr Trp Tyr Ile Asn Asn Glu Gln Val Arg Thr Ala Arg Pro Pro
            275                 280                 285

Leu Arg Glu Gln Gln Phe Asn Ser Thr Ile Arg Val Val Ser Thr Leu
            290                 295                 300

Pro Ile Ala His Gln Asp Trp Leu Arg Gly Lys Glu Phe Lys Cys Lys
305                 310                 315                 320

Val His Asn Lys Ala Leu Pro Ala Pro Ile Glu Lys Thr Ile Ser Lys
                325                 330                 335

Ala Arg Gly Gln Pro Leu Glu Pro Lys Val Tyr Thr Met Gly Pro Pro
                340                 345                 350

Arg Glu Glu Leu Ser Ser Arg Ser Val Ser Leu Thr Cys Met Ile Asn
                355                 360                 365

Gly Phe Tyr Pro Ser Asp Ile Ser Val Glu Trp Glu Lys Asn Gly Lys
                370                 375                 380

Ala Glu Asp Asn Tyr Lys Thr Thr Pro Ala Val Leu Asp Ser Asp Gly
385                 390                 395                 400

Ser Tyr Phe Leu Tyr Ser Lys Leu Ser Val Pro Thr Ser Glu Trp Gln
                405                 410                 415

Arg Gly Asp Val Phe Thr Cys Ser Val Met His Glu Ala Leu His Asn
                420                 425                 430
```

```
His Tyr Thr Gln Lys Ser Ile Ser Arg Ser Pro Gly Lys
        435                 440             445

<210> SEQ ID NO 20
<211> LENGTH: 212
<212> TYPE: PRT
<213> ORGANISM: Artificial Sequence
<220> FEATURE:
<223> OTHER INFORMATION: Synthetic Polypeptide

<400> SEQUENCE: 20

Asp Val Val Met Thr Gln Thr Pro Ala Ser Val Ser Glu Pro Val Gly
1               5                   10                  15

Gly Thr Val Thr Ile Lys Cys Gln Ala Ser Gln Ser Ile Tyr Ser Gly
            20                  25                  30

Leu Ala Trp Tyr Gln Gln Lys Pro Gly Gln Pro Pro Lys Leu Leu Ile
        35                  40                  45

Tyr Asp Ala Ser Asp Leu Ala Ser Gly Val Pro Ser Arg Phe Ser Gly
50                  55                  60

Ser Gly Tyr Gly Thr Glu Phe Thr Leu Thr Ile Ser Gly Val Gln Cys
65                  70                  75                  80

Glu Asp Ala Ala Thr Tyr Tyr Cys Gln Val Thr His Tyr Glu Ser Gly
                85                  90                  95

Val Pro Leu Gly Gly Gly Thr Glu Val Val Glu Gly Asp Pro Val
            100                 105                 110

Ala Pro Thr Val Leu Leu Phe Pro Pro Ser Ser Asp Glu Val Ala Thr
        115                 120                 125

Gly Thr Val Thr Ile Val Cys Val Ala Asn Lys Tyr Phe Pro Asp Val
        130                 135                 140

Thr Val Thr Trp Glu Val Asp Gly Thr Gln Thr Thr Gly Ile Glu
145                 150                 155                 160

Asn Ser Lys Thr Pro Gln Asn Ser Ala Asp Cys Thr Tyr Asn Leu Ser
                165                 170                 175

Ser Thr Leu Thr Leu Thr Ser Thr Gln Tyr Asn Ser His Lys Glu Tyr
            180                 185                 190

Thr Cys Lys Val Thr Gln Gly Thr Ser Val Val Gln Ser Phe Ser
        195                 200                 205

Arg Lys Asn Cys
    210

<210> SEQ ID NO 21
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 21

Ser Tyr Tyr Tyr Met Cys
1               5

<210> SEQ ID NO 22
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 22
```

```
Cys Ile Phe Ser Asp Ser Gly Gly His Thr Ala Tyr Ala Ser Trp Ala
1               5                   10                  15

Glu Gly
```

<210> SEQ ID NO 23
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 23

```
Asp Arg Arg Asp Val Val Tyr Ile Arg Asp Leu
1               5                   10
```

<210> SEQ ID NO 24
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 24

```
Gln Ser Ser Glu Ser Val Tyr Asn Asn Asn Ala Leu Ala
1               5                   10
```

<210> SEQ ID NO 25
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 25

```
Gly Ala Ser Ser Leu Ala Ser
1               5
```

<210> SEQ ID NO 26
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 26

```
Ala Gly Tyr Lys Arg Tyr Asn Asn Asp Gly His Ala
1               5                   10
```

<210> SEQ ID NO 27
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 27

```
Gln Glu Gln Leu Glu Glu Ser Gly Gly Gly Leu Val Lys Pro Gly Gly
1               5                   10                  15

Thr Leu Thr Leu Thr Cys Lys Ala Ser Gly Met Asp Phe Ser Ser Tyr
            20                  25                  30

Tyr Tyr Met Cys Trp Val Arg Gln Ala Pro Gly Lys Gly Leu Glu Trp
        35                  40                  45

Ile Ala Cys Ile Phe Ser Asp Ser Gly Gly His Thr Ala Tyr Ala Ser
    50                  55                  60
```

```
Trp Ala Glu Gly Arg Phe Thr Ile Ser Lys Thr Ser Thr Thr Val
 65                  70                  75                  80

Thr Leu Gln Met Thr Ser Leu Thr Val Ala Asp Thr Ala Thr Tyr Phe
                 85                  90                  95

Cys Ala Arg Asp Arg Arg Asp Val Val Tyr Ile Arg Asp Leu Trp Gly
            100                 105                 110

Pro Gly Thr Leu Val Thr Val Ser Ser
            115                 120
```

<210> SEQ ID NO 28
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 28

```
Ala Leu Val Met Thr Gln Thr Pro Ser Pro Val Ser Ala Ala Val Gly
 1               5                  10                  15

Gly Thr Val Thr Ile Ser Cys Gln Ser Ser Glu Ser Val Tyr Asn Asn
                 20                  25                  30

Asn Ala Leu Ala Trp Tyr Gln Gln Lys Pro Gly Gln Pro Pro Lys Leu
             35                  40                  45

Leu Ile Tyr Gly Ala Ser Ser Leu Ala Ser Gly Val Pro Ser Arg Phe
         50                  55                  60

Lys Gly Ser Gly Ser Gly Thr Gln Phe Thr Leu Thr Ile Ser Asp Leu
 65                  70                  75                  80

Glu Cys Asp Asp Ala Ala Thr Tyr Tyr Cys Ala Gly Tyr Lys Arg Tyr
                 85                  90                  95

Asn Asn Asp Gly His Ala Phe Gly Gly Gly Thr Glu Val Val Val Lys
            100                 105                 110
```

<210> SEQ ID NO 29
<211> LENGTH: 444
<212> TYPE: PRT
<213> ORGANISM: Artificial Sequence
<220> FEATURE:
<223> OTHER INFORMATION: Synthetic Polypeptide

<400> SEQUENCE: 29

```
Gln Glu Gln Leu Glu Glu Ser Gly Gly Gly Leu Val Lys Pro Gly Gly
 1               5                  10                  15

Thr Leu Thr Leu Thr Cys Lys Ala Ser Gly Met Asp Phe Ser Ser Tyr
                 20                  25                  30

Tyr Tyr Met Cys Trp Val Arg Gln Ala Pro Gly Lys Gly Leu Glu Trp
             35                  40                  45

Ile Ala Cys Ile Phe Ser Asp Ser Gly Gly His Thr Ala Tyr Ala Ser
         50                  55                  60

Trp Ala Glu Gly Arg Phe Thr Ile Ser Lys Thr Ser Thr Thr Val
 65                  70                  75                  80

Thr Leu Gln Met Thr Ser Leu Thr Val Ala Asp Thr Ala Thr Tyr Phe
                 85                  90                  95

Cys Ala Arg Asp Arg Arg Asp Val Val Tyr Ile Arg Asp Leu Trp Gly
            100                 105                 110

Pro Gly Thr Leu Val Thr Val Ser Ser Gly Gln Pro Lys Ala Pro Ser
            115                 120                 125

Val Phe Pro Leu Ala Pro Cys Cys Gly Asp Thr Pro Ser Ser Thr Val
        130                 135                 140
```

Thr Leu Gly Cys Leu Val Lys Gly Tyr Leu Pro Glu Pro Val Thr Val
145                 150                 155                 160

Thr Trp Asn Ser Gly Thr Leu Thr Asn Gly Val Arg Thr Phe Pro Ser
                165                 170                 175

Val Arg Gln Ser Ser Gly Leu Tyr Ser Leu Ser Ser Val Val Ser Val
            180                 185                 190

Thr Ser Ser Ser Gln Pro Val Thr Cys Asn Val Ala His Pro Ala Thr
            195                 200                 205

Asn Thr Lys Val Asp Lys Thr Val Ala Pro Ser Thr Cys Ser Lys Pro
        210                 215                 220

Thr Cys Pro Pro Pro Glu Leu Leu Gly Gly Pro Ser Val Phe Ile Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Asp Asp Pro Glu Val Gln Phe
            260                 265                 270

Thr Trp Tyr Ile Asn Asn Glu Gln Val Arg Thr Ala Arg Pro Pro Leu
            275                 280                 285

Arg Glu Gln Gln Phe Asn Ser Thr Ile Arg Val Val Ser Thr Leu Pro
290                 295                 300

Ile Ala His Gln Asp Trp Leu Arg Gly Lys Glu Phe Lys Cys Lys Val
305                 310                 315                 320

His Asn Lys Ala Leu Pro Ala Pro Ile Glu Lys Thr Ile Ser Lys Ala
                325                 330                 335

Arg Gly Gln Pro Leu Glu Pro Lys Val Tyr Thr Met Gly Pro Pro Arg
            340                 345                 350

Glu Glu Leu Ser Ser Arg Ser Val Ser Leu Thr Cys Met Ile Asn Gly
            355                 360                 365

Phe Tyr Pro Ser Asp Ile Ser Val Glu Trp Glu Lys Asn Gly Lys Ala
        370                 375                 380

Glu Asp Asn Tyr Lys Thr Thr Pro Ala Val Leu Asp Ser Asp Gly Ser
385                 390                 395                 400

Tyr Phe Leu Tyr Ser Lys Leu Ser Val Pro Thr Ser Glu Trp Gln Arg
                405                 410                 415

Gly Asp Val Phe Thr Cys Ser Val Met His Glu Ala Leu His Asn His
            420                 425                 430

Tyr Thr Gln Lys Ser Ile Ser Arg Ser Pro Gly Lys
            435                 440

<210> SEQ ID NO 30
<211> LENGTH: 216
<212> TYPE: PRT
<213> ORGANISM: Artificial Sequence
<220> FEATURE:
<223> OTHER INFORMATION: Synthetic Polypeptide

<400> SEQUENCE: 30

Ala Leu Val Met Thr Gln Thr Pro Ser Pro Val Ser Ala Ala Val Gly
1               5                   10                  15

Gly Thr Val Thr Ile Ser Cys Gln Ser Ser Glu Ser Val Tyr Asn Asn
            20                  25                  30

Asn Ala Leu Ala Trp Tyr Gln Gln Lys Pro Gly Gln Pro Pro Lys Leu
        35                  40                  45

Leu Ile Tyr Gly Ala Ser Ser Leu Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Ala Gly Tyr Lys Arg Tyr
                85                  90                  95

Asn Asn Asp Gly His Ala Phe Gly Gly Gly Thr Glu Val Val Val Lys
            100                 105                 110

Gly Asp Pro Val Ala Pro Thr Val Leu Leu Phe Pro Pro Ser Ser Asp
        115                 120                 125

Glu Val Ala Thr Gly Thr Val Thr Ile Val Cys Val Ala Asn Lys Tyr
    130                 135                 140

Phe Pro Asp Val Thr Val Thr Trp Glu Val Asp Gly Thr Thr Gln Thr
145                 150                 155                 160

Thr Gly Ile Glu Asn Ser Lys Thr Pro Gln Asn Ser Ala Asp Cys Thr
                165                 170                 175

Tyr Asn Leu Ser Ser Thr Leu Thr Leu Thr Ser Thr Gln Tyr Asn Ser
            180                 185                 190

His Lys Glu Tyr Thr Cys Lys Val Thr Gln Gly Thr Thr Ser Val Val
        195                 200                 205

Gln Ser Phe Ser Arg Lys Asn Cys
    210                 215

<210> SEQ ID NO 31
<211> LENGTH: 323
<212> TYPE: PRT
<213> ORGANISM: Oryctolagus

<400> SEQUENCE: 31

Gly Gln Pro Lys Ala Pro Ser Val Phe Pro Leu Ala Pro Cys Cys Gly
1               5                   10                  15

Asp Thr Pro Ser Ser Thr Val Thr Leu Gly Cys Leu Val Lys Gly Tyr
            20                  25                  30

Leu Pro Glu Pro Val Thr Val Thr Trp Asn Ser Gly Thr Leu Thr Asn
        35                  40                  45

Gly Val Arg Thr Phe Pro Ser Val Arg Gln Ser Ser Gly Leu Tyr Ser
    50                  55                  60

Leu Ser Ser Val Val Ser Val Thr Ser Ser Ser Gln Pro Val Thr Cys
65                  70                  75                  80

Asn Val Ala His Pro Ala Thr Asn Thr Lys Val Asp Lys Thr Val Ala
                85                  90                  95

Pro Ser Thr Cys Ser Lys Pro Thr Cys Pro Pro Pro Glu Leu Leu Gly
            100                 105                 110

Gly Pro Ser Val Phe Ile Phe Pro Pro Lys Pro Lys Asp Thr Leu Met
        115                 120                 125

Ile Ser Arg Thr Pro Glu Val Thr Cys Val Val Val Asp Val Ser Gln
    130                 135                 140

Asp Asp Pro Glu Val Gln Phe Thr Trp Tyr Ile Asn Asn Glu Gln Val
145                 150                 155                 160

Arg Thr Ala Arg Pro Pro Leu Arg Glu Gln Gln Phe Asn Ser Thr Ile
                165                 170                 175

Arg Val Val Ser Thr Leu Pro Ile Ala His Gln Asp Trp Leu Arg Gly
            180                 185                 190

Lys Glu Phe Lys Cys Lys Val His Asn Lys Ala Leu Pro Ala Pro Ile
        195                 200                 205

Glu Lys Thr Ile Ser Lys Ala Arg Gly Gln Pro Leu Glu Pro Lys Val

```
                210                 215                 220
Tyr Thr Met Gly Pro Pro Arg Glu Glu Leu Ser Ser Arg Ser Val Ser
225                 230                 235                 240

Leu Thr Cys Met Ile Asn Gly Phe Tyr Pro Ser Asp Ile Ser Val Glu
                245                 250                 255

Trp Glu Lys Asn Gly Lys Ala Glu Asp Asn Tyr Lys Thr Thr Pro Ala
                260                 265                 270

Val Leu Asp Ser Asp Gly Ser Tyr Phe Leu Tyr Ser Lys Leu Ser Val
                275                 280                 285

Pro Thr Ser Glu Trp Gln Arg Gly Asp Val Phe Thr Cys Ser Val Met
                290                 295                 300

His Glu Ala Leu His Asn His Tyr Thr Gln Lys Ser Ile Ser Arg Ser
305                 310                 315                 320

Pro Gly Lys

<210> SEQ ID NO 32
<211> LENGTH: 104
<212> TYPE: PRT
<213> ORGANISM: Oryctolagus

<400> SEQUENCE: 32

Gly Asp Pro Val Ala Pro Thr Val Leu Leu Phe Pro Pro Ser Ser Asp
1               5                   10                  15

Glu Val Ala Thr Gly Thr Val Thr Ile Val Cys Val Ala Asn Lys Tyr
                20                  25                  30

Phe Pro Asp Val Thr Val Thr Trp Glu Val Asp Gly Thr Thr Gln Thr
                35                  40                  45

Thr Gly Ile Glu Asn Ser Lys Thr Pro Gln Asn Ser Ala Asp Cys Thr
            50                  55                  60

Tyr Asn Leu Ser Ser Thr Leu Thr Leu Thr Ser Thr Gln Tyr Asn Ser
65              70                  75                  80

His Lys Glu Tyr Thr Cys Lys Val Thr Gln Gly Thr Thr Ser Val Val
                85                  90                  95

Gln Ser Phe Ser Arg Lys Asn Cys
                100

<210> SEQ ID NO 33
<211> LENGTH: 184
<212> TYPE: PRT
<213> ORGANISM: Homo Sapiens

<400> SEQUENCE: 33

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
            35                  40                  45

Val Lys Gly Thr Asn Ala Ile Leu Trp Thr Cys Leu Gly Leu Ser Leu
            50                  55                  60

Ile Ile Ser Leu Ala Val Phe Val Leu Met Phe Leu Leu Arg Lys Ile
65              70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
                100                 105                 110
```

```
Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 34
<211> LENGTH: 54
<212> TYPE: PRT
<213> ORGANISM: Homo Sapiens

<400> SEQUENCE: 34

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala
    50

<210> SEQ ID NO 35
<211> LENGTH: 18
<212> TYPE: PRT
<213> ORGANISM: Homo Sapiens

<400> SEQUENCE: 35

Cys Gln Leu Arg Cys Ser Ser Asn Thr Pro Pro Leu Thr Cys Gln Arg
1               5                   10                  15

Tyr Cys
```